United States Patent
Kadoch et al.

(10) Patent No.: US 10,752,628 B2
(45) Date of Patent: Aug. 25, 2020

(54) COMPOUNDS AND METHODS FOR TREATING SYNOVIAL SARCOMAS

(71) Applicants: THE BROAD INSTITUTE, INC., Cambridge, MA (US); PRESIDENT AND FELLOWS OF HARVARD COLLEGE, Cambridge, MA (US); DANA-FARBER CANCER INSTITUTE, INC., Boston, MA (US)

(72) Inventors: Cigall Kadoch, Boston, MA (US); Enrique Garcia-Rivera, Cambridge, MA (US); Micah Maetani, Cambridge, MA (US); Stuart L. Schreiber, Cambridge, MA (US)

(73) Assignees: THE BROAD INSTITUTE, INC., Cambridge, MA (US); PRESIDENT AND FELLOWS OF HARVARD COLLEGE, Cambridge, MA (US); DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 15/774,530

(22) PCT Filed: Nov. 16, 2016

(86) PCT No.: PCT/US2016/062296
§ 371 (c)(1),
(2) Date: May 8, 2018

(87) PCT Pub. No.: WO2017/087534
PCT Pub. Date: May 26, 2017

(65) Prior Publication Data
US 2018/0327407 A1  Nov. 15, 2018

Related U.S. Application Data

(60) Provisional application No. 62/255,767, filed on Nov. 16, 2015.

(51) Int. Cl.
*C07D 471/20* (2006.01)

(52) U.S. Cl.
CPC .................. *C07D 471/20* (2013.01)

(58) Field of Classification Search
CPC .................................................... C07D 471/20
See application file for complete search history.

(56) References Cited

U.S. PATENT DOCUMENTS

| 2009/0326218 A1 | 12/2009 | Martin et al. |
| 2016/0152617 A1* | 6/2016 | Comer ................ C07D 471/20 514/229.5 |
| 2018/0303802 A1* | 10/2018 | Kadoch ................ A61K 31/395 |

FOREIGN PATENT DOCUMENTS

| WO | 2015/002755 A2 | 1/2015 |
| WO | 2015058125 A1 | 4/2015 |
| WO | 2017/062510 A1 | 4/2017 |

OTHER PUBLICATIONS

Spira et al., "The Use of Chemotherapy in Soft-Tissue Sarcomas" The Oncologist, 2002, vol. 7, No. 4, pp. 348-359. (Year: 2002).*
Extended European Search Report, dated Mar. 20, 2019, received in corresponding European Patent Application No. 16867046.1, (5 pages).
International Search Report and Written Opinion for corresponding PCT Application No. PCT/US2016/062296, dated Feb. 7, 2017 (11 pages).

* cited by examiner

*Primary Examiner* — Joseph R Kosack
(74) *Attorney, Agent, or Firm* — Melissa Hunter-Ensor; John L. Buchanan; Greenberg Traurig, LLP

(57) ABSTRACT

The present invention includes compound and methods that are useful in treating certain cancers, such as synovial sarcomas.

20 Claims, 18 Drawing Sheets
Specification includes a Sequence Listing.

FIG. 2
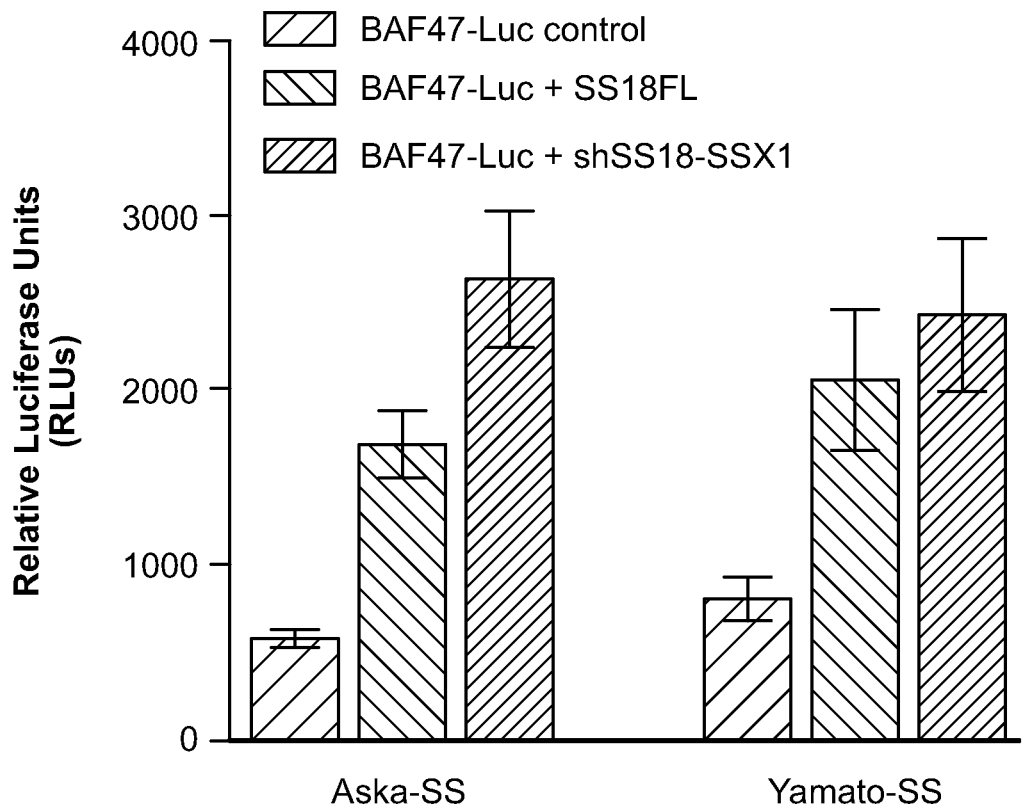
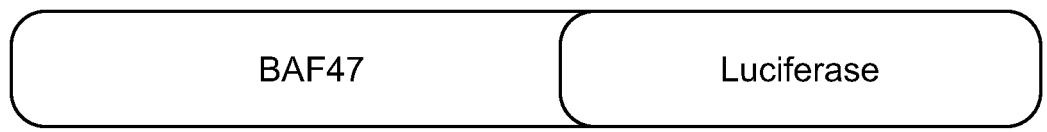

FIG. 5A
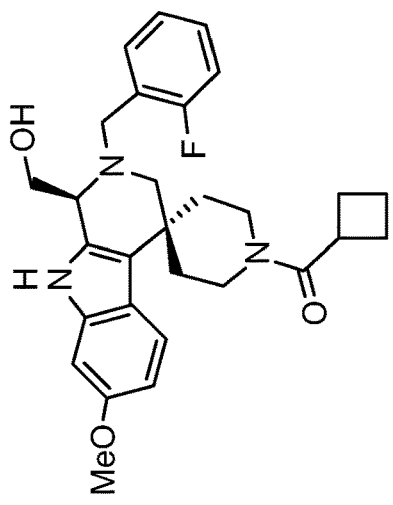
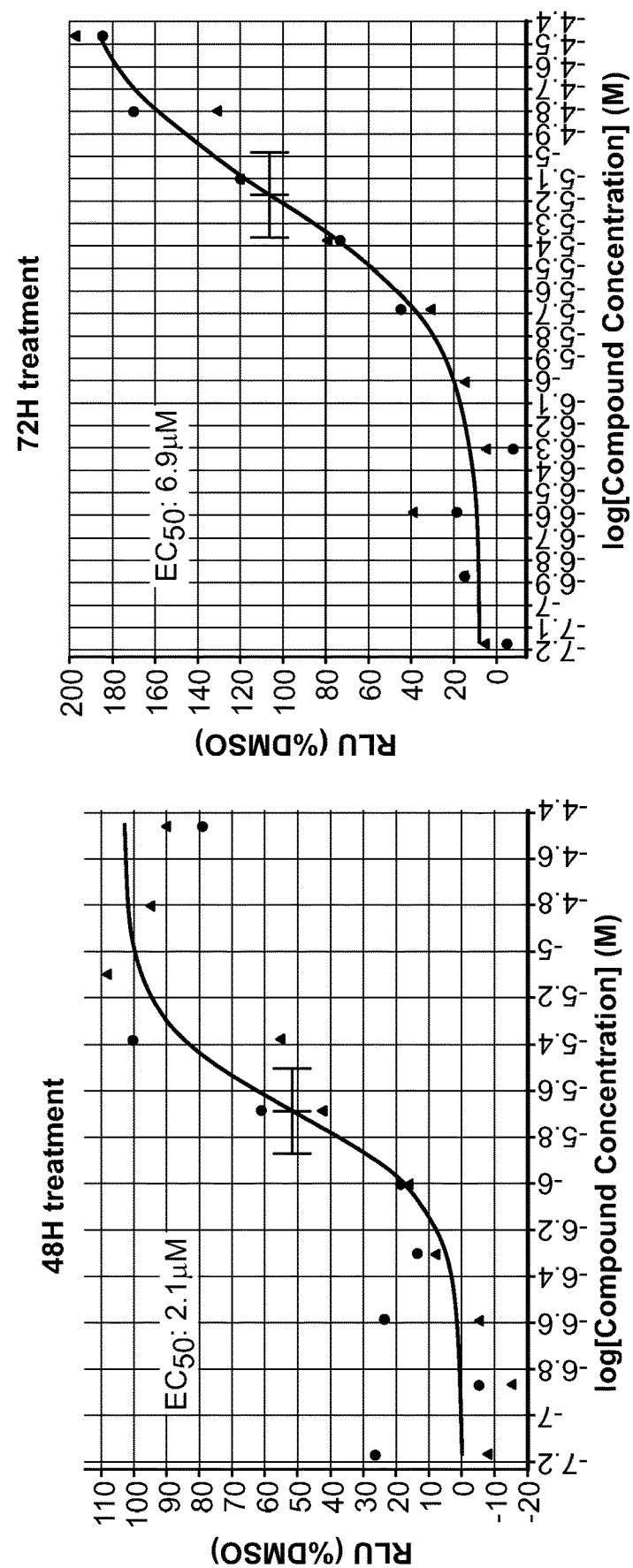

FIG. 5B
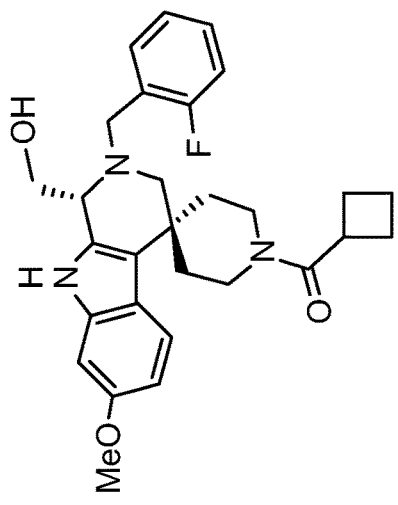
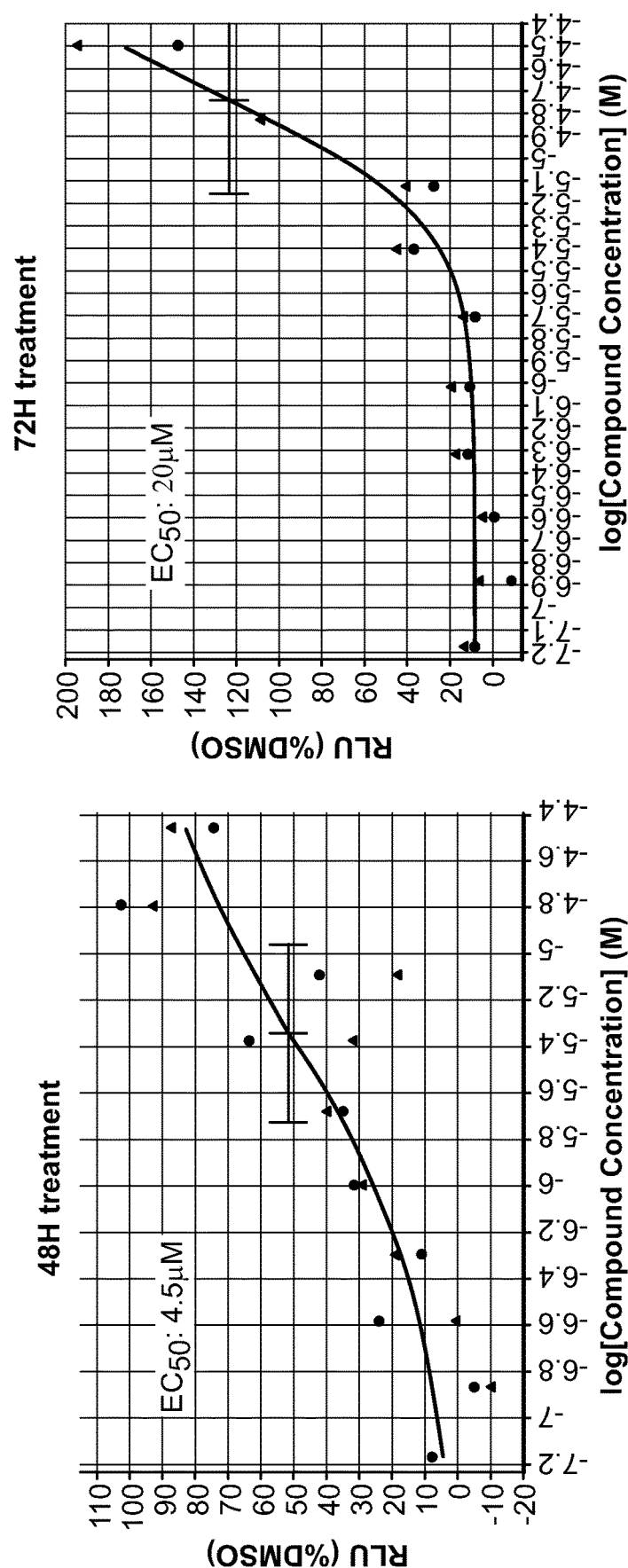

FIG. 8
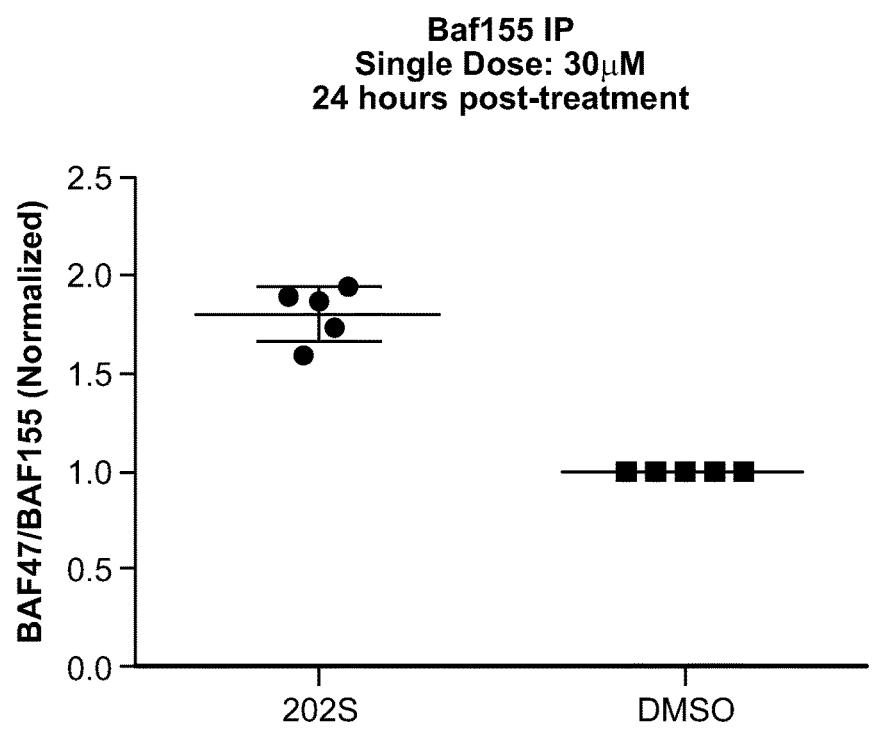
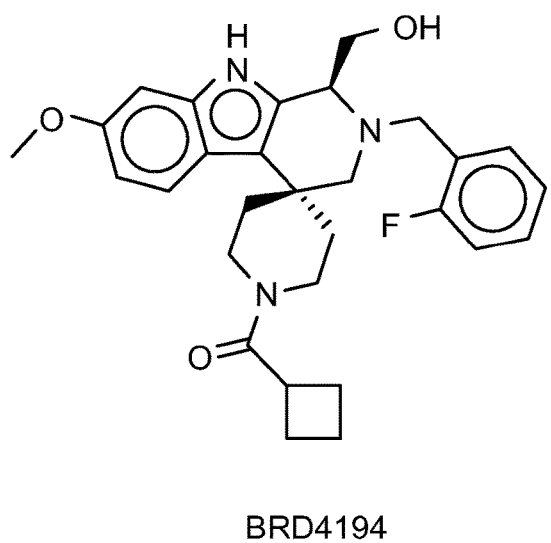
BRD4194
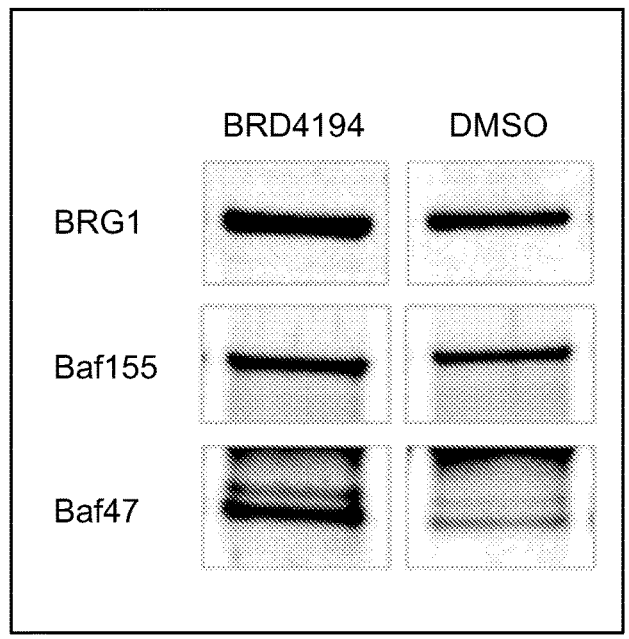

FIG. 10
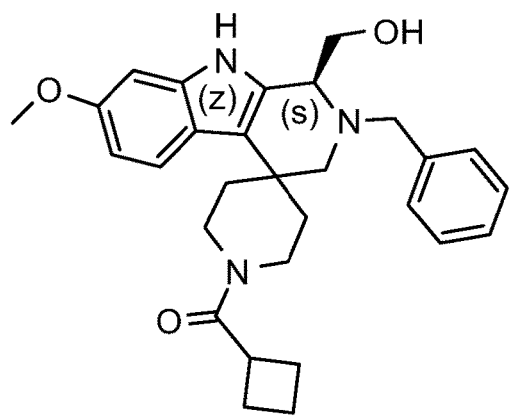
MM2-218a
("All-H")
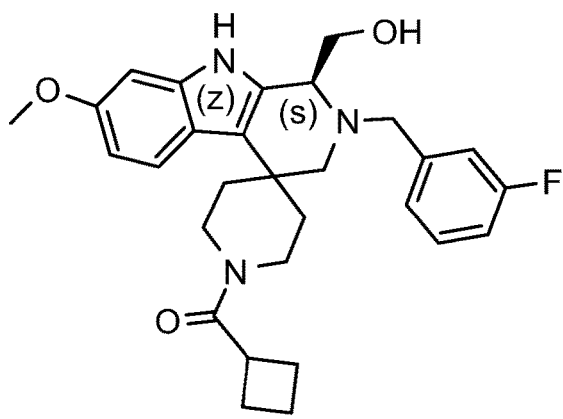
MM2-218b
("M-F")
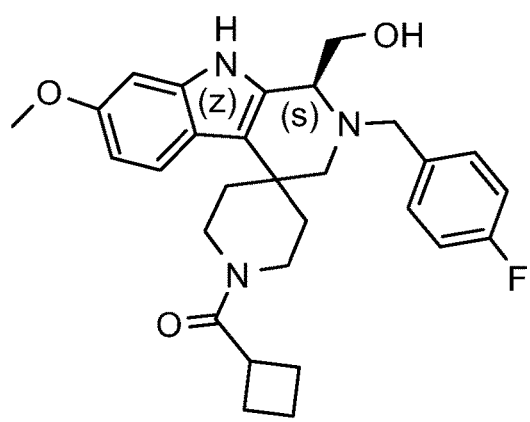
MM2-218c
("P-F")
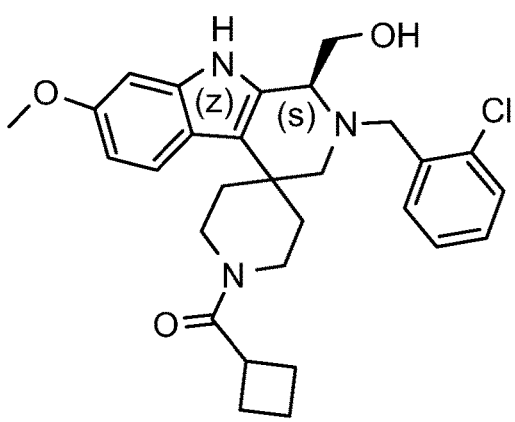
MM2-218d
("O-Cl")

FIG. 15A
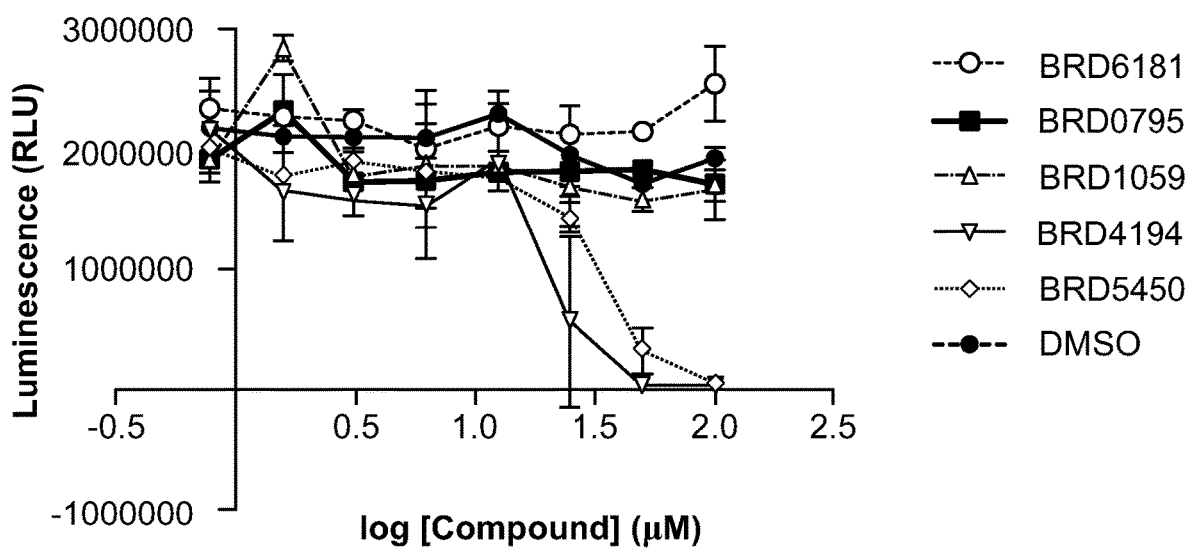
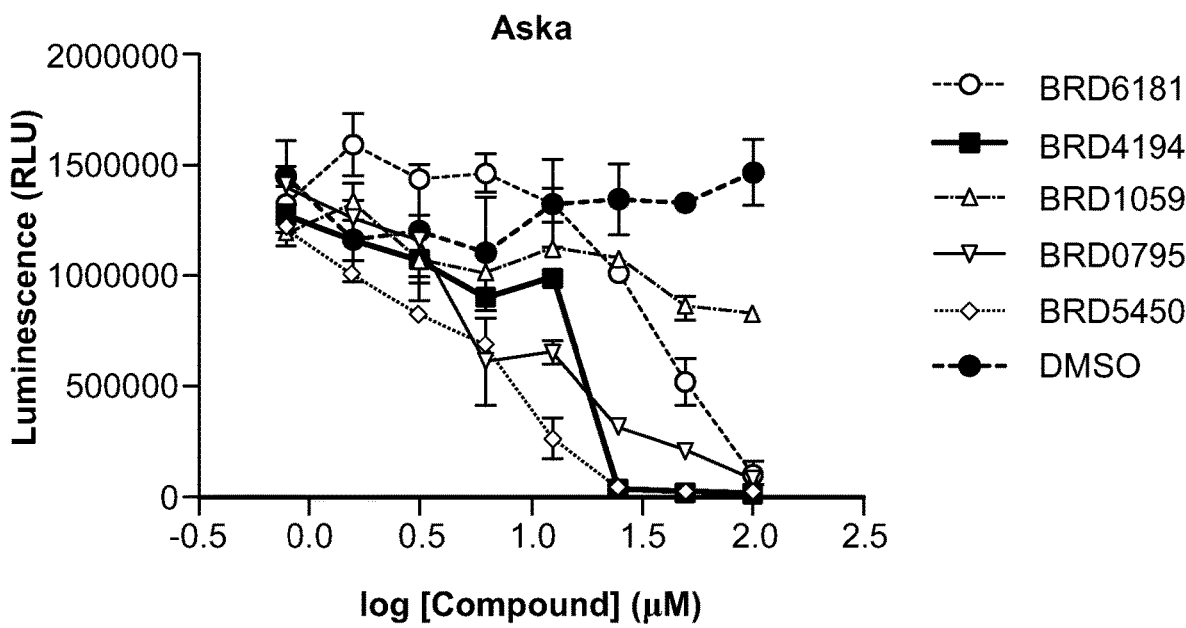

FIG. 15B
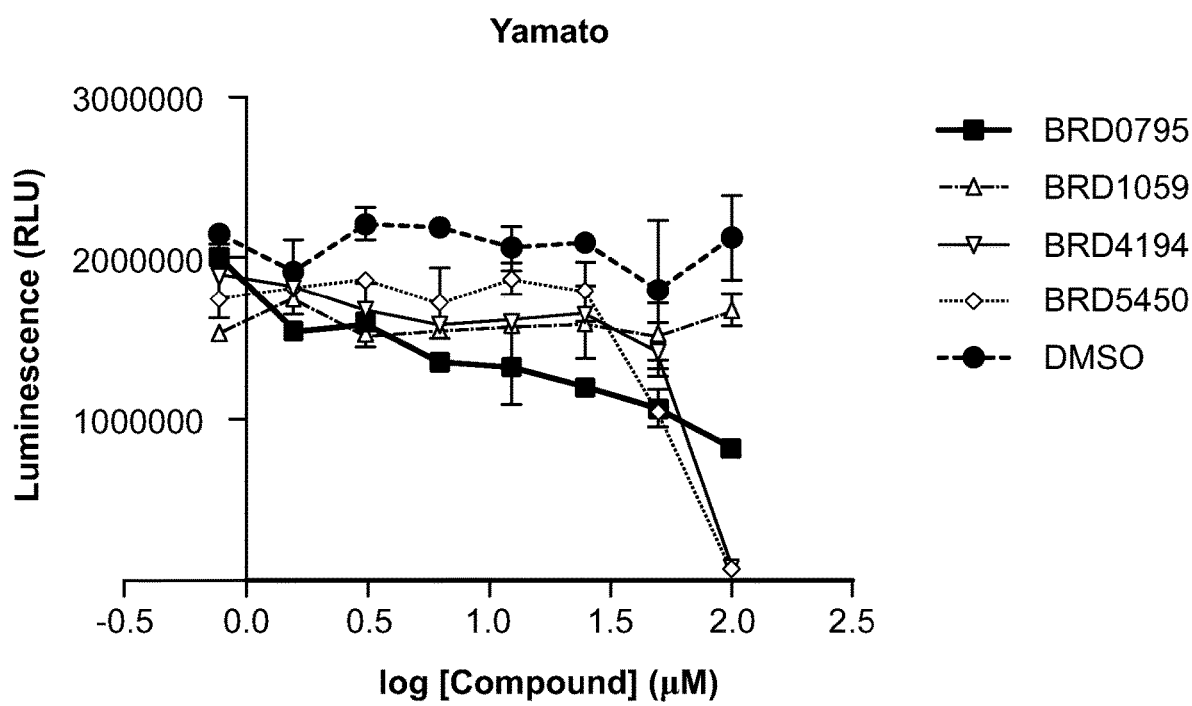
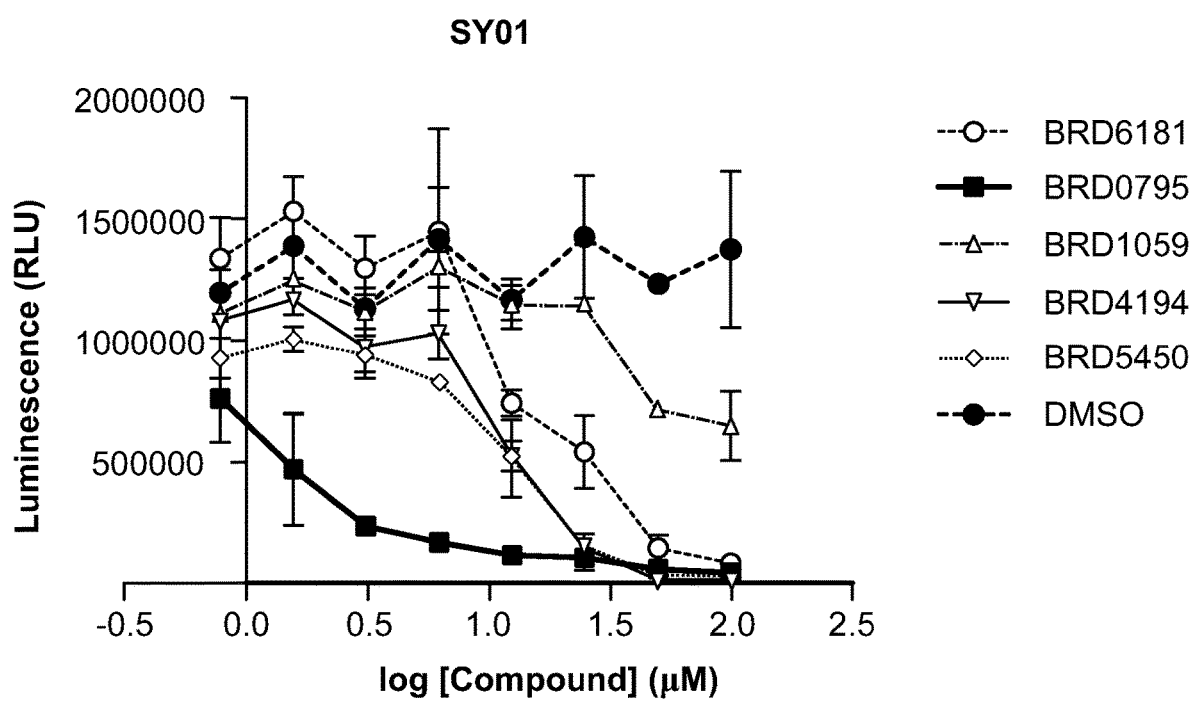

COMPOUNDS AND METHODS FOR TREATING SYNOVIAL SARCOMAS

CROSS-REFERENCE TO RELATED APPLICATION

This application is the U.S. national phase application, pursuant to 35 U.S.C. § 371, of PCT International Application Ser. No.: PCT/US2016/062296, filed Nov. 16, 2016, designating the United States and published in English, which claims the benefit of the following U.S. Provisional Application No. 62/255,767, filed Nov. 16, 2015, the entire contents of which are incorporated herein by reference.

STATEMENT REGARDING FEDERALLY SPONSORED RESEARCH OR DEVELOPMENT

This invention was made with government support under Grant Nos. CA168512 and OD019696 awarded by the National Institutes of Health. The government has certain rights in the invention.

BACKGROUND OF THE INVENTION

A synovial sarcoma (also known as malignant synovioma) is a rare form of soft tissue cancer, and usually occurs near to the joints of the arm, neck or leg. Despite the propensity of some sarcomas to arise adjacent to joints, synovial sarcomas are not necessarily synovial in nature. In fact, synovial sarcomas have been documented in most human tissues and organs, including the brain, prostate and heart, most commonly in the extremities of young adults.

Synovial sarcoma occurs most commonly in the young, representing about 8-10% of all soft tissue sarcomas and about 15-20% of cases in adolescents and young adults. The peak of incidence is before the age of 30, with a ratio of 1.2:1 for males-to-females. The presentation of synovial sarcomas usually comprises an otherwise asymptomatic swelling or mass, sometimes accompanied by fatigue.

Synovial sarcoma is uniquely characterized by the balanced chromosomal translocation t(X,18; p11.2,q11.2), which is demonstrable in virtually all cases of synovial sarcomas and not found in any other human neoplasms. This translocation creates an in-frame fusion of the SS18 gene to SSX1 or SSX2, whereby all but the C-terminal eight amino acids of SS18 become fused to the C-terminal 78 amino acids of the SSX partner. An analogous translocation of SSX4 is detected in less than 1% of cases. This recurrent aberration leads to the fusion of two proteins, SS18 (SYT) and SSX (SSX1, SSX2, or SSX4), generating an oncogene that is necessary for synovial sarcoma initiation and propagation.

The mammalian nucleosome remodeling SWI/SNF complex (known in humans as "BRG1- or HRBM-associated factors" or BAF complex) is a group of proteins that tightly associate to remodel the way DNA is packaged. It is composed of several proteins mammalian versions of products of the yeast SWI and SNF genes (SWI1, SWI2/SNF2, SWI3, SWI5, SWI6), as well as other polypeptides. The BRG subunit of the complex has DNA-stimulated ATPase activity, and the complex can destabilize histone-DNA interactions in reconstituted nucleosomes in an ATP-dependent manner. The BAF complex acts as a tumor suppressor in many human cancers, and is mutated in about 20% of human malignancies. In synovial sarcomas, the SS18-SSX fusion protein integrates as a stable member of the BAF complex, replacing the product of the wild-type allele, the SS18 subunit, causing dramatic changes in the complex composition, including the ejection and degradation of the core subunit BAF47 (SNF5) from the complex.

Treatment of synovial sarcomas generally involves surgery, chemotherapy and radiotherapy, in view of the fact that no on-target biologics have been developed to date. Surgery to remove the tumor and surrounding tissue is curative in approximately 20-70% of patients. Conventional chemotherapy, such as doxorubicin hydrochloride and ifosfamide, reduces the number of remaining microscopic cancer cells, but its benefit for overall survival remains unclear. Radiotherapy is thought to reduce the chance of local recurrence. However, the disease is prone to early and late recurrences, and the ten-year disease-free survival rate remains on the order of 50%. Further, none of these approaches appears to address the underlying mechanism of this rare form of cancer.

There is a need in the art to identify novel compounds that can be used to treat or prevent synovial sarcomas in mammals. The present invention meets this need.

SUMMARY OF THE INVENTION

As described below, the present invention generally provides compounds that are useful in treating or preventing synovial sarcomas in mammals. The present invention further provides pharmaceutical compositions comprising at least one compound of the invention and a pharmaceutically acceptable carrier. The present invention further provides methods of treating or preventing synovial sarcomas in mammals. In certain embodiments, the compounds of the invention stabilize BAF47 within the SWI/SNF (BAF) complex in the mammal.

In various embodiments of any of the above aspects or any other aspects of the invention delineated herein, the compound of the invention is a compound having the structure of formula I:

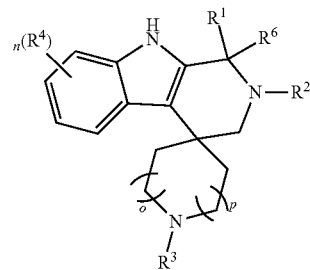

Formula I wherein n is 1, 2, 3, or 4;
o and p are independently 0, 1, or 2;
$R^1$ and $R^6$ are, independently, selected from the group consisting of H and $C_1$-$C_6$ alkyl, wherein the alkyl group is optionally substituted with at least one independently selected from the group consisting of $C_1$-$C_6$ alkyl, $C_3$-$C_8$ cycloalkyl, halo, —OH, $C_1$-$C_6$ alkoxy, $C_1$-$C_6$ haloalkoxy, —$NH_2$, —NHC(=O)($C_1$-$C_6$ alkyl), —NH($C_1$-$C_6$ alkyl) and —N($C_1$-$C_6$ alkyl)($C_1$-$C_6$ alkyl);
$R^2$ is hydrogen, $C_1$-$C_6$ alkyl, $C_1$-$C_6$ perfluoroalkyl, $C_6$-$C_{10}$ aryl $C_1$-$C_6$ alkyl, $C_1$-$C_6$ heteroaryl $C_1$-$C_6$ alkyl, $C_2$-$C_9$ heterocyclyl $C_1$-$C_6$ alkyl, or $C_3$-$C_{10}$ carbocyclyl $C_1$-$C_6$ alkyl, wherein the alkyl group is optionally substituted with at least one independently selected from the group consisting of $C_1$-$C_6$ alkyl, $C_3$-$C_8$ cycloalkyl, halo, —OH, $C_1$-$C_6$ alkoxy, $C_1$-$C_6$ haloalkoxy, —$NH_2$, —NHC(=O) ($C_1$-$C_6$ alkyl), —NH($C_1$-$C_6$ alkyl) and —N($C_1$-$C_6$ alkyl) ($C_1$-$C_6$ alkyl) and the aryl, heteroaryl, heterocyclyl, or carbocyclyl group is optionally substituted with at least one independently selected from the group consisting of $C_1$-$C_6$ alkyl, $C_1$-$C_6$ haloalkyl, $C_3$-$C_8$ cycloalkyl, halo, —OH, $C_1$-$C_6$ alkoxy, $C_1$-$C_6$ haloalkoxy, —NH$_2$, —NH($C_1$-$C_6$ alkyl), —N($C_1$-$C_6$ alkyl)($C_1$-$C_6$ alkyl), —NO$_2$, —C(=O)OH, —C(=O)OR, and —NHC(=O)($C_1$-$C_6$ alkyl);

$R^3$ is selected from the group consisting of H, $C_1$-$C_6$ alkyl, $C_2$-$C_9$ heteroaryl, $C_6$-$C_{10}$ aryl $C_1$-$C_6$ alkyl, $C_1$-$C_6$ heteroaryl $C_1$-$C_6$ alkyl, $C_2$-$C_9$ heterocyclyl $C_1$-$C_6$ alkyl, $C_2$-$C_9$ heteroaryl $C_1$-$C_6$ alkyl, or $C_3$-$C_{10}$ carbocyclyl $C_1$-$C_6$ alkyl, —S(=O)$_2$R, —C(=O)R, —C(=O)OR, —S(=O)$_2$NHR and —C(=O)NR$_2$, wherein the alkyl group is optionally substituted with at least one independently selected from the group consisting of $C_1$-$C_6$ alkyl, $C_3$-$C_8$ cycloalkyl, halo, —OH, $C_1$-$C_6$ alkoxy, $C_1$-$C_6$ haloalkoxy, —NH$_2$, —NHC(=O)($C_1$-$C_6$ alkyl), —NH($C_1$-$C_6$ alkyl) and —N($C_1$-$C_6$ alkyl)($C_1$-$C_6$ alkyl) and the aryl, heteroaryl, heterocyclyl, or carbocyclyl group is optionally substituted with at least one independently selected from the group consisting of $C_1$-$C_6$ alkyl, $C_1$-$C_6$ haloalkyl, $C_3$-$C_8$ cycloalkyl, halo, —OH, $C_1$-$C_6$ alkoxy, $C_1$-$C_6$ haloalkoxy, —NH$_2$, —NH($C_1$-$C_6$ alkyl), —N($C_1$-$C_6$ alkyl)($C_1$-$C_6$ alkyl), —NO$_2$, —C(=O)OH, —C(=O)OR, and —NHC(=O)($C_1$-$C_6$ alkyl);

each occurrence of $R^4$ is independently selected from the group consisting of $C_1$-$C_6$ alkyl, $C_1$-$C_6$ haloalkyl, $C_3$-$C_8$ cycloalkyl, halo, —OH, $C_1$-$C_6$ alkoxy, $C_1$-$C_6$ haloalkoxy, —NH$_2$, —NH($C_1$-$C_6$ alkyl), —N($C_1$-$C_6$ alkyl)($C_1$-$C_6$ alkyl), —NO$_2$, —C(=O)OH, —C(=O)OR, and —NHC(=O)($C_1$-$C_6$ alkyl); and each R is, independently, selected from the group consisting of hydrogen, $C_1$-$C_6$ alkyl, $C_1$-$C_6$ heteroaryl, $C_6$-$C_{10}$ aryl, $C_3$-$C_8$ cycloalkyl, $C_2$-$C_9$ heterocyclyl, $C_6$-$C_{10}$ aryl $C_1$-$C_6$ alkyl, $C_1$-$C_6$ heteroaryl $C_1$-$C_6$ alkyl, wherein the alkyl, cycloalkyl, aryl, heteroaryl, or heterocyclyl group is optionally substituted with at least one independently selected from the group consisting of $C_1$-$C_6$ alkyl, —OH, —($C_1$-$C_6$ alkoxy), halo, —NH$_2$, —NHC(=O)($C_1$-$C_6$ alkyl), —NH($C_1$-$C_6$ alkyl) and —N($C_1$-$C_6$ alkyl)($C_1$-$C_6$ alkyl).

In some embodiments, the compound may have the structure of formula (II), or a salt, solvate or stereoisomer thereof:

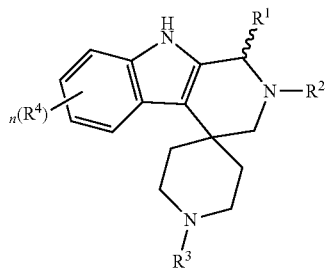

Formula (II)

wherein $R^1$ is selected from the group consisting of H and $C_1$-$C_6$ alkyl, wherein the alkyl group is optionally substituted with at least one independently selected from the group consisting of $C_1$-$C_6$ alkyl, $C_3$-$C_8$ cycloalkyl, halo, —OH, $C_1$-$C_6$ alkoxy, $C_1$-$C_6$ haloalkoxy, —NH$_2$, —NHC(=O)($C_1$-$C_6$ alkyl), —NH($C_1$-$C_6$ alkyl) and —N($C_1$-$C_6$ alkyl)($C_1$-$C_6$ alkyl); $R^2$ is (CH$_2$)$_m$R$^5$, wherein m is 1, 2 or 3, and wherein $R^5$ is selected from the group consisting of aryl and heteroaryl, wherein the aryl or heteroaryl group is optionally substituted with at least one independently selected from the group consisting of $C_1$-$C_6$ alkyl, $C_1$-$C_6$ haloalkyl, $C_3$-$C_8$ cycloalkyl, halo, —OH, $C_1$-$C_6$ alkoxy, $C_1$-$C_6$ haloalkoxy, —NH$_2$, —N($C_1$-$C_6$ alkyl), —N($C_1$-$C_6$ alkyl)($C_1$-$C_6$ alkyl), —NO$_2$, —C(=O)OH, —C(=O)OR, and —NHC(=O)($C_1$-$C_6$ alkyl); $R^3$ is selected from the group consisting of H, —S(=O)$_2$R, —C(=O)R, —S(=O)$_2$NHR and —C(=O)NHR, wherein R is selected from the group consisting of $C_1$-$C_6$ alkyl and $C_3$-$C_8$ cycloalkyl, wherein the alkyl or cycloalkyl group is optionally substituted with at least one independently selected from the group consisting of $C_1$-$C_6$ alkyl, —OH, ($C_1$-$C_6$ alkoxy), halo, —NH$_2$, —NHC(=O)($C_1$-$C_6$ alkyl), —NH($C_1$-$C_6$ alkyl) and —N($C_1$-$C_6$ alkyl)($C_1$-$C_6$ alkyl); each occurrence of $R^4$ is independently selected from the group consisting of $C_1$-$C_6$ alkyl, $C_1$-$C_6$ haloalkyl, $C_3$-$C_8$ cycloalkyl, halo, —OH, $C_1$-$C_6$ alkoxy, $C_1$-$C_6$ haloalkoxy, —NH$_2$, —NH($C_1$-$C_6$ alkyl), —N($C_1$-$C_6$ alkyl)($C_1$-$C_6$ alkyl), —NO$_2$, —C(=O)OH, —C(=O)OR, and —NHC(=O)($C_1$-$C_6$ alkyl); and n is 0, 1, 2, 3 or 4.

In various embodiments of any of the above aspects or any other aspects of the invention delineated herein, the compound of formula (II) is a compound of formula (IIA), or a salt or solvate thereof:

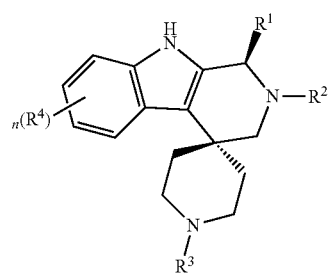

Formula IIA

In various embodiments of any of the above aspects or any other aspects of the invention delineated herein, the compound of formula (II) is a compound of formula (IIB), or a salt or solvate thereof:

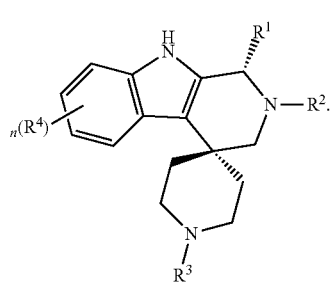

Formula IIB

In certain embodiments, $R^1$ is selected from the group consisting of H and $C_1$-$C_6$ alkyl, wherein the alkyl group is optionally substituted with at least one independently selected from the group consisting of $C_1$-$C_6$ alkyl, halo, —OH, $C_1$-$C_6$ alkoxy, and $C_1$-$C_6$ haloalkoxy. In other embodiments, $R^1$ is selected from the group consisting of H and $C_1$-$C_6$ alkyl, wherein the alkyl group is optionally substituted with at least one independently selected from the group consisting of halo, —OH, $C_1$-$C_6$ alkoxy, and $C_1$-$C_6$ haloalkoxy. In yet other embodiments, $R^1$ is selected from the group consisting of H and —CH$_2$OH. In yet other embodiments, m is 1. In yet other embodiments, $R^5$ is aryl optionally substituted with at least one independently selected from the group consisting of $C_1$-$C_6$ alkyl, $C_1$-$C_6$ haloalkyl, $C_3$-$C_8$ cycloalkyl, halo, —OH, $C_1$-$C_6$ alkoxy, $C_1$-$C_6$ haloalkoxy, —NH$_2$, —NH($C_1$-$C_6$ alkyl), —N($C_1$-$C_6$ alkyl)($C_1$-$C_6$ alkyl), —NO$_2$, —C(=O)OH, —C(=O)OR, and —NHC(=O)($C_1$-$C_6$ alkyl). In yet other embodiments, $R^2$ is CH$_2$R$^5$, and $R^5$ is aryl optionally substituted with at least one independently selected from the group consisting of $C_1$-$C_6$ alkyl, $C_1$-$C_6$ haloalkyl, $C_3$-$C_8$ cycloalkyl, halo, —OH, $C_1$-$C_6$ alkoxy, and $C_1$-$C_6$ haloalkoxy. In yet other embodiments, $R^5$ is selected from the group consisting of 2-fluorophenyl, 3-fluorophenyl, 4-fluorophenyl, 2-chlorophenyl, 3-chlorophenyl, 4-chlorophenyl, 2,5-difluorophenyl, 2,5-dichlorophenyl, 2-chloro-5-fluorophenyl, and 5-chloro-2-fluorophenyl. In yet other embodiments, $R^3$ is selected from the group consisting of H, —S(=O)$_2$R, —C(=O)R, —S(=O)$_2$NHR and —C(=O)NHR, wherein R is selected from the group consisting of $C_1$-$C_6$ alkyl and $C_3$-$C_8$ cycloalkyl. In yet other embodiments, each occurrence of $R^4$ is independently selected from the group consisting of $C_1$-$C_6$ alkyl, $C_1$-$C_6$ haloalkyl, $C_3$-$C_8$ cycloalkyl, halo, —OH, $C_1$-$C_6$ alkoxy and $C_1$-$C_6$ haloalkoxy. In yet other embodiments, n is 1, and $R^4$ is at the 7' position of formula (II).

In various embodiments of any of the above aspects or any other aspects of the invention delineated herein, the compound is selected from the group consisting of:

(S)-cyclobutyl(2'-(2-fluorobenzyl)-1'-(hydroxymethyl)-7'-methoxy-1',2',3',9'-tetrahydrospiro[piperidine-4,4'-pyrido[3,4-b]indol]-1-yl)methanone:

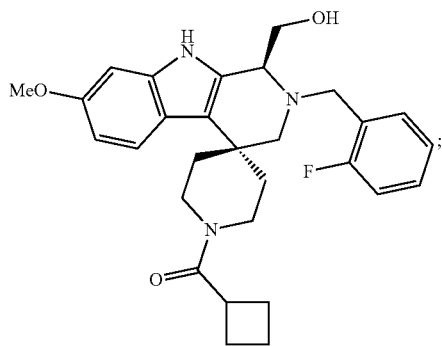

(R)-cyclobutyl(2'-(2-fluorobenzyl)-1'-(hydroxymethyl)-7'-methoxy-1',2',3',9'-tetrahydrospiro[piperidine-4,4'-pyrido[3,4-b]indol]-1-yl)methanone:

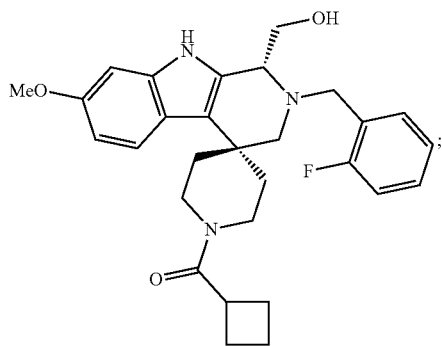

cyclobutyl(2'-(2-fluorobenzyl)-7'-methoxy-1',2',3',9'-tetrahydrospiro[piperidine-4,4'-pyrido[3,4-b]indol]-1-yl)methanone:

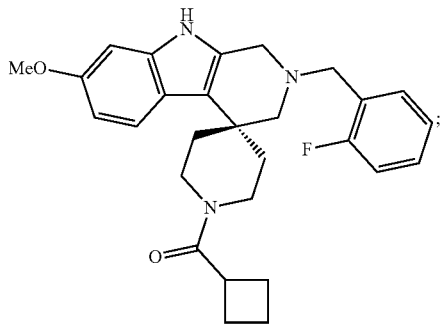

(S)-(2'-benzyl-1'-(hydroxymethyl)-7'-methoxy-1',2',3',9'-tetrahydrospiro[piperidine-4,4'-pyrido[3,4-b]indol]-1-yl)(cyclobutyl):

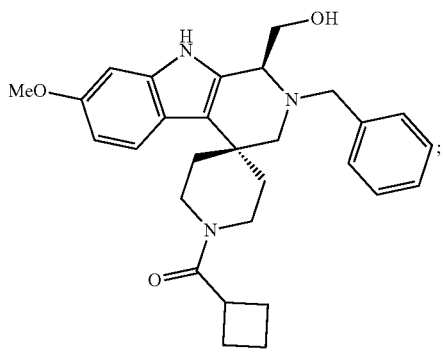

(S)-cyclobutyl(2'-(3-fluorobenzyl)-1'-(hydroxymethyl)-7'-methoxy-1',2',3',9'-tetrahydrospiro[piperidine-4,4'-pyrido[3,4-b]indol]-1-yl)methanone:

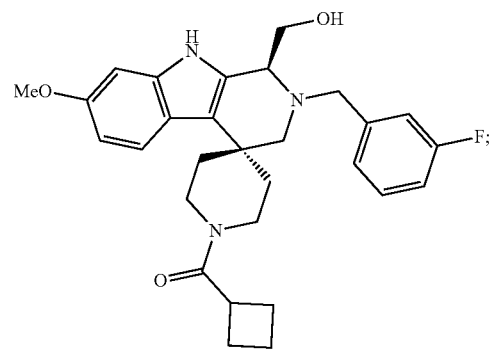

(S)-cyclobutyl(2'-(4-fluorobenzyl)-1'-(hydroxymethyl)-7'-methoxy-1',2',3',9'-tetrahydrospiro[piperidine-4,4'-pyrido[3,4-b]indol]-1-yl)methanone:

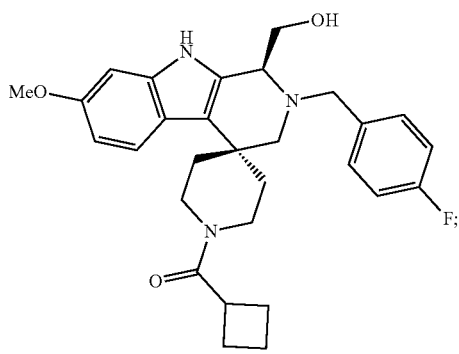

(S)-(2'-(2-chlorobenzyl)-1'-(hydroxymethyl)-7'-methoxy-1',2',3',9'-tetrahydrospiro[piperidine-4,4'-pyrido[3,4-b]indol]-1-yl)(cyclobutyl)methanone:

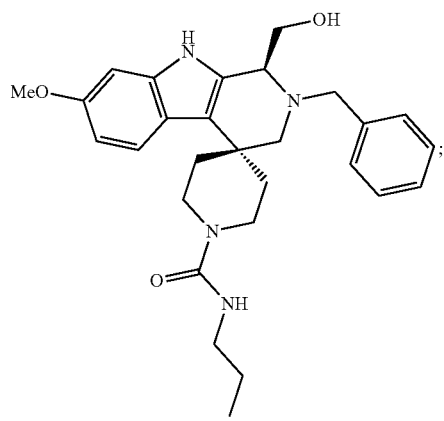

(S)-cyclobutyl(2'-(2,5-difluorobenzyl)-1'-(hydroxymethyl)-7'-methoxy-1',2',3',9'-tetrahydrospiro[piperidine-4,4'-pyrido[3,4-b]indol]-1-yl)methanone:

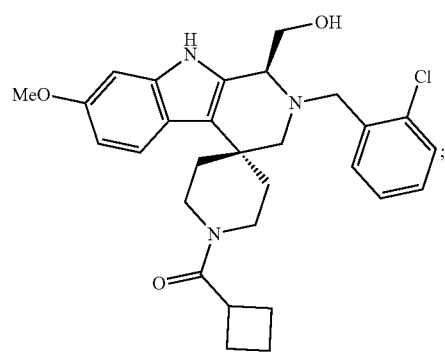

(R)-2'-benzyl-1'-(hydroxymethyl)-7'-methoxy-N-propyl-1',2',3',9'-tetrahydrospiro[piperidine-4,4'-pyrido[3,4-b]indole]-1-carboxamide:

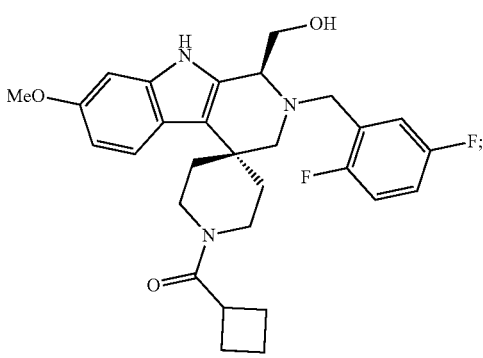

(S)-cyclopentyl(2'-(2-fluorobenzyl)-1'-(hydroxymethyl)-7'-methoxy-1',2',3',9'-tetrahydrospiro[piperidine-4,4'-pyrido[3,4-b]indol]-1-yl)methanone:

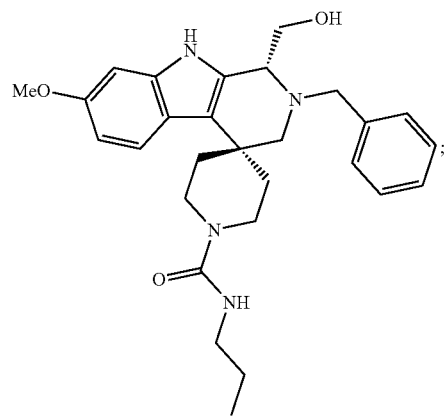

(S)-2'-benzyl-1'-(hydroxymethyl)-7'-methoxy-N-propyl-1',2',3',9'-tetrahydrospiro[piperidine-4,4'-pyrido[3,4-b]indole]-1-carboxamide:

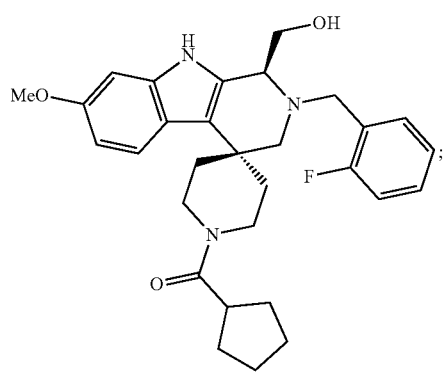

(R)-cyclopentyl(2'-(2-fluorobenzyl)-1'-(hydroxymethyl)-7'-methoxy-1',2',3',9'-tetrahydrospiro[piperidine-4,4'-pyrido[3,4-b]indol]-1-yl)methanone:

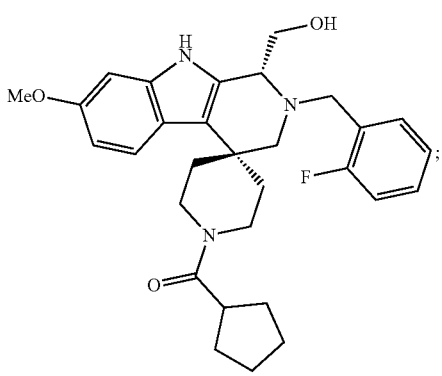

or a salt, solvate, mixture or stereoisomer thereof.

In certain embodiments, the pharmaceutical composition further comprises at least one additional anticancer agent selected from the group consisting of doxorubicin and ifosfamide.

In various embodiments of any of the above aspects or any other aspects of the invention delineated herein, the method comprises administering to the mammal in need thereof a therapeutically effective amount of at least one compound of the invention. In certain embodiments, the mammal is further administered at least one additional anticancer agent selected from the group consisting of doxorubicin and ifosfamide. In other embodiments, the at least one additional agent and the at least one compound are co-administered to the mammal. In yet other embodiments, the at least one additional agent and the at least one compound are co-formulated. In yet other embodiments, the mammal further receives radiotherapy to treat or prevent the synovial sarcoma. In yet other embodiments, the at least one compound is administered to the mammal by at least one route selected from the group consisting of nasal, inhalational, topical, oral, buccal, rectal, pleural, peritoneal, vaginal, intramuscular, subcutaneous, transdermal, epidural, intrathecal and intravenous routes. In yet other embodiments, the mammal is human.

Compositions and articles defined by the invention were isolated or otherwise manufactured in connection with the examples provided below. Other features and advantages of the invention will be apparent from the detailed description, and from the claims.

BRIEF DESCRIPTION OF THE DRAWINGS

The following detailed description of specific embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

FIG. 2 comprises a diagram and a bar graph that illustrate the finding that BAF47 protein levels correlate with SS18-SSX expression and incorporation into the BAF complex. The assay used comprises transducing a reporter fusion DNA construct comprising BAF47 fused to luciferase into synovial sarcoma cell lines, such as but not limited to Aska and Yamato. The bar graphs illustrate relative luciferase units for transduced cell lines without and with alteration at the SS18/SS18-SSX axis. Briefly, Aska synovial sarcoma cells were infected via lentivirus to introduce the BAF47-Luciferase fusion construct. Cells were then co-infected with either shRNA to the SS18-SSX fusion or overexpression of SS18. Both of these conditions resulted in an increase of BAF47-Luciferase signal as measured by RLU, reflecting increase stability of BAF47 in the complex.

FIGS. 5A-5B comprise exemplary dose response curves for Compound 5 (FIG. 5A) and Compound 6 (FIG. 5B).

FIG. 8 comprises a series of images and graph illustrating the activity of Compound 5 in Yamato cells. Briefly, Yamato cells were treated with 30 µM compound for 24 hours over n=5 replicates. The graph depicts levels of BAF47 in DMSO treated vs Compound 5-treated cells. Lower panel: western blot image depicting stabilization of BAF47 in Aska-SS cells upon treatment with Compound 5.

FIG. 10 illustrates certain compounds of the invention.

FIGS. 15A-15C comprise a set of graphs illustrating the finding that compounds of the invention reduce synovial sarcoma cell viability as measured by CellTiter Glog luminescence. As shown, Compound 5 and Compound 6, the two lead hits, resulted in cell toxicity in Aska synovial sarcoma cells.

DETAILED DESCRIPTION OF THE INVENTION

Figure 1:
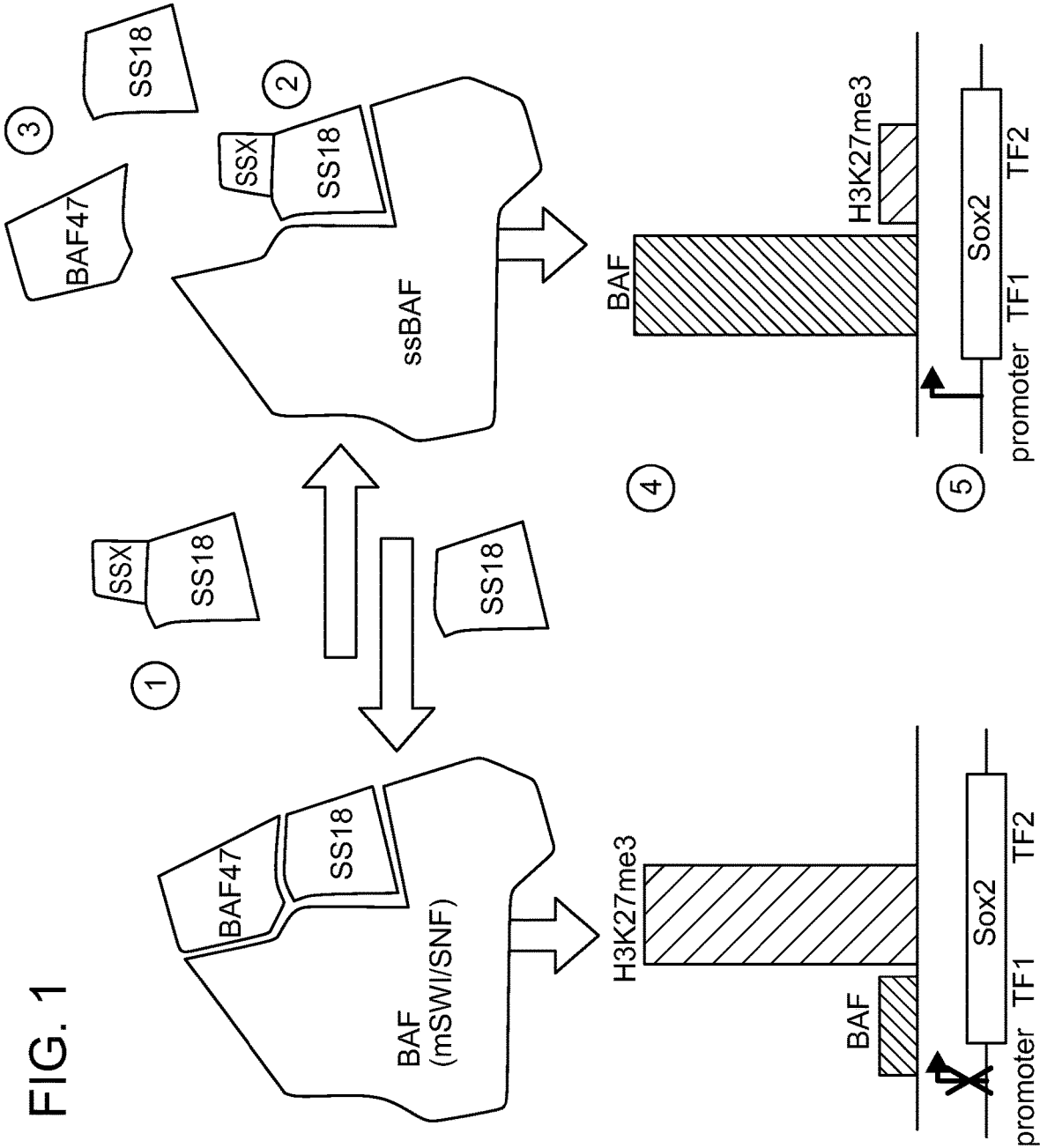
FIG. 1 comprises a schematic illustration of the role of BAF and the SS18-SSX fusion protein in synovial sarcoma (SS). In the illustration: (1) t(X;18) translocation results in expression of the SS18-SSX fusion protein; (2) The SS18-SSX fusion protein integrates into the BAF complex; (3) Wild-type SS18 and BAF47 are displaced from the BAF complex, and BAF47 is subsequently degraded; (4) The BAF complex localizes over the Sox2 locus, and H3K27me3 marks are removed; (5) Sox2 mRNA expression is induced to promote SS proliferation.

The present invention generally provides compounds that are useful in treating or preventing synovial sarcomas in mammals. The present invention further generally provides methods of treating or preventing synovial sarcomas in mammals. In certain embodiments, the compounds of the invention stabilize BAF47 within the SWI/SNF (BAF) complex in the mammal.

Definitions

Unless defined otherwise, all technical and scientific terms used herein generally have the same meaning as commonly understood by one of ordinary skill in the art to which this invention belongs. The following references provide one of skill with a general definition of many of the terms used in this invention: Singleton et al., Dictionary of Microbiology and Molecular Biology ($2^{nd}$ Ed. 1994); The Cambridge Dictionary of Science and Technology (Walker, Ed., 1988); The Glossary of Genetics, 5th Ed., R. Rieger, et al. (Eds.), Springer Verlag (1991); and Hale & Marham, The Harper Collins Dictionary of Biology (1991). Generally, the nomenclature used herein and the laboratory procedures in medicine, organic chemistry and molecular biology are those well known and commonly employed in the art.

As used herein, the articles "a" and "an" refer to one or to more than one (i.e., to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "administration" means providing the compound and/or composition of the present invention to a subject by any suitable method.

As used herein, the term "alkenyl" employed alone or in combination with other terms means, unless otherwise stated, a stable mono-unsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—CH═$CH_2$.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, such as, but not limited to, ethoxy and methoxy.

As used herein, the term "alkyl" by itself or as part of another sub stituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$)alkyl, such as, but not limited to, ethyl, methyl, isopropyl, isobutyl, n-pentyl, n-hexyl and cyclopropylmethyl.

As used herein, the term "alkynyl" employed alone or in combination with other terms means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —$CH_2$—C≡CH. The term "homopropargylic" refers to a group exemplified by —$CH_2CH_2$—C≡CH. The term "substituted propargylic" refers to a group exemplified by —$CR_2$—C≡CR, wherein each occurrence of R is independently H, alkyl, substituted alkyl, alkenyl or substituted alkenyl, with the proviso that at least one R group is not hydrogen. The term "substituted homopropargylic" refers to a group exemplified by —$CR_2CR_2$—C≡CR, wherein each occurrence of R is independently H, alkyl, substituted alkyl, alkenyl or substituted alkenyl, with the proviso that at least one R group is not hydrogen.

By "ameliorate" is meant decrease, suppress, attenuate, diminish, arrest, or stabilize the development or progression of a disease or disorder.

As used herein, an "amino acid" is represented by the full name thereof, by the three-letter code, as well as the one-letter code corresponding thereto, as indicated in the following table. The structure of amino acids and their abbreviations can also be found in the chemical literature, such as in Stryer, 1988, "Biochemistry", $3^{rd}$ Ed., W. H. Freeman and Co., New York.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl" or "arene" employed alone or in combination with other terms means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl (including 1- and 2-naphthyl). Preferred are phenyl and naphthyl, most preferred is phenyl.

As used herein, the term "aryl-($C_1$-$C_3$)alkyl" means a functional group wherein a one to three carbon alkylene chain is attached to an aryl group, e.g., —$CH_2CH_2$-phenyl or —$CH_2$-phenyl (benzyl). Preferred is aryl-$CH_2$— and aryl-CH($CH_3$)—. The term "substituted aryl-($C_1$-$C_3$)alkyl" means an aryl-($C_1$-$C_3$)alkyl functional group in which the aryl group is substituted. Preferred is substituted aryl ($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$)alkyl" means a heteroaryl-($C_1$-$C_3$)alkyl functional group in which the heteroaryl group is substituted. Preferred is substituted heteroaryl-($CH_2$)—.

As used herein, the term "BAF complex" refers to the BRG1- or HRBM-associated factors complex in a human cell.

As used herein, the term "BAF47" (also known as SWI/SNF-related matrix-associated actin-dependent regulator of chromatin subfamily B member 1) refers to the following polypeptide and/or any polypeptide with at least 90% identity, preferably 95% identity, more preferably 98% identity to its sequence:

```
         10         20         30         40
  MMMMALSKTF GQKPVKFQLE DDGEFYMIGS EVGNYLRMFR 50         60         70         80
  GSLYKRYPSL WRRLATVEER KKIVASSHGK KTKPNTKDHG 90        100        110        120
  YTTLATSVTL LKASEVEEIL DGNDEKYKAV SISTEPPTYL 130        140        150        160
  REQKAKRNSQ WVPTLPNSSH HLDAVPCSTT INRNRMGRDK 170        180        190        200
  KRTFPLCFDD HDPAVIHENA SQPEVLVPIR LDMEIDGQKL 210        220        230        240
  RDAFTWNMNE KLMTPEMFSE ILCDDLDLNP LTFVPAIASA 250        260        270        280
  IRQQIESYPT DSILEDQSDQ RVIIKLNIHV GNISLVDQFE 290        300        310        320
  WDMSEKENSP EKFALKLCSE LGLGGEFVTT IAYSIRGQLS 330        340        350        360
  WHQKTYAFSE NPLPTVEIAI RNTGDADQWC PLLETLTDAE 370        380
  MEKKIRDQDR NTRRMRRLAN TAPAW
```

As used herein, the term "Compound 1" refers to N-(2-aminophenyl)-4-(((((2S,3R)-5-((R)-1-hydroxypropan-2-yl)-3-methyl-6-oxo-10-(4-(thiazol-2-yl)benzamido)-3,4,5,6-tetrahydro-2H-benzo[b][1,5]oxazocin-2-yl)methyl)(methyl) amino)methyl)benzamide, or a salt, solvate or stereoisomer thereof.

As used herein, the term "Compound 2" refers to (R)-2'-benzyl-1'-(hydroxymethyl)-7'-methoxy-N-propyl-1',2',3',9'-tetrahydrospiro[piperidine-4,4'-pyrido[3,4-b]indole]-1-carboxamide, or a salt, solvate or stereoisomer thereof.

As used herein, the term "Compound 3" refers to N-(((2S, 3R)-8-(3-cyclohexylureido)-5-((R)-1-hydroxypropan-2-yl)-3-methyl-6-oxo-3,4,5,6-tetrahydro-2H-benzo[b][1,5]oxazocin-2-yl)methyl)-N-methylthiophene-2-sulfonamide, or a salt, solvate or stereoisomer thereof.

As used herein, the term "Compound 4" refers to (S)-cyclopentyl(2'-(2-fluorobenzyl)-1'-(hydroxymethyl)-7'-methoxy-1',2',3',9'-tetrahydrospiro[piperidine-4,4'-pyrido[3,4-b]indol]-1-yl)methanone, or a salt, solvate or stereoisomer thereof.

As used herein, the term "Compound 5" refers to (S)-cyclobutyl(2'-(2-fluorobenzyl)-1'-(hydroxymethyl)-7'-methoxy-1',2',3',9'-tetrahydrospiro[piperidine-4,4'-pyrido[3,4-b]indol]-1-yl)methanone, or a salt, solvate or stereoisomer thereof.

As used herein, the term "Compound 6" refers to (R)-cyclobutyl(2'-(2-fluorobenzyl)-1'-(hydroxymethyl)-7'-methoxy-1',2',3',9'-tetrahydrospiro[piperidine-4,4'-pyrido[3,4-b]indol]-1-yl)methanone, or a salt, solvate or stereoisomer thereof.

As used herein, the term "Compound 7" refers to (R)-cyclopentyl(2'-(2-fluorobenzyl)-1'-(hydroxymethyl)-7'-methoxy-1',2',3',9'-tetrahydrospiro[piperidine-4,4'-pyrido[3,4-b]indol]-1-yl)methanone, or a salt, solvate or stereoisomer thereof.

As used herein, the term "Compound 8" refers to N-(2-aminophenyl)-4-(((((13  S,15R,5R,11R)-35-(dimethylamino)-15-(hydroxymethyl)-5-methyl-2-oxo-4,10-dioxa-1 (1,3)-pyrrolidina-3(1,2)-benzenacycloundecaphane-11-yl) methyl)(methyl)amino)methyl) benzamide, or a salt, solvate or stereoisomer thereof.

As used herein, the term "Compound 9" refers to (S)-cyclobutyl(2'-(2,5-difluorobenzyl)-1'-(hydroxymethyl)-7'-methoxy-1',2',3',9'-tetrahydrospiro[piperidine-4,4'-pyrido[3,4-b]indol]-1-yl)methanone:

As used herein, the term "Compound 10" refers to (S)-2'-benzyl-1'-(hydroxymethyl)-7'-methoxy-N-propyl-1',2',3', 9'-tetrahydrospiro[piperidine-4,4'-pyrido[3,4-b]indole]-1-carboxamide, or a salt, solvate or stereoisomer thereof.

As used herein, the term "Compound 11" refers to cyclobutyl(2'-(2-fluorobenzyl)-7'-methoxy-1',2',3',9'-tetrahydrospiro[piperidine-4,4'-pyrido[3,4-b]indol]-1-yl)methanone, or a salt, solvate or stereoisomer thereof.

As used herein, the term "Compound 12" refers to (S)-(2'-benzyl-1'-(hydroxymethyl)-7'-methoxy-1',2',3',9'-tetrahydrospiro[piperidine-4,4'-pyrido[3,4-b]indol]-1-yl)(cyclobutyl)methanone, or a salt, solvate or stereoisomer thereof.

As used herein, the term "Compound 13" refers to (S)-cyclobutyl(2'-(3-fluorobenzyl)-1'-(hydroxymethyl)-7'-methoxy-1',2',3',9'-tetrahydrospiro[piperidine-4,4'-pyrido[3,4-b]indol]-1-yl)methanone, or a salt, solvate or stereoisomer thereof.

As used herein, the term "Compound 14" refers to (S)-cyclobutyl(2'-(4-fluorobenzyl)-1'-(hydroxymethyl)-7'-methoxy-1',2',3',9'-tetrahydrospiro[piperidine-4,4'-pyrido[3,4-b]indol]-1-yl)methanone, or a salt, solvate or stereoisomer thereof.

As used herein, the term "Compound 15" refers to (S)-(2'-(2-chlorobenzyl)-1'-(hydroxymethyl)-7'-methoxy-1',2', 3',9'-tetrahydrospiro[piperidine-4,4'-pyrido[3,4-b]indol]-1-yl)(cyclobutyl)methanone, or a salt, solvate or stereoisomer thereof.

In one aspect, the terms "co-administered" and "co-administration" as relating to a subject refer to administering to the subject a compound and/or composition of the invention, or salt thereof, along with a compound and/or composition that may also treat any of the diseases contemplated within the invention. In one embodiment, the co-administered compounds and/or compositions are administered separately, or in any kind of combination as part of a single therapeutic approach. The co-administered compound and/or composition may be formulated in any kind of combinations as mixtures of solids and liquids under a variety of solid, gel, and liquid formulations, and as a solution.

As used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, the term "composition" or "pharmaceutical composition" refers to a mixture of at least one compound useful within the invention with a pharmaceutically acceptable carrier. The pharmaceutical composition facilitates administration of the compound to a subject.

As used herein, the term "cycloalkyl" by itself or as part of another substituent means, unless otherwise stated, a cyclic chain hydrocarbon having the number of carbon atoms designated (i.e., $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is ($C_3$-$C_6$)cycloalkyl, such as, but not limited to, cyclopropyl, cyclobutyl, cyclopentyl and cyclohexyl.

By "decreases" is meant a negative alteration of at least about 10%, 25%, 50%, 75%, 100%, or more.

"Detect" refers to identifying the presence, absence or amount of the analyte to be detected.

By "disease" or "disorder" is meant any condition that damages or interferes with the normal function of a cell, tissue, or organ.

As used herein, the term "DMSO" refers to dimethylsulfoxide.

By "effective amount" is meant the amount of a compound that is required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least about 10%, 20%, 30%, 40%, 50%, 60%, 70%, 80%, or 90% of the entire length of the reference nucleic acid molecule or polypeptide. A fragment may contain about 10, 20, 30, 40, 50, 60, 70, 80, 90, or 100, 200, 300, 400, 500, 600, 700, 800, 900, or 1,000 nucleotides or amino acids.

As used herein, the term "halo" or "halogen" employed alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$ As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listings of heterocyclyl and heteroaryl moieties are intended to be representative and not limiting.

By "identity" is meant the amino acid or nucleic acid sequence identity between a sequence of interest and a reference sequence. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BEST-FIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

The term "including" is used herein to mean, and is used interchangeably with, the phrase "including but not limited to."

By "increases" is meant a positive alteration of at least about 10%, 25%, 50%, 75%, 100%, or more.

As used herein, the term "instructional material" includes a publication, a recording, a diagram, or any other medium of expression that may be used to communicate the usefulness of the compositions and methods of the invention. In some instances, the instructional material may be part of a kit useful for treating and/or preventing synovial sarcomas in a subject (e.g., a mammal, human, etc.). The instructional material of the kit may, for example, be affixed to a container that contains the compositions of the invention or be shipped together with a container that contains the compositions. Alternatively, the instructional material may be shipped separately from the container with the intention that the recipient uses the instructional material and the compositions cooperatively. For example, the instructional material is for use of a kit; instructions for use of the compositions; or instructions for use of a formulation of the compositions.

The terms "isolated," "purified," or "biologically pure" refer to material that is free to varying degrees from components that normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid, peptide or compound of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

As used herein, "naturally occurring amino acid" includes L-isomers of the twenty amino acids naturally occurring in proteins (plus cystine), as illustrated in Table 1. Unless specially indicated, all amino acids referred to in this application are in the L-form.

TABLE 1

| Full Name | Three-Letter Code | One-Letter Code | Full Name | Three-Letter Code | One-Letter Code |
| --- | --- | --- | --- | --- | --- |
| Alanine | Ala | A | Leucine | Leu | L |
| Arginine | Arg | R | Lysine | Lys | K |
| Asparagine | Asn | N | Methionine | Met | M |
| Aspartic Acid | Asp | D | Phenylalanine | Phe | F |
| Cysteine | Cys | C | Proline | Pro | P |
| Cystine | Cys-Cys | C-C | Serine | Ser | S |
| Glutamic Acid | Glu | E | Threonine | Thr | T |
| Glutamine | Gln | Q | Tryptophan | Trp | W |
| Glycine | Gly | G | Tyrosine | Tyr | Y |
| Histidine | His | H | Valine | Val | V |
| Isoleucine | Ile | I | | | |

As used herein, the terms "peptide," "polypeptide," or "protein" are used interchangeably, and refer to a compound comprised of amino acid residues covalently linked by peptide bonds. A protein or peptide must contain at least two amino acids, and no limitation is placed on the maximum number of amino acids that can comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogues and fusion proteins, among others. The polypeptides include natural peptides, recombinant peptides, synthetic peptides or a combination thereof. A peptide that is not cyclic has a N-terminus and a C-terminus. The N-terminus has an amino group, which may be free (i.e., as a $NH_2$ group) or appropriately protected (e.g., with a BOC or a Fmoc group). The C-terminus has a carboxylic group, which may be free (i.e., as a COOH group) or appropriately protected (e.g., as a benzyl or a methyl ester). A cyclic peptide does not necessarily have free N- or C-termini, since they are covalently bonded through an amide bond to form the cyclic structure.

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, inorganic bases, organic bases, solvates, hydrates, or clathrates thereof. The compounds described herein may form salts with acids or bases, and such salts are included in the present invention. In one embodiment, the salts are pharmaceutically acceptable salts. The term "salts" embraces addition salts of free acids or bases that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts of compounds of the invention may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compounds by reacting, for example, the appropriate acid or base with the compound.

The term "prevent" or "preventing" or "prevention," as used herein, means avoiding or delaying the onset of symptoms associated with a disease or condition in a subject that has not developed such symptoms at the time the administering of an agent or compound commences. Disease, condition, and disorder are used interchangeably herein.

As used herein, the term "reaction condition" refers to a physical treatment, chemical reagent, or combination thereof, which is required or optionally required to promote a reaction. Non-limiting examples of reaction conditions are electromagnetic radiation, heat, a catalyst, a chemical reagent (such as, but not limited to, an acid, base, electrophile or nucleophile), and a buffer.

By "reference" is meant a standard or control condition.

A "reference sequence" is a defined sequence used as a basis for sequence comparison.

As used herein, the term "subject," "patient" or "individual" may be a human or non-human mammal or a bird. Non-human mammals include, for example, livestock and pets, such as ovine, bovine, equine, porcine, canine, feline and murine mammals. Preferably, the subject is human.

As used herein, the term "substituted" means that an atom or group of atoms has replaced hydrogen as the substituent attached to another group. Unless stated otherwise, any group recited within the invention may be substituted.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_1$-$C_6$ alkyl, —OH, $C_1$-$C_6$ alkoxy, halo, amino, acetamido and nitro. As used herein, where a substituent is an alkyl or alkoxy group, the carbon chain may be branched, straight or cyclic, with straight being preferred.

As used herein, the term "SS" refers to a synovial sarcoma.

As used herein, a chemical structure comprising a "wavy" bond is meant to indicate that the compound may be in both the (R) or the (S) configuration. Any stereocenters without labeled chirality are also meant to indicate that each stereocenter may be in the (R) or (S) configuration.

The terms "treat" and "treating" and "treatment," as used herein, means reducing the frequency or severity with which symptoms of a disease or condition are experienced by a subject by virtue of administering an agent or compound to the subject.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Any compounds, compositions, or methods provided herein can be combined with one or more of any of the other compositions and methods provided herein.

Other features and advantages of the invention will be apparent from the following description of the desirable embodiments thereof, and from the claims.

Compounds

The compounds of the invention may be prepared using any methods known to those skilled in the art and/or using the methods exemplified herein.

In some embodiments, the compound is a compound of Formula I:

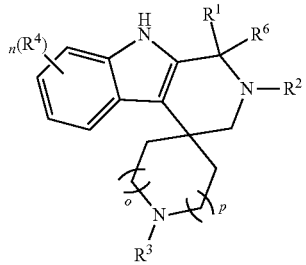

Formula I wherein n is 1, 2, 3, or 4;
o and p are independently 0, 1, or 2;
$R^1$ and $R^6$ are, independently, selected from the group consisting of H and $C_1$-$C_6$ alkyl, wherein the alkyl group is optionally substituted with at least one independently selected from the group consisting of $C_1$-$C_6$ alkyl, $C_3$-$C_8$ cycloalkyl, halo, —OH, $C_1$-$C_6$ alkoxy, $C_1$-$C_6$ haloalkoxy, —$NH_2$, —NHC(=O)($C_1$-$C_6$ alkyl), —NH($C_1$-$C_6$ alkyl) and —N($C_1$-$C_6$ alkyl)($C_1$-$C_6$ alkyl);
$R^2$ is hydrogen, $C_1$-$C_6$ alkyl, $C_1$-$C_6$ perfluoroalkyl, $C_6$-$C_{10}$ aryl $C_1$-$C_6$ alkyl, $C_1$-$C_6$ heteroaryl $C_1$-$C_6$ alkyl, $C_2$-$C_9$ heterocyclyl $C_1$-$C_6$ alkyl, or $C_3$-$C_{10}$ carbocyclyl $C_1$-$C_6$ alkyl, wherein the alkyl group is optionally substituted with at least one independently selected from the group consisting of $C_1$-$C_6$ alkyl, $C_3$-$C_8$ cycloalkyl, halo, —OH, $C_1$-$C_6$ alkoxy, $C_1$-$C_6$ haloalkoxy, —$NH_2$, —NHC(=O)($C_1$-$C_6$ alkyl), —NH($C_1$-$C_6$ alkyl) and —N($C_1$-$C_6$ alkyl)($C_1$-$C_6$ alkyl) and the aryl, heteroaryl, heterocyclyl, or carbocyclyl group is optionally substituted with at least one independently selected from the group consisting of $C_1$-$C_6$ alkyl, $C_1$-$C_6$ haloalkyl, $C_3$-$C_8$ cycloalkyl, halo, —OH, $C_1$-$C_6$ alkoxy, $C_1$-$C_6$ haloalkoxy, —$NH_2$, —NH($C_1$-$C_6$ alkyl), —N($C_1$-$C_6$ alkyl)($C_1$-$C_6$ alkyl), —$NO_2$, —C(=O)OH, —C(=O)OR, and —NHC(=O)($C_1$-$C_6$ alkyl);
$R^3$ is selected from the group consisting of H, $C_1$-$C_6$ alkyl, $C_2$-$C_9$ heteroaryl, $C_6$-$C_{10}$ aryl $C_1$-$C_6$ alkyl, $C_1$-$C_6$ heteroaryl $C_1$-$C_6$ alkyl, $C_2$-$C_9$ heterocyclyl $C_1$-$C_6$ alkyl, $C_2$-$C_9$ heteroaryl $C_1$-$C_6$ alkyl, or $C_3$-$C_{10}$ carbocyclyl $C_1$-$C_6$ alkyl, —S(=O)$_2$R, —C(=O)R, —C(=O)OR, —S(=O)$_2$NHR and —C(=O)NR$_2$, wherein the alkyl group is optionally substituted with at least one independently selected from the group consisting of $C_1$-$C_6$ alkyl, $C_3$-$C_8$ cycloalkyl, halo, —OH, $C_1$-$C_6$ alkoxy, $C_1$-$C_6$ haloalkoxy, —$NH_2$, —NHC(=O)($C_1$-$C_6$ alkyl), —NH($C_1$-$C_6$ alkyl) and —N($C_1$-$C_6$ alkyl)($C_1$-$C_6$ alkyl) and the aryl, heteroaryl, heterocyclyl, or carbocyclyl group is optionally substituted with at least one independently selected from the group consisting of $C_1$-$C_6$ alkyl, $C_1$-$C_6$ haloalkyl, $C_3$-$C_8$ cycloalkyl, halo, —OH, $C_1$-$C_6$ alkoxy, $C_1$-$C_6$ haloalkoxy, —$NH_2$, —NH($C_1$-$C_6$ alkyl), —N($C_1$-$C_6$ alkyl)($C_1$-$C_6$ alkyl), —$NO_2$, —C(=O)OH, —C(=O)OR, and —NHC(=O)($C_1$-$C_6$ alkyl);
each occurrence of $R^4$ is independently selected from the group consisting of $C_1$-$C_6$ alkyl, $C_1$-$C_6$ haloalkyl, $C_3$-$C_8$ cycloalkyl, halo, —OH, $C_1$-$C_6$ alkoxy, $C_1$-$C_6$ haloalkoxy, —$NH_2$, —NH($C_1$-$C_6$ alkyl), —N($C_1$-$C_6$ alkyl)($C_1$-$C_6$ alkyl), —$NO_2$, —C(=O)OH, —C(=O)OR, and —NHC(=O)($C_1$-$C_6$ alkyl); and
each R is, independently, selected from the group consisting of hydrogen, $C_1$-$C_6$ alkyl, $C_1$-$C_6$ heteroaryl, $C_6$-$C_{10}$ aryl, $C_3$-$C_8$ cycloalkyl, $C_2$-$C_9$ heterocyclyl, $C_6$-$C_{10}$ aryl $C_1$-$C_6$ alkyl, $C_1$-$C_6$ heteroaryl $C_1$-$C_6$ alkyl, wherein the alkyl, cycloalkyl, aryl, heteroaryl, or heterocyclyl group is optionally substituted with at least one independently selected from the group consisting of $C_1$-$C_6$ alkyl, —OH, —($C_1$-$C_6$ alkoxy), halo, —$NH_2$, —NHC(=O)($C_1$-$C_6$ alkyl), —NH($C_1$-$C_6$ alkyl) and —N($C_1$-$C_6$ alkyl)($C_1$-$C_6$ alkyl). In some embodiments, $R^3$ may be selected from the group consisting of C(=O)$R^C$, and —C(=O)N($R^A$)$_2$; where $R^A$ is independently selected at each occurrence from hydrogen or a $C_1$-$C_6$ linear or branched alkyl; and $R^C$ is a saturated $C_3$-$C_8$ cycloalkyl. In some embodiments, $R^3$ is —C(=O)$R^C$ and $R^C$ is a $C_4$-$C_5$ cycloalkyl. In some embodiments, $R^3$ is —C(=O)NH$R^A$. In some embodiments, $R^3$ may be selected from the group consisting of H, —S(=O)$_2$R, —C(=O)R, —S(=O)$_2$NHR and —C(=O)NHR, wherein R is independently selected at each occurrence from the group consisting of $R^A$, $R^C$ $C_1$-$C_6$ alkyl and $C_3$-$C_8$ cycloalkyl, wherein the alkyl or cycloalkyl group is optionally substituted with at least one independently selected from the group consisting of $C_1$-$C_6$ alkyl, —OH, —($C_1$-$C_6$ alkoxy), halo, —$NH_2$, —NHC(=O)($C_1$-$C_6$ alkyl), —NH($C_1$-$C_6$ alkyl) and —N($C_1$-$C_6$ alkyl)($C_1$-$C_6$ alkyl). In some embodiments, $R^2$ is optionally substituted benzyl (e.g., fluorobenzyl, chlorobenzyl, chlorofluorobenzyl, etc.). In some embodiments, $R^2$ is fluorobenzyl (e.g., 2-fluorobenzyl, 3-fluorobenzyl, 4-fluorobenzyl, 3,4-difluorobenzyl, 3,5-difluorobenzyl, 2,3-difluorobenzyl, 2,5-difluorobenzyl, 2,4-difluorobenzyl, 2,6-difluorobenzyl, 2,3,4,-trifluorobenzyl, 2,3,5,-trifluorobenzyl, perfluorobenzyl, etc.) or chlorobenzyl (e.g., 2-chlorobenzyl, 3-chlorobenzyl, 4-chlorobenzyl, 3,4-dichlorobenzyl, 3,5-chlorobenzyl, 2,3-dichlorobenzyl, 2,5-dichlorobenzyl, 2,4-dichlorobenzyl, 2,6-dichlorobenzyl, 2,3,4,-trichlorobenzyl, 2,3,5,-trichlorobenzyl, perchlorobenzyl, etc.). In some embodiments, $R^1$ and $R^6$ are independently selected from hydrogen, hydroxymethyl, hydroxyethyl, or hydroxypropyl. In some embodiments, one of $R^1$ or $R^6$ is hydrogen. In some embodiments, one of $R^1$ or $R^6$ is hydrogen and the other is hydroxymethyl.

In some embodiments, $R^1$ is —(CH$_2$)$_q$X$R^7$, wherein q is 1, 2, 3, 4, 5, or 6, X is absent (i.e., it is a bond), O, or NR$^8$, $R^7$ is hydrogen, $C_1$-$C_6$ alkyl, $C_1$-$C_6$ heteroalkyl, $C_1$-$C_6$ perfluoroalkyl, $C_1$-$C_6$ acyl, $C_6$-$C_{10}$ aryl $C_1$-$C_6$ alkyl, an O- or N-protecting group, or $R^7$ and $R^8$ combine with the carbon atoms to which they are attached to form a 5-8 membered heterocycle, and $R^8$ is hydrogen or $C_1$-$C_6$ alkyl.

In some embodiments, $R^6$ is hydrogen or $C_1$-$C_6$ alkyl.

In some embodiments, $R^1$ is selected from the group consisting of H and $C_1$-$C_6$ alkyl, wherein the alkyl group is optionally substituted with at least one independently selected from the group consisting of $C_1$-$C_6$ alkyl, $C_3$-$C_8$ cycloalkyl, halo, —OH, $C_1$-$C_6$ alkoxy, $C_1$-$C_6$ haloalkoxy, —$NH_2$, —NHC(=O)($C_1$-$C_6$ alkyl), —NH($C_1$-$C_6$ alkyl) and —N($C_1$-$C_6$ alkyl)($C_1$-$C_6$ alkyl) and $R^6$ is hydrogen.

In some embodiments, $R^2$ is (CH$_2$)$_m$$R^5$, wherein m is 1, 2 or 3, and wherein $R^5$ is selected from the group consisting of aryl and heteroaryl, wherein the aryl or heteroaryl group is optionally substituted with at least one independently selected from the group consisting of $C_1$-$C_6$ alkyl, $C_1$-$C_6$ haloalkyl, $C_3$-$C_8$ cycloalkyl, halo, —OH, $C_1$-$C_6$ alkoxy, $C_1$-$C_6$ haloalkoxy, —$NH_2$, —NH($C_1$-$C_6$ alkyl), —N($C_1$-$C_6$ alkyl)($C_1$-$C_6$ alkyl), —$NO_2$, —C(=O)OH, —C(=O)OR, and —NHC(=O)($C_1$-$C_6$ alkyl).

In some embodiments, $R^3$ is selected from the group consisting of H, —S(=O)$_2$R, —C(=O)R, —S(=O)$_2$NHR and —C(=O)NHR; and R is selected from the group consisting of $C_1$-$C_6$ alkyl and $C_3$-$C_8$ cycloalkyl, wherein the alkyl or cycloalkyl group is optionally substituted with at least one independently selected from the group consisting of $C_1$-$C_6$ alkyl, —OH, —($C_1$-$C_6$ alkoxy), halo, —$NH_2$, —NHC(=O)($C_1$-$C_6$ alkyl), —NH($C_1$-$C_6$ alkyl) and —N($C_1$-$C_6$ alkyl)($C_1$-$C_6$ alkyl).

In some embodiments, each occurrence of $R^4$ is independently selected from the group consisting of $C_1$-$C_6$ alkyl, $C_1$-$C_6$ haloalkyl, $C_3$-$C_8$ cycloalkyl, halo, —OH, $C_1$-$C_6$ alkoxy, $C_1$-$C_6$ haloalkoxy, —$NH_2$, —NH($C_1$-$C_6$ alkyl), —N($C_1$-$C_6$ alkyl)($C_1$-$C_6$ alkyl), —$NO_2$, —C(=O)OH, —C(=O)OR, and —NHC(=O)($C_1$-$C_6$ alkyl).

In some embodiments, o and p are 1. In some embodiments, the compound has the structure of Formula IA:

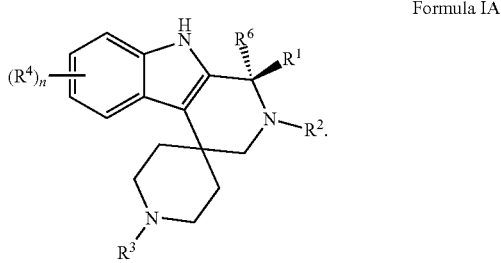

Formula IA

In some embodiments, the compound has the structure of Formula IB:

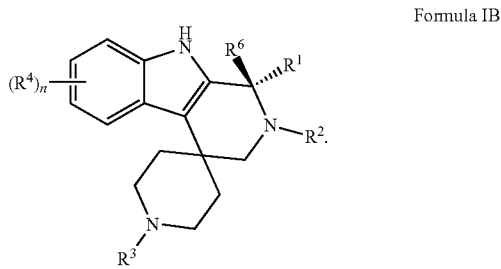

Formula IB

In some embodiments $R^6$ is hydrogen. In certain embodiments, the compound of formula (IA) is a mixture of compounds having Formulas IA and IB.

In one aspect, the invention provides a compound of formula II, or a salt, solvate or stereoisomer thereof:

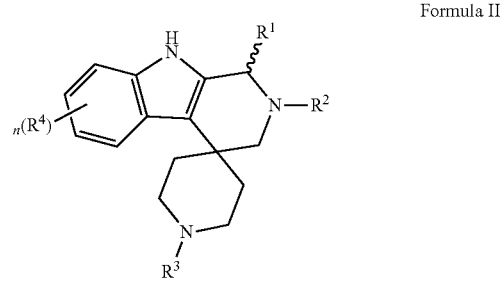

Formula II wherein $R^1$ is selected from the group consisting of H and $C_1$-$C_6$ alkyl, wherein the alkyl group is optionally substituted with at least one independently selected from the group consisting of $C_1$-$C_6$ alkyl, $C_3$-$C_8$ cycloalkyl, halo, —OH, $C_1$-$C_6$ alkoxy, $C_1$-$C_6$ haloalkoxy, —$NH_2$, —NHC(=O)($C_1$-$C_6$ alkyl), —NH($C_1$-$C_6$ alkyl) and —N($C_1$-$C_6$ alkyl)($C_1$-$C_6$ alkyl);

$R^2$ is $(CH_2)_m R^5$, wherein m is 1, 2 or 3, and wherein $R^5$ is selected from the group consisting of aryl and heteroaryl, wherein the aryl or heteroaryl group is optionally substituted with at least one independently selected from the group consisting of $C_1$-$C_6$ alkyl, $C_1$-$C_6$ haloalkyl, $C_3$-$C_8$ cycloalkyl, halo, —OH, $C_1$-$C_6$ alkoxy, $C_1$-$C_6$ haloalkoxy, —$NH_2$, —NH($C_1$-$C_6$ alkyl), —N($C_1$-$C_6$ alkyl)($C_1$-$C_6$ alkyl), —$NO_2$, —C(=O)OH, —C(=O)OR, and —NHC(=O)($C_1$-$C_6$ alkyl);

$R^3$ is selected from the group consisting of H, —S(=O)$_2$R, —C(=O)R, —S(=O)$_2$NHR and —C(=O)NHR, wherein R is independently selected at each occurrence from the group consisting of $R^A$, $R^C$ $C_1$-$C_6$ alkyl and $C_3$-$C_8$ cycloalkyl, wherein the alkyl or cycloalkyl group is optionally substituted with at least one independently selected from the group consisting of $C_1$-$C_6$ alkyl, —OH, —($C_1$-$C_6$ alkoxy), halo, —$NH_2$, —NHC(=O)($C_1$-$C_6$ alkyl), —NH($C_1$-$C_6$ alkyl) and —N($C_1$-$C_6$ alkyl)($C_1$-$C_6$ alkyl).

each occurrence of $R^4$ is independently selected from the group consisting of $C_1$-$C_6$ alkyl, $C_1$-$C_6$ haloalkyl, $C_3$-$C_8$ cycloalkyl, halo, —OH, $C_1$-$C_6$ alkoxy, $C_1$-$C_6$ haloalkoxy, —$NH_2$, —NH($C_1$-$C_6$ alkyl), —N($C_1$-$C_6$ alkyl)($C_1$-$C_6$ alkyl), —$NO_2$, —C(=O)OH, —C(=O)OR, and —NHC(=O)($C_1$-$C_6$ alkyl); and n is 0, 1, 2, 3 or 4.

In certain embodiments, the compound of formula (II) is a compound of formula (IIA), or a salt or solvate thereof:

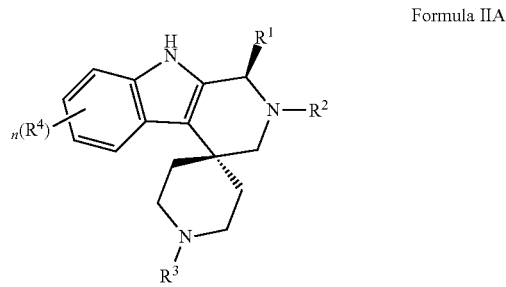

Formula IIA

In certain embodiments, the compound of formula (II) is a compound of formula (IIB), or a salt or solvate thereof:

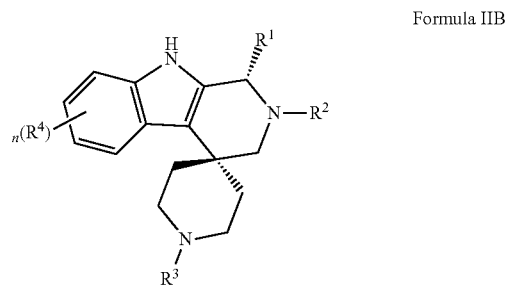

Formula IIB

In certain embodiments, the compound of formula (II) is a mixture of a compound of formula (IIA) and a compound of formula (IIB), or a salt or solvate thereof.

In certain embodiments, $R^1$ is selected from the group consisting of H and $C_1$-$C_6$ alkyl, wherein the alkyl group is optionally substituted with at least one independently selected from the group consisting of $C_1$-$C_6$ alkyl, halo, —OH, $C_1$-$C_6$ alkoxy, and $C_1$-$C_6$ haloalkoxy. In other embodiments, $R^1$ is selected from the group consisting of H and $C_1$-$C_6$ alkyl, wherein the alkyl group is optionally substituted with at least one independently selected from the group consisting of halo, —OH, $C_1$-$C_6$ alkoxy, and $C_1$-$C_6$ haloalkoxy. In yet other embodiments, $R^1$ is selected from the group consisting of H and —$CH_2OH$.

In certain embodiments, m is 1 or 2. In other embodiments, m is 1.

In certain embodiments, $R^5$ is aryl optionally substituted with at least one independently selected from the group consisting of $C_1$-$C_6$ alkyl, $C_1$-$C_6$ haloalkyl, $C_3$-$C_8$ cycloalkyl, halo, —OH, $C_1$-$C_6$ alkoxy, $C_1$-$C_6$ haloalkoxy, —NH$_2$, —NH($C_1$-$C_6$ alkyl), —N($C_1$-$C_6$ alkyl)($C_1$-$C_6$ alkyl), —NO$_2$, —C(=O)OH, —C(=O)OR, and —NHC(=O)($C_1$-$C_6$ alkyl). In other embodiments, $R^2$ is CH$_2R^5$, wherein $R^5$ is aryl optionally substituted with at least one independently selected from the group consisting of $C_1$-$C_6$ alkyl, $C_1$-$C_6$ haloalkyl, $C_3$-$C_8$ cycloalkyl, halo, —OH, $C_1$-$C_6$ alkoxy, and $C_1$-$C_6$ haloalkoxy. In yet other embodiments, $R^5$ is selected from the group consisting of 2-fluorophenyl, 3-fluorophenyl, 4-fluorophenyl, 2-chlorophenyl, 3-chlorophenyl, 4-chlorophenyl, 2,5-difluorophenyl, 2,5-dichlorophenyl, 2-chloro-5-fluorophenyl, and 5-chloro-2-fluorophenyl.

In certain embodiments, $R^3$ is selected from the group consisting of H, —S(=O)$_2$R, —C(=O)R, —S(=O)$_2$NHR and —C(=O)NHR, wherein R is selected from the group consisting of $C_1$-$C_6$ alkyl and $C_3$-$C_8$ cycloalkyl.

In certain embodiments, each occurrence of $R^4$ is independently selected from the group consisting of $C_1$-$C_6$ alkyl, $C_1$-$C_6$ haloalkyl, $C_3$-$C_8$ cycloalkyl, halo, —OH, $C_1$-$C_6$ alkoxy and $C_1$-$C_6$ haloalkoxy.

In certain embodiments, n is 0, 1 or 2. In other embodiments, n is 1, and $R^4$ is at the 7' position of compound (II).

For purely exemplary reasons, numbering of the ring system in formula (II) is illustrated herein:

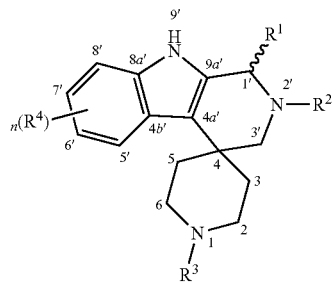

Non-limiting examples of compounds of the invention comprise:

(S)-cyclobutyl(2'-(2-fluorobenzyl)-1'-(hydroxymethyl)-7'-methoxy-1',2',3',9'-tetrahydrospiro[piperidine-4,4'-pyrido[3,4-b]indol]-1-yl)methanone (also denoted as Compound 5):

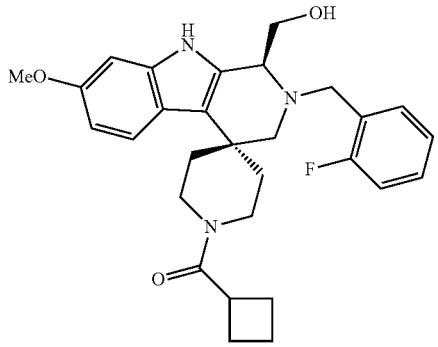

(R)-cyclobutyl(2'-(2-fluorobenzyl)-1'-(hydroxymethyl)-7'-methoxy-1',2',3',9'-tetrahydrospiro[piperidine-4,4'-pyrido[3,4-b]indol]-1-yl)methanone (also denoted as Compound 6):

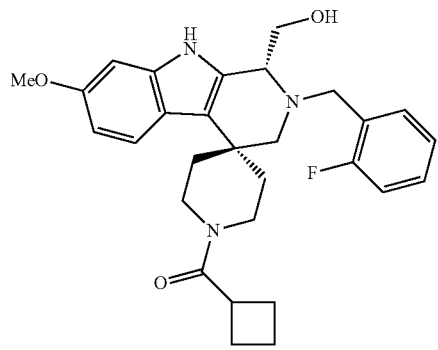

cyclobutyl(2'-(2-fluorobenzyl)-7'-methoxy-1',2',3',9'-tetrahydrospiro[piperidine-4,4'-pyrido[3,4-b]indol]-1-yl)methanone (also denoted as Compound 11);

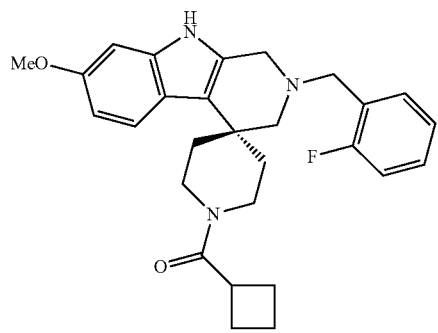

(S)-(2'-benzyl-1'-(hydroxymethyl)-7'-methoxy-1',2',3',9'-tetrahydrospiro[piperidine-4,4'-pyrido[3,4-b]indol]-1-yl)(cyclobutyl)methanone (also denoted as Compound 12):

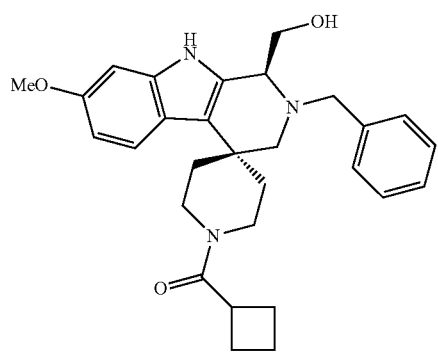

(S)-cyclobutyl(2'-(3-fluorobenzyl)-1'-(hydroxymethyl)-7'-methoxy-1',2',3',9'-tetrahydrospiro[piperidine-4,4'-pyrido[3,4-b]indol]-1-yl)methanone (also denoted as Compound 13):

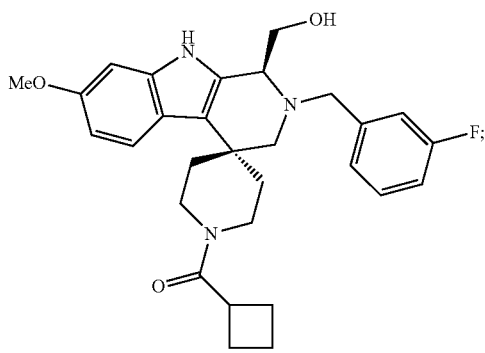

(S)-cyclobutyl(2'-(4-fluorobenzyl)-1'-(hydroxymethyl)-7'-methoxy-1',2',3',9'-tetrahydrospiro[piperidine-4,4'-pyrido[3,4-b]indol]-1-yl)methanone (also denoted as Compound 14):

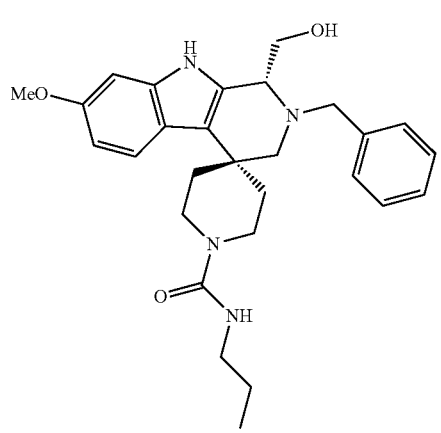

(S)-2'-benzyl-1'-(hydroxymethyl)-7'-methoxy-N-propyl-1',2',3',9'-tetrahydrospiro[piperidine-4,4'-pyrido[3,4-b]indole]-1-carboxamide (also denoted as Compound 10):

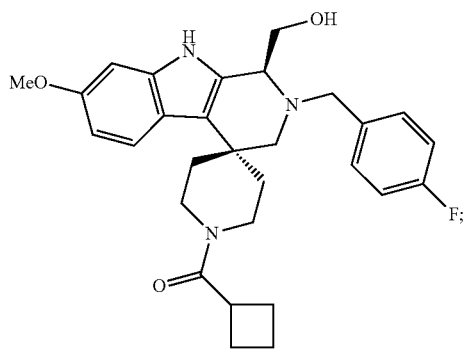

(S)-(2'-(2-chlorobenzyl)-1'-(hydroxymethyl)-7'-methoxy-1',2',3',9'-tetrahydrospiro[piperidine-4,4'-pyrido[3,4-b]indol]-1-yl)(cyclobutyl)methanone (also denoted as Compound 15):

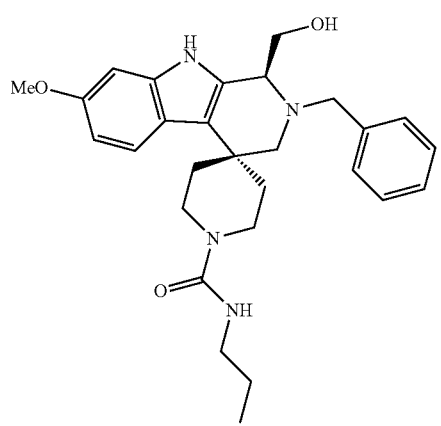

(S)-cyclobutyl(2'-(2,5-difluorobenzyl)-1'-(hydroxymethyl)-7'-methoxy-1',2',3',9'-tetrahydrospiro[piperidine-4,4'-pyrido[3,4-b]indol]-1-yl)methanone (also denoted as Compound 9):

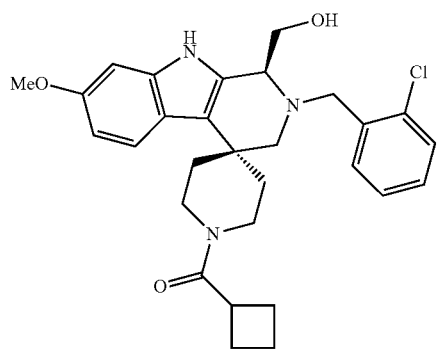

(R)-2'-benzyl-1'-(hydroxymethyl)-7'-methoxy-N-propyl-1',2',3',9'-tetrahydrospiro[piperidine-4,4'-pyrido[3,4-b]indole]-1-carboxamide (also denoted as Compound 2):

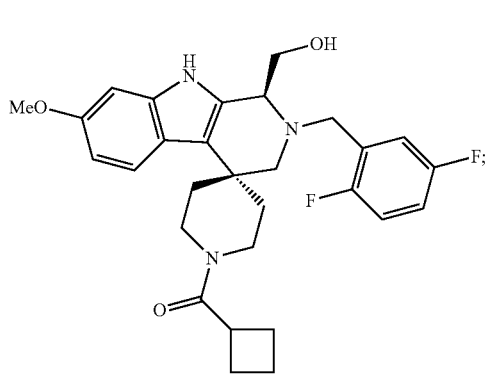

(S)-cyclopentyl(2'-(2-fluorobenzyl)-1'-(hydroxymethyl)-7'-methoxy-1',2',3',9'-tetrahydrospiro[piperidine-4,4'-pyrido[3,4-b]indol]-1-yl)methanone (also denoted as Compound 4):

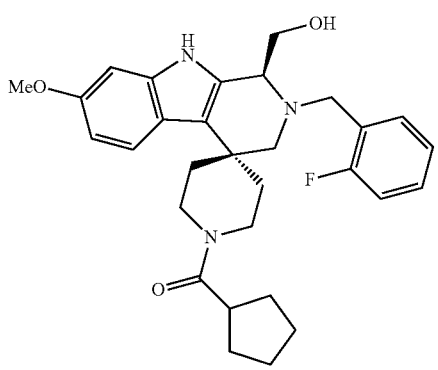

(R)-cyclopentyl(2'-(2-fluorobenzyl)-1'-(hydroxymethyl)-7'-methoxy-1',2',3',9'-tetrahydrospiro[piperidine-4,4'-pyrido[3,4-b]indol]-1-yl)methanone (also denoted as Compound 7):

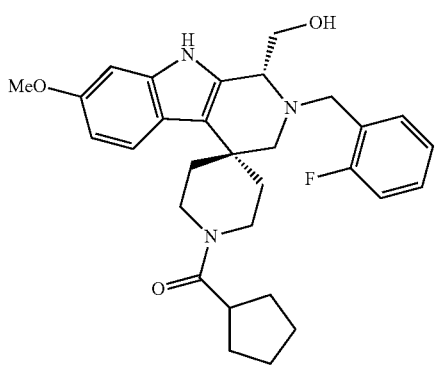

N-(2-aminophenyl)-4-(((((13S,15R,5R,11R)-35-(dimethylamino)-15-(hydroxymethyl)-5-methyl-2-oxo-4,10-dioxa-1(1,3)-pyrrolidina-3(1,2)-benzenacycloundecaphane-11-yl)methyl)(methyl)amino)methyl)benzamide (also denoted as Compound 8):

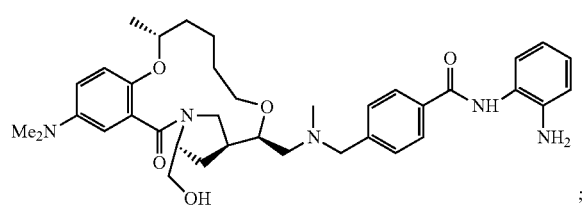 [SMILES: C[C@@H]1CCCCO[C@@H](CN(C)Cc2ccc(C(=O)Nc3ccccc3N)cc2)[C@H]2C[C@@H](CO)N(C2)C(=O)c2cc(N(C)C)ccc2O1]

N-(2-aminophenyl)-4-(((((2S,3R)-5-((R)-1-hydroxypropan-2-yl)-3-methyl-6-oxo-10-(4-(thiazol-2-yl)benzamido)-3,4,5,6-tetrahydro-2H-benzo[b][1,5]oxazocin-2-yl)methyl)(methyl)amino)methyl)benzamide (also denoted as Compound 1):

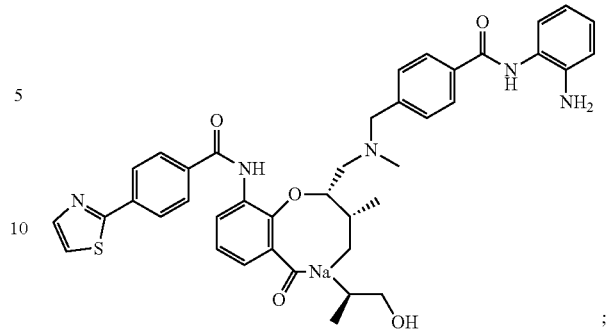

N-(((2S,3R)-8-(3-cyclohexylureido)-5-((R)-1-hydroxypropan-2-yl)-3-methyl-6-oxo-3,4,5,6-tetrahydro-2H-benzo[b][1,5]oxazocin-2-yl)methyl)-N-methylthiophene-2-sulfonamide (also denoted as Compound 3):

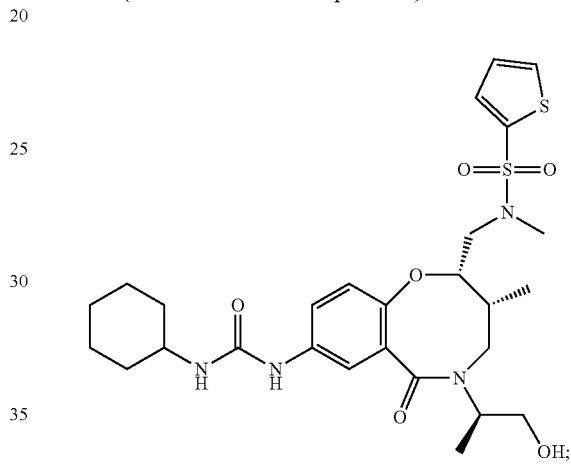

or a salt or solvate thereof.

It will be understood that in the event of any inconsistency between a chemical name and formula, both compounds with the indicated chemical name and compounds with the indicated chemical structure will be considered as embraced by the invention.

The compounds of the invention may possess one or more stereocenters, and each stereocenter may exist independently in either the (R) or (S) configuration. In one embodiment, compounds described herein are present in optically active or racemic forms. The compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomers is utilized as the therapeutic compounds described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compounds of the invention, as well as metabolites and active metabolites of these compounds having the same type of activity. Solvates include water, ether (e.g., tetrahydrofuran, or methyl tert-butyl ether) or alcohol (e.g., ethanol) solvates, acetates and the like. In certain embodiments, the compounds described herein exist in solvated forms with pharmaceutically acceptable solvents such as water, and ethanol. In another embodiment, the compounds described herein exist in unsolvated form.

In one embodiment, the compounds of the invention may exist as tautomers. All tautomers are included within the scope of the compounds recited herein.

In one embodiment, compounds described herein are prepared as prodrugs. A "prodrug" is an agent converted into the parent drug in vivo. In one embodiment, upon in vivo administration, a prodrug is chemically converted to the biologically, pharmaceutically or therapeutically active form of the compound. In another embodiment, a prodrug is enzymatically metabolized by one or more steps or processes to the biologically, pharmaceutically or therapeutically active form of the compound.

In one embodiment, sites on, for example, the aromatic ring portion of compounds of the invention are susceptible to various metabolic reactions. Incorporation of appropriate substituents on the aromatic ring structures may reduce, minimize or eliminate this metabolic pathway. In one embodiment, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In certain embodiments, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}$C, $^{18}$F, $^{15}$O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

Synthesis

The compounds can be prepared from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds described herein.

Synthetic chemistry transformations (including protecting group methodologies) useful in synthesizing the compounds described herein are known in the art and include, for example, those such as described in R. C. Larock, *Comprehensive Organic Transformations*, 2d. ed., Wiley-VCH Publishers (1999); P. G. M. Wuts and T. W. Greene, *Protective Groups in Organic Synthesis*, 4th Ed., John Wiley and Sons (2007); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy (FT-IR), spectrophotometry (e.g., UV-visible), or mass spectrometry (MS), or by chromatography such as high performance liquid chromatography (HPLC) or thin layer chromatography (TLC).

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of compounds can be carried out by any of numerous methods known in the art. An example method includes preparation of the Mosher's ester or amide derivative of the corresponding alcohol or amine, respectively. The absolute configuration of the ester or amide is then determined by proton and/or $^{19}$F NMR spectroscopy. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent compositions can be determined by one skilled in the art.

In one embodiment, the compounds described herein are labeled by other means, including, but not limited to, the use of chromophores or fluorescent moieties, bioluminescent labels, or chemiluminescent labels.

The invention further includes a pharmaceutical composition comprising at least one compound of the invention and a pharmaceutically acceptable carrier.

In certain embodiments, the pharmaceutical composition further comprises at least one additional agent that is useful to treat the diseases or disorders contemplated herein. In certain embodiments, the compound of the invention and the additional agent are co-formulated in the composition.

Salts

The compounds described herein may form salts with acids or bases, and such salts are included in the present invention. In certain embodiments, the salts are pharmaceutically acceptable salts. The term "salts" embraces addition salts of free acids or bases that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts of compounds of the invention may be prepared from an inorganic acid or an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

Methods

The invention provides a method of treating or preventing a synovial sarcoma in a subject, the method comprising administering to the subject in need thereof a therapeutically effective amount of at least one compound of the present invention.

In certain embodiments, the subject is further administered at least one additional anticancer agent that is a FDA-approved cytotoxic and/or chemotherapy agent, such as an agent selected from the group consisting of doxorubicin and ifosfamide. In some embodiments, the at least one additional agent and the at least one compound are co-administered to the subject. In some embodiments, the at least one additional agent and the at least one compound are co-formulated. In some embodiments, the subject further receives radiotherapy to treat or prevent the synovial sarcoma. In some embodiments, the at least one compound is administered to the subject by at least one route selected from the group consisting of nasal, inhalational, topical, oral, buccal, rectal, pleural, peritoneal, vaginal, intramuscular, subcutaneous, transdermal, epidural, intrathecal and intravenous routes. In some embodiments, the subject is human.

The invention further provides a method of monitoring and/or detecting levels of BAF47 in a cell. The method is based in part on the development of a construct wherein BAF47 is fused to luciferase reporter protein.

Formulations/Administration

The compositions of the present invention may contain a pharmaceutical acceptable carrier, excipient and/or diluent, and may be administered by a suitable method to a subject. The compositions of the present invention may be formulated in various forms, including oral dosage forms or sterile injectable solutions, according to any conventional method known in the art. In other embodiments, the compositions may also be used as an inhalation-type drug delivery system. In yet other embodiments, the compositions of the invention may be formulated for injectable solutions.

The compositions may be formulated as powders, granules, tablets, capsules, suspensions, emulsions, syrup, aerosol, preparations for external application, suppositories and sterile injectable solutions. Suitable formulations known in the art are disclosed in, for example, Remington's Pharmaceutical Science (Mack Publishing Company, Easton Pa.). Carriers, excipients and diluents that may be contained in the composition of the present invention include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propyl hydroxylbenzoate, talc, magnesium stearate or mineral oil.

Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g., BHT), buffering agents (for example phosphate or citrate buffers), and effervescent agents such as citrate/bicarbonate mixtures. Capsule formulations may be of the hard gelatin or soft gelatin variety and can contain the active component in solid, semi-solid, or liquid form. Gelatin capsules can be formed from animal gelatin or synthetic or plant derived equivalents thereof. The solid dosage forms (e.g., tablets, capsules etc.) can be coated or uncoated, but typically have a coating, for example a protective film coating (e.g. a wax or varnish) or a release controlling coating. The coating (e.g., a EUDRAGIT® type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum. Alternatively or additionally, the coating can be used as a taste masking agent to mask unpleasant tastes such as bitter tasting drugs. The coating may contain sugar or other agents that assist in masking unpleasant tastes. Instead of, or in addition to, a coating, the active agent can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g., a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art. The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions. Each tablet, capsule, caplet, pill, etc. can be a single dose, with a dose, for example, as herein discussed, or a dose can be two or more tablets, capsules, caplets, pills, and so forth; for example if a tablet, capsule and so forth is 125 mg and the dose is 250 mg, the patient may take two tablets, capsules and the like, at each interval there is to administration.

The compositions of the present invention may be formulated with commonly used diluents or excipients, such as fillers, extenders, binders, wetting agents, disintegrants, or surfactants. Solid formulations for oral administration include tablets, pills, powders, granules, or capsules, and such solid formulations comprise, in addition to the composition, at least one excipient, for example, starch, calcium carbonate, sucrose, lactose or gelatin. In addition to simple excipients, lubricants such as magnesium stearate or talc may also be used. Liquid formulations for oral administration include suspensions, solutions, emulsions and syrup, and may contain various excipients, for example, wetting agents, flavoring agents, aromatics and preservatives, in addition to water and liquid paraffin, which are frequently used simple diluents.

Formulations for parenteral administration include sterilized aqueous solutions, non-aqueous solutions, suspensions, emulsions, freeze-dried preparations, and suppositories. As non-aqueous solvents or suspending agents, propylene glycol, polyethylene glycol, plant oils such as olive oil, or injectable esters such as ethyl oleate may be used. As the base of the suppositories, witepsol, Macrogol, Tween 61, cacao butter, laurin fat, or glycerogelatin may be used.

The dose of the pharmaceutical compositions of the present invention varies depending on the patient's condition and weight, the severity of the disease, the type of drug, and the route and period of administration and may be suitably selected by those skilled in the art. For certain effects, the pharmaceutical composition of the present invention may be administered at a dose of 0.01-100 mg/kg/day. The administration may be anywhere from 1 to 4 times daily, e.g., once, twice, three times or four times daily. The maximum amount administered in a 24 hour period may be up to 1500 mg. The administration may be over a course of 2 to 30 days, e.g., 3 to 21 days, such as 7, 10 or 14 days. The skilled person can adjust dosing depending on the subject's body weight and overall health condition and the purpose for administering the active agent. Repeated courses of treatment may be pursued depending on the response obtained.

The compositions of the present invention may be administered to a subject by various routes. All modes of administration are contemplated, for example, orally, rectally, mucosally (e.g., by oral or nasal inhalation), transmucosally, topically (transdermal), or by intravenous, intradermal, intramuscular, subcutaneous, intracutaneous, intrauterine, epidural or intracerebroventricular injection.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The following examples are put forth so as to provide those of ordinary skill in the art with a complete disclosure and description of how to make and use the assay, screening, and therapeutic methods of the invention, and are not intended to limit the scope of what the inventor(s) regard(s) as the invention.

EXAMPLES

The invention is now described with reference to the following Examples. These Examples are provided for the purpose of illustration only, and the invention is not limited to these Examples, but rather encompasses all variations that are evident as a result of the teachings provided herein.

Unless noted otherwise, the starting materials for the synthesis described herein were obtained from commercial sources or known synthetic procedures and were used without further purification.

Materials and Methods

Preparation of Nuclear Extracts.

All cell types were grown under standard conditions and lysed and homogenized in Buffer A (10 mM Hepes (pH 7.6), 25 mM KCl, 1 mM EDTA, 10% glycerol, 1 mM DTT, and protease inhibitors (complete mini tablets (Roche) supplemented with 1 mM PMSF) on ice. Nuclei were sedimented by centrifugation (1,000×g), resuspended in Buffer C (10 mM Hepes (pH 7.6), 3 mM $MgCl_2$, 100 mM KCl, 0.1 mM EDTA, 10% glycerol, 1 mM DTT, and protease inhibitors), and lysed by the addition of ammonium sulfate to a final concentration of 0.3 M. Soluble nuclear proteins were separated by the insoluble chromatin fraction by ultracentrifugation (100,000×g) and precipitated with 0.3 mg/ml ammonium sulfate for 20 min on ice. Protein precipitate was isolated by ultracentrifugation (100,000×g), and resuspended in IP buffer (150 mM NaCl, 50 mM Tris-HCl (pH 8.0), 1% NonidetP-40, 0.5% deoxycholate, 1 mM DTT, 1 mM PMSF with protease inhibitors) for immunoprecipitation analyses or HEMG-0 buffer (25 mM HEPES pH 7.9, 0.1 mM EDTA, 12.5 mM MgCl2, 100 mM KCl, freshly supplemented with DTT and PMSF) for glycerol gradient analyses.

Immunoprecipitation.

Nuclear extracts were resuspended in IP buffer and pre-cleared for 30 minutes at 4 degrees C. using Protein G/A Sepharose beads (GE Healthcare). The protein concentration was determined using Bradford assay and adjusted to a final volume of 250 μL at a final concentration of 1.5 mg/mL with IP buffer. Each IP was incubated with 2.5 μg of antibody overnight at 4° C. and then for 2 h with 20 μL Protein A/G Sepharose beads. The beads were washed four times at room temperature with 1 mL IP buffer and resuspended in 20 μL 2× gel loading buffer (4×LDS Buffer; Invitrogen)+DTT.

Example 1

Synthesis

Synthesis of tert-butyl 4-(aminomethyl)-4-(6-methoxy-1H-indol-3-yl)piperidine-1-carboxylate

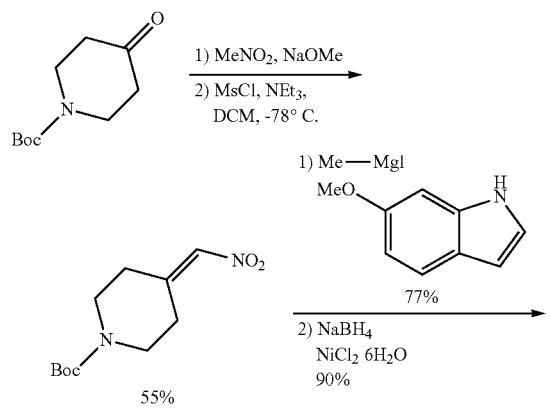

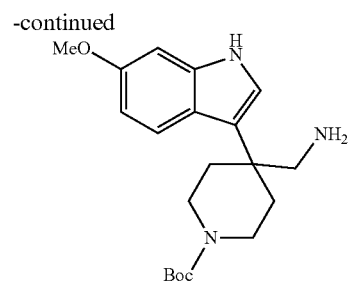

tert-butyl 4-(nitromethylene)piperidine-1-carboxylate

To a solution of 1-tert-butyloxycarbonyl-4-piperidinone ("1-Boc-4-piperidinone", 15 g, 75 mmol) in MeOH (151 mL) was added nitromethane (41 mL, 753 mmol) and sodium methanolate (2.034 g, 37.6 mmol) at room temperature. The reaction was stirred for 16 hours, then saturated $NaHCO_3$ was added and the mixture was extracted with ethyl acetate. The organic phase was separated, dried ($Na_2SO_4$), filtered and concentrated to afford crude tert-butyl 4-hydroxy-4-(nitromethyl)piperidine-1-carboxylate that was used directly in the subsequent step. To a solution of this crude material in DCM at 78° C. was added triethylamine (46 mL, 331 mmol) and methanesulfonyl chloride (18.73 mL, 241 mmol). The reaction mixture was allowed to stir at 78° C. for 30 minutes. The temperature was then increased to 20° C. for 4 hours upon which thin layer chromatographic ("TLC") analysis indicated complete reaction. The mixture was carefully poured into a cold ammonium chloride solution and extracted with dichloromethane ("DCM"). The organic phase was separated, dried over $Na_2SO_4$, filtered and concentrated. The crude material was purified by flash column chromatography eluting with EtOAc/Hexanes to give the desired compound (10 g, 55%).

tert-butyl 4-(6-methoxy-1H-indol-3-yl)-4-(nitromethyl)piperidine-1-carboxylate

To a solution of 6-methoxy-1H-indole (3.39 g, 23.03 mmol) in THF (57.6 ml) was added methylmagnesium iodide (3.0 M in $Et_2O$, 8.83 mL, 26.5 mmol) dropwise. The mixture was stirred at room temperature for 20 minutes and then cooled to 0° C. tert-butyl 4-(nitromethylene)piperidine-1-carboxylate (5.58 g, 23.03 mmol) in THF (173 mL) was then added dropwise at 0° C. The reaction mixture was warmed and stirred for 16 hours to bring the mixture to room temperature. Saturated ammonium chloride solution was then added was and the reaction was stirred at room temperature for 30 minutes. The organic components were extracted with EtOAc and washed with water and brine. The crude material was purified by flash column chromatography eluting with EtOAc/Hexanes to give the desired product (6.91 g, 77%).

tert-butyl 4-(aminomethyl)-4-(6-methoxy-1H-indol-3-yl)piperidine-1-carboxylate

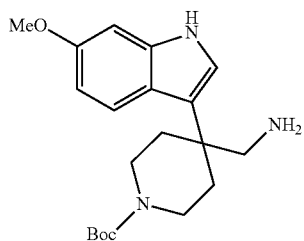 [SMILES: COc1ccc2c(C3(CN)CCN(C(=O)OC(C)(C)C)CC3)c[nH]c2c1]

To a solution of tert-butyl 4-(6-methoxy-1H-indol-3-yl)-4-(nitromethyl)piperidine-1-carboxylate (7.7 g, 19.77 mmol) in THF (316 mL) at room temperature was added $NiCl_2 \cdot 6H_2O$ (4.70 g, 19.77 mmol) and $NaBH_4$ (2.99 g, 79 mmol). The reaction was cooled to 0° C. and then MeOH (79 mL) was added very slowly (caution, vigorous reaction). The reaction was warmed to room temperature and after 3 hours, diethylenetriamine (29.9 mL, 277 mmol) was added. After a further 1 hour the reaction mixture was concentrated in vacuo. A saturated sodium bicarbonate solution was added and the organic components were extracted with EtOAc. The organic phase was separated, dried ($Na_2SO_4$), filtered and concentrated. The crude material was purified by flash column chromatography eluting with EtOAc/Hexanes to give the desired compound (6.37 g, 90%).

Synthesis of Compound 6 (i.e., (R)-(1'-hydroxymethyl) tert-2'-(2-fluorobenzyl)-7'-methoxy-1',2',3',9'-tetrahydrospiro[piperidine-4,4'-pyrido[3,4-b]indol]-1-yl)(cyclobutyl)methanone)

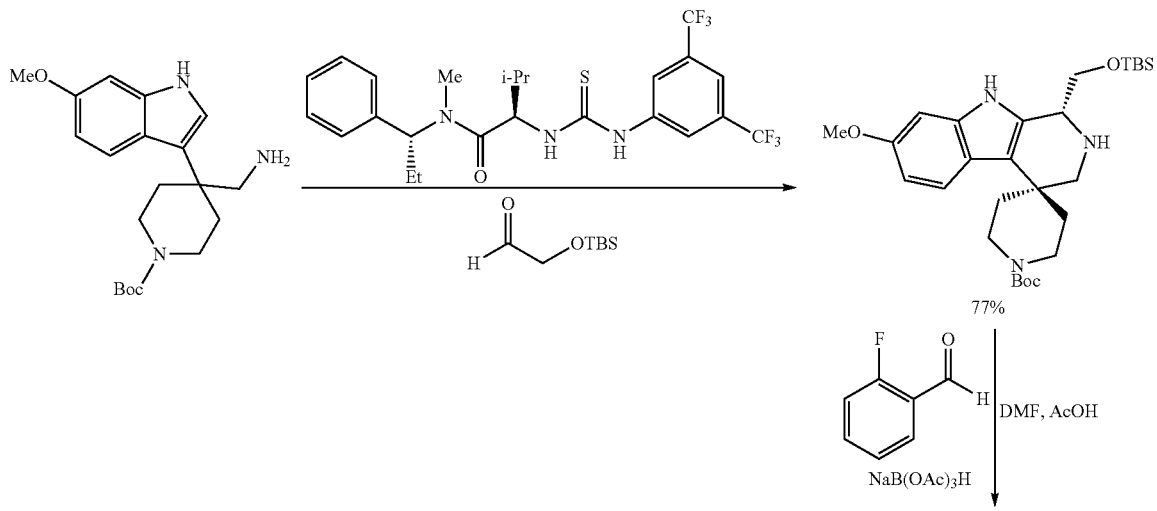

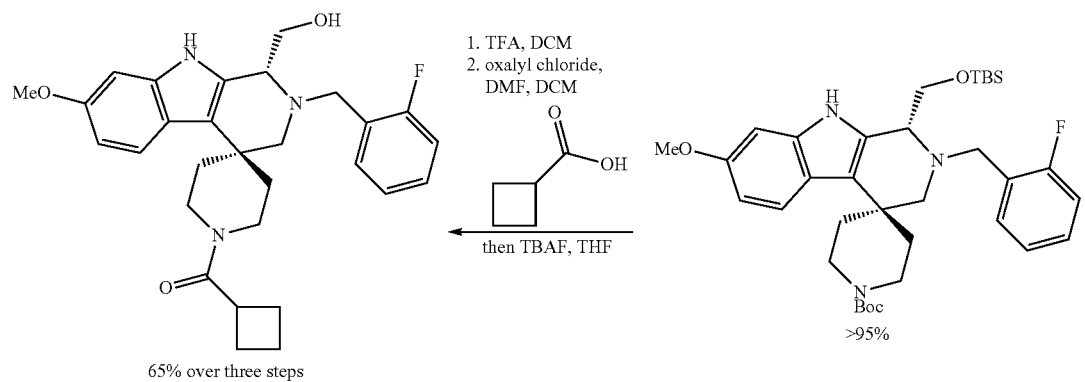

(R)-tert-butyl 1'-(((tert-butyldimethylsilyl)oxy)methyl)-7'-methoxy-1',2',3',9'-tetrahydrospiro[piperidine-4,4'-pyrido[3,4-b]indole]-1-carboxylate

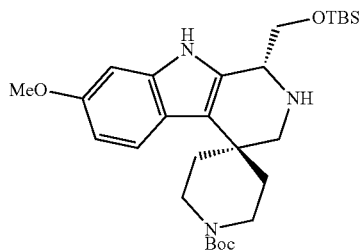

To a solution of tert-butyl 4-(aminomethyl)-4-(6-methoxy-1H-indol-3-yl)piperidine-1-carboxylate (2.61 g, 7.26 mmol) in toluene (132 mL) was added (R)-2-(3-(3,5-bis(trifluoromethyl)phenyl)thioureido)-N,3-dimethyl-N—((R)-1-phenylpropyl)butanamide (0.566 g, 1.089 mmol) at 20° C. The mixture was stirred for 10 minutes before 2-(tert-butyldimethylsilyloxy)acetaldehyde (1.519 g, 8.71 mmol) (freshly distilled) in toluene (1801 µL) was added. The above mixture was allowed to stir at −20° C. while it was monitored by liquid chromatography mass spectomectry ("LCMS") with a Waters 2795 separations module. After 89 hours additional (R)-2-(3-(3,5-bis(trifluoromethyl)phenyl)thioureido)-N,3-dimethyl-N—((R)-1-phenylpropyl)butanamide (0.283 g, 0.545 mmol) was added to the reaction mixture. After 135 hours saturated NaHCO$_3$ was added to the reaction mixture. The reaction was then warmed to room temperature and extracted with EtOAc. The organic phase was separated, dried (Na$_2$SO$_4$), filtered and concentrated. The crude material was purified by flash column chromatography eluting with EtOAc/Hexanes to give the desired compound (2.9 g, 77%). Flash chromatography was performed using 40-60 µm Silica gel (60 Å mesh) on a Teledyne Isco Combiflash Rf.

(R)-tert-butyl 1'-(((tert-butyldimethylsilyl)oxy)methyl)-2'-(2-fluorobenzyl)-7'-methoxy-1',2',3',9'-tetrahydrospiro[piperidine-4,4'-pyrido[3,4-b]indole]-1-carboxylate

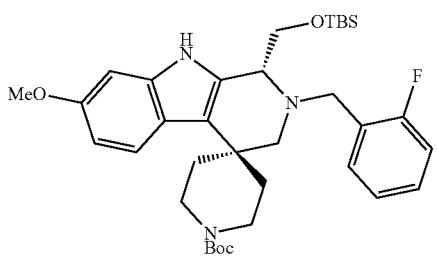

To a solution of (R)-tert-butyl 1'-(((tert-butyldimethylsilyl)oxy)methyl)-7'-methoxy-1',2',3',9'-tetrahydrospiro[piperidine-4,4'-pyrido[3,4-b]indole]-1-carboxylate (200 mg, 0.388 mmol) in 49:1 vol:vol 0.025 M DMF:AcOH was added 2-fluorobenzaldehyde (204 µL, 0.388 mmol), sodium triacetoxyborohydride (411 mg, 1.939 mmol), and 30 mg sodium sulfate. The reaction was stirred for 4 hours at ambient temperature, after which point the mixture was diluted with H$_2$O and extracted 3× with EtOAc. The organic layer was dried (Na$_2$SO$_4$), filtered and concentrated. The crude material was purified by flash column chromatography eluting with EtOAc/Hexanes to give the desired compound in quantitative yield (235 mg, >95%).

(R)-(1'-hydroxymethyl) tert-2'-(2-fluorobenzyl)-7'-methoxy-1',2',3',9'-tetrahydrospiro[piperidine-4,4'-pyrido[3,4-b]indol]-1-yl)(cyclobutyl)methanone

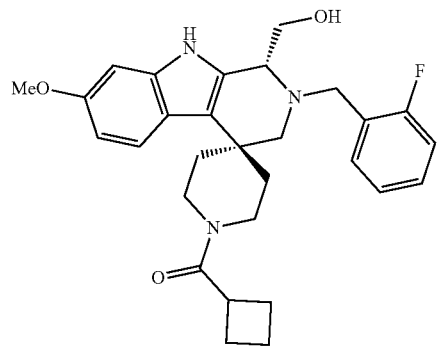

To a solution of (R)-(1'-(((tert-butyldimethylsilyl)oxy)methyl)-2'-(2-fluorobenzyl)-7'-methoxy-1',2',3',9'-tetrahydrospiro[piperidine-4,4'-pyrido[3,4-b]indol]-1-yl)(cyclobutyl) methanone (235 mg, 0.388 mmol) in DCM (0.05 M) was added trifluoroacetic acid (517 µL, 6.75 mmol). After 3 hours, the solvent was removed in vacuo to afford a crude residue. The crude residue was then dissolved in DCM (0.05 M) and Et$_3$N (270 µL, 1.94 mmol).

In a separate vial was added oxalyl chloride (414 µL, 0.466 mmol), DCM (0.05 M), and one drop of DMF. After 15 min, this solution was transferred via syringe to the crude mixture as described above and stirred at ambient temperature, after which point the combined mixture was quenched with saturated NH$_4$Cl and extracted 4× with DCM. The organic layer was dried (Na$_2$SO$_4$), filtered and concentrated.

The crude residue was then dissolved in THF (0.05 M) followed by the addition of 1.0 M TBAF in THF solution (1.164 mL, 1.164 mmol). After 3 hours stirring at ambient temperature, the mixture was quenched with saturated NH$_4$Cl and extracted 3× with EtOAc. The organic layer was dried (Na$_2$SO$_4$), filtered and concentrated. The crude material was purified by flash column chromatography eluting with MeOH/DCM to give the desired compound (125 mg, 65% over three steps).

Synthesis of Compound 5 (i.e., (S)-(1'-hydroxymethyl) tert-2'-(2-fluorobenzyl)-7'-methoxy-1',2',3',9'-tetrahydrospiro[piperidine-4,4'-pyrido[3,4-b]indol]-1-yl)(cyclobutyl)methanone)

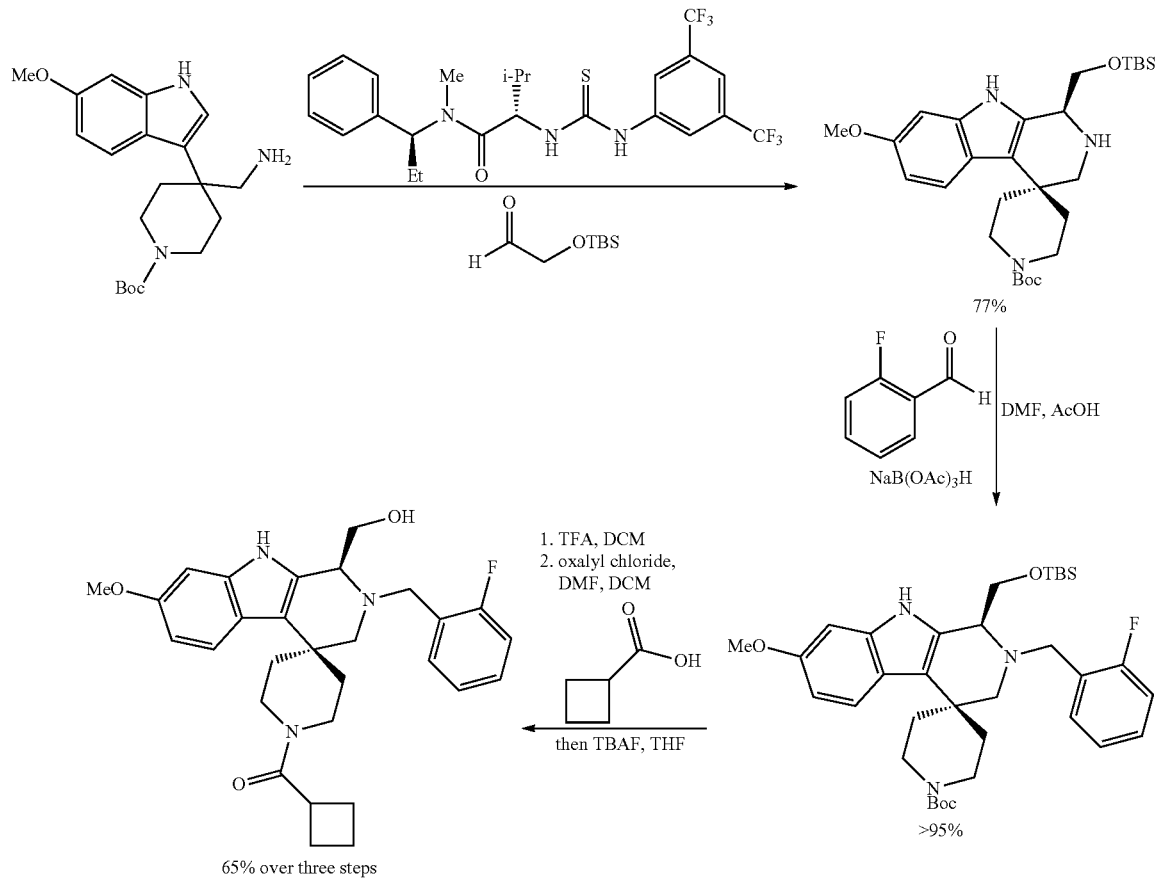

(S)-tert-butyl 1'-(((tert-butyldimethylsilyl)oxy)methyl)-7'-methoxy-1',2',3',9'-tetrahydrospiro[piperidine-4,4'-pyrido[3,4-b]indole]-1-carboxylate

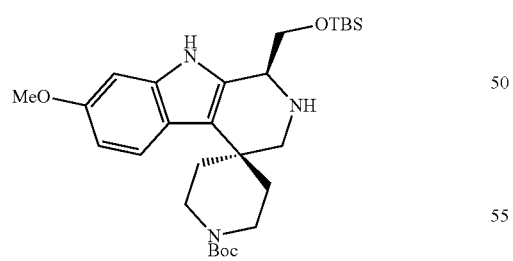

To a solution of tert-butyl 4-(aminomethyl)-4-(6-methoxy-1H-indol-3-yl)piperidine-1-carboxylate (2.61 g, 7.26 mmol) in toluene (132 mL) was added (S)-2-(3-(3,5-bis(trifluoromethyl)phenyl)thioureido)-N,3-dimethyl-N—((S)-1-phenylpropyl)butanamide (0.566 g, 1.089 mmol) at 20° C. The mixture was stirred for 10 minutes before 2-(tert-butyldimethylsilyloxy)acetaldehyde (1.519 g, 8.71 mmol) (freshly distilled) in toluene (1801 µL) was added. The above mixture was allowed to stir at −20° C. while it was monitored by LCMS. After 89 hours additional (S)-2-(3-(3,5-bis(trifluoromethyl)phenyl)thioureido)-N,3-dimethyl-N—((S)-1-phenylpropyl)butanamide (0.283 g, 0.545 mmol) was added. After 135 hours saturated NaHCO₃ was added to the reaction mixture. The reaction was warmed to room temperature and extracted with EtOAc. The organic phase was separated, dried (Na₂SO₄), filtered and concentrated. The crude material was purified by flash column chromatography eluting with EtOAc/Hexanes to give the desired compound (2.9 g, Yield: 77%).

(S)-tert-butyl 1'-(((tert-butyldimethylsilyl)oxy)methyl)-2'-(2-fluorobenzyl)-7'-methoxy-1', 2',3',9'-tetrahydrospiro[piperidine-4,4'-pyrido[3,4-b]indole]-1-carboxylate

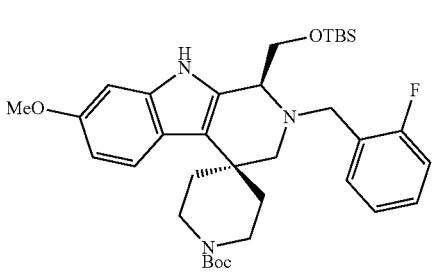

To a solution of (S)-tert-butyl 1'-(((tert-butyldimethylsilyl)oxy)methyl)-7'-methoxy-1',2',3',9'-tetrahydrospiro[piperidine-4,4'-pyrido[3,4-b]indole]-1-carboxylate (200 mg, 0.388 mmol) in 49:1 (vol:vol) DMF:AcOH (0.025 M) was added 2-fluorobenzaldehyde (204 μL, 0.388 mmol), sodium triacetoxyborohydride (411 mg, 1.939 mmol), and 30 mg sodium sulfate. The reaction was stirred for 4 hours at ambient temperature, after which point the mixture was diluted with H₂O and extracted 3× with EtOAc. The organic layer was dried (Na₂SO₄), filtered and concentrated. The crude material was purified by flash column chromatography eluting with EtOAc/Hexanes to give the desired compound in quantitative yield (235 mg, >95%).

(S)-(1'-hydroxymethyl)-2'-(2-fluorobenzyl)-7'-methoxy-1',2',3',9'-tetrahydrospiro[piperidine-4,4'-pyrido[3,4-b]indol]-1-yl)(cyclobutyl)methanone

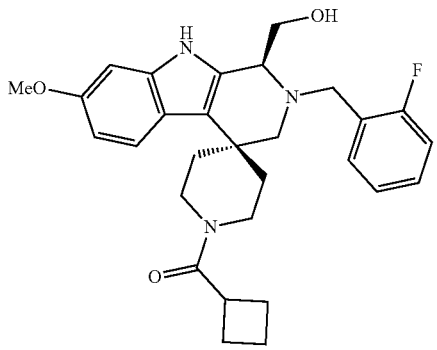

To a solution of (S)-(1'-(((tert-butyldimethylsilyl)oxy)methyl)-2'-(2-fluorobenzyl)-7'-methoxy-1',2',3',9'-tetrahydrospiro[piperidine-4,4'-pyrido[3,4-b]indol]-1-yl)(cyclobutyl)methanone (235 mg, 0.388 mmol) in DCM (0.05 M) was added trifluoroacetic acid (517 μL, 6.75 mmol). After 3 hours, the solvent was removed in vacuo to afford a crude residue. The crude residue was then dissolved in DCM (0.05 M) and Et₃N (270 μL, 1.94 mmol).

In a separate vial was added oxalyl chloride (414 μL, 0.466 mmol), DCM (0.05 M), and one drop of DMF. After 15 min, this solution was transferred via syringe to the crude mixture as described above and stirred at ambient temperature, after which point the combined mixture was quenched with saturated NH₄Cl and extracted 4× with DCM. The organic layer was dried (Na₂SO₄), filtered and concentrated.

The crude residue was then dissolved in THF (0.05 M) followed by the addition of 1.0 M TBAF in THF solution (1.164 mL, 1.164 mmol). After 3 hours stirring at ambient temperature, the mixture was quenched with saturated NH₄Cl and extracted 3× with EtOAc. The organic layer was dried (Na₂SO₄), filtered and concentrated. The crude material was purified by flash column chromatography eluting with MeOH/DCM to give the desired compound (125 mg, 65% over three steps).

Synthesis of Compound 11 (i.e., cyclobutyl(2'-(2-fluorobenzyl)-7'-methoxy-1',2',3',9'-tetrahydrospiro[piperidine-4,4'-pyrido[3,4-b]indol]-1-yl)methanone)

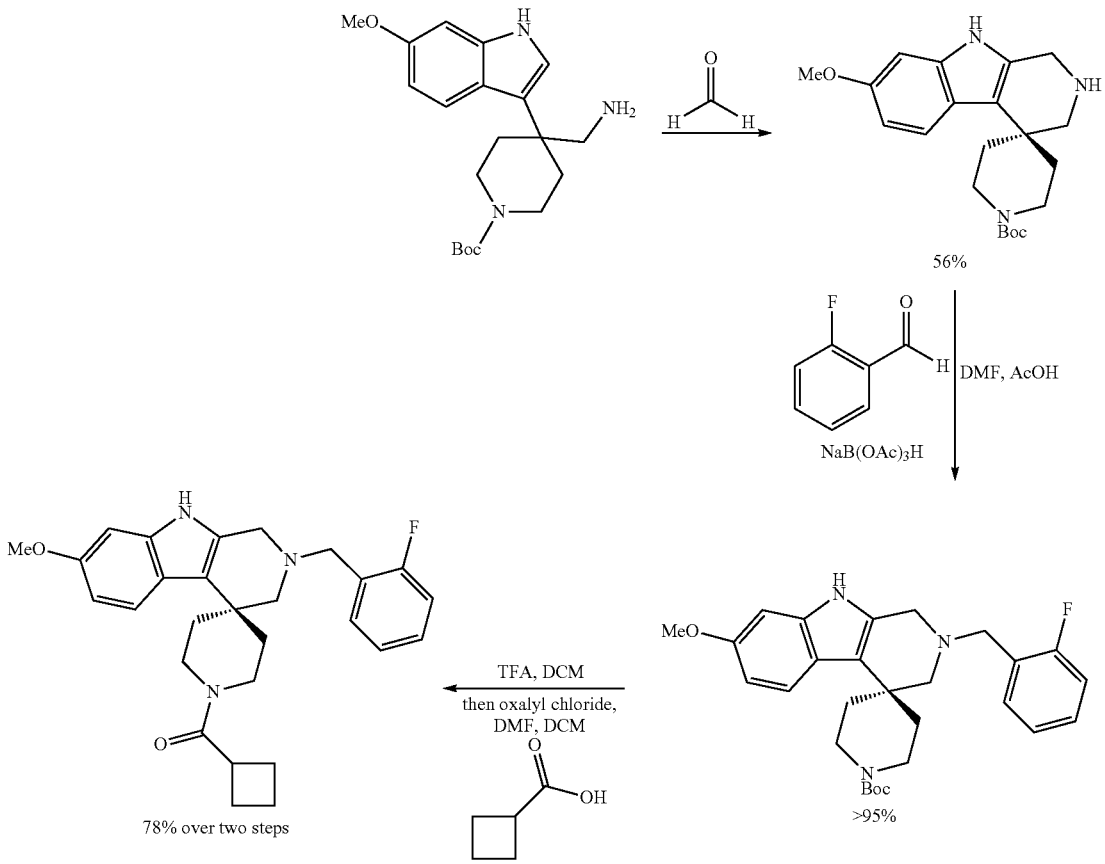

tert-butyl 7'-methoxy-1',2',3',9'-tetrahydrospiro[piperidine-4,4'-pyrido[3,4-b]indole]-1-carboxylate

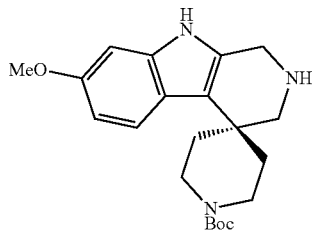

To a solution of tert-butyl 4-(aminomethyl)-4-(6-methoxy-1H-indol-3-yl)piperidine-1-carboxylate (60 mg, 0.167 mmol) in MeOH (0.1 M) was added benzoic acid (5 mg, 0.042 mmol) and 37% formaldehyde in H$_2$O (16.2 µL, 0.217 mmol). After 3 hours, the solvent was removed in vacuo and crude material purified by flash column chromatography eluting in MeOH/DCM (35 mg, 56%).

tert-butyl 2'-(2-fluorobenzyl)-7'-methoxy-1',2',3',9'-tetrahydrospiro[piperidine-4,4'-pyrido[3,4-b]indole]-1-carboxylate

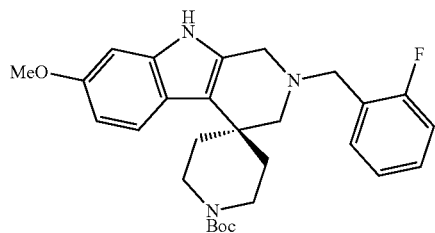

To a solution of tert-butyl 7'-methoxy-1',2',3',9'-tetrahydrospiro[piperidine-4,4'-pyrido[3,4-b]indole]-1-carboxylate (35 mg, 0.094 mmol) in 49:1 DMF/AcOH (0.025 M) was added 2-fluorobenzaldehyde (50 µL, 0.471 mmol), sodium triacetoxyborohydride (100 mg, 0.471 mmol), and 15 mg sodium sulfate. The reaction was stirred for 2 hours at ambient temperature, after which point the mixture was diluted with H$_2$O and extracted 3× with EtOAc. The organic layer was dried (Na$_2$SO$_4$), filtered and concentrated. The crude material was purified by flash column chromatography eluting with EtOAc/Hexanes to give the desired compound (25 mg, 44%).

cyclobutyl(2'-(2-fluorobenzyl)-7'-methoxy-1',2',3',9'-tetrahydrospiro[piperidine-4,4'-pyrido[3,4-b]indol]-1-yl)methanone

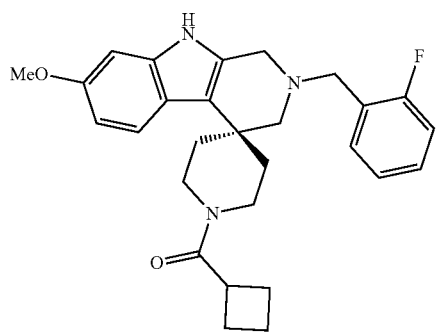

To a solution of tert-butyl 2'-(2-fluorobenzyl)-7'-methoxy-1',2',3',9'-tetrahydrospiro[piperidine-4,4'-pyrido[3,4-b]indole]-1-carboxylate 13 mg, 0.027 mmol) in DCM (0.05 M) was added trifluoroacetic acid (18 µL, 0.235 mmol). After 3 hours, the solvent was removed in vacuo to afford a crude residue. The crude residue was then dissolved in DCM (0.05 M) and Et$_3$N (19 µL, 0.136 mmol).

In a separate vial was added oxalyl chloride (2.9 µL, 0.032 mmol), DCM (0.05 M), and one drop of DMF. After 15 min, this solution was transferred via syringe to the crude mixture as described above and stirred at ambient temperature, after which point the combined mixture was quenched with saturated NH$_4$Cl and extracted 4× with DCM. The organic layer was dried (Na$_2$SO$_4$), filtered and concentrated. The crude material was purified by flash column chromatography eluting with MeOH/DCM to give the desired compound (9.7 mg, 78% over two steps).

Example 2 t(X;18) Translocation Results in Expression of the SS18-SSX1 Fusion

Synovial sarcoma is hallmarked by a specific chromosomal translocation, t(X;18)(p11.2;q11.2), found in more than 90% of all patients. This recurrent aberration leads to the fusion of two proteins, SS18 (SYT) and SSX (SSX1, SSX2, or SSX4), generating an oncogene that is necessary for synovial sarcoma initiation and propagation. The SS18-SSX fusion protein was found to be a stable member of the SWI/SNF (BAF) complex, leading to dramatic changes in BAF complex composition, including the ejection and degradation of BAF47 (SNF5), a core subunit, from the complex. This invention is based on the alteration of SS18-SSX or an SS18-SSX containing complex, as measured by the stabilization of BAF47 in SS cells. It was identified using an assay described in U.S. Patent Publication No. 20140288162, where BAF47 was fused to the Luciferase reporter protein in order to monitor BAF47 levels.

The effects of SS18-SSXI on BAF are illustrated in FIG. 1, which provides a schematic illustration of the role of BAF and the SS18-SSX fusion protein in synovial sarcoma (SSt (X;18) translocation results in expression of the SS18-SSX fusion protein. The SS18-SSX fusion protein integrates into the BAF complex. Wild-type SS18 and BAF47 are displaced from the BAF complex, and BAF47 is subsequently degraded. The BAF complex localizes over the Sox2 locus, and H3K27me3 marks are removed. Sox2 mRNA expression is induced to promote synovial sarcoma proliferation.

BAF47 protein levels correlate with SS18-SSX expression (FIG. 2). The assay used involves transducing a reporter fusion DNA construct comprising BAF47 and luciferase into synovial sarcoma cell lines, such as but not limited to Aska and Yamato. The bar graphs illustrates relative luciferase units for transduced cell lines.

This approach involves the use of a high-throughput, gain-of-function screening method to detect molecules with the ability to favor the assembly of the normal BAF complex. Incorporation of the SS18-SSX fusion protein leads to eviction of BAF47 and its subsequent destabilization and proteasome-mediated degradation. Hence, an agent that would favor assembly of normal BAF complexes would lead to increased levels of the BAF47 protein by virtue of its ability to assembly into complexes and its subsequent stabilization (as demonstrated with shRNA-mediated knock down of the SS18-SSX fusion or by overexpression of full length wild-type SS18 (SS18FL). Therefore, small molecules that lead to the re-assembly of BAF47 into complexes are expected to result in an increase in luciferase signal.

Figure 3:
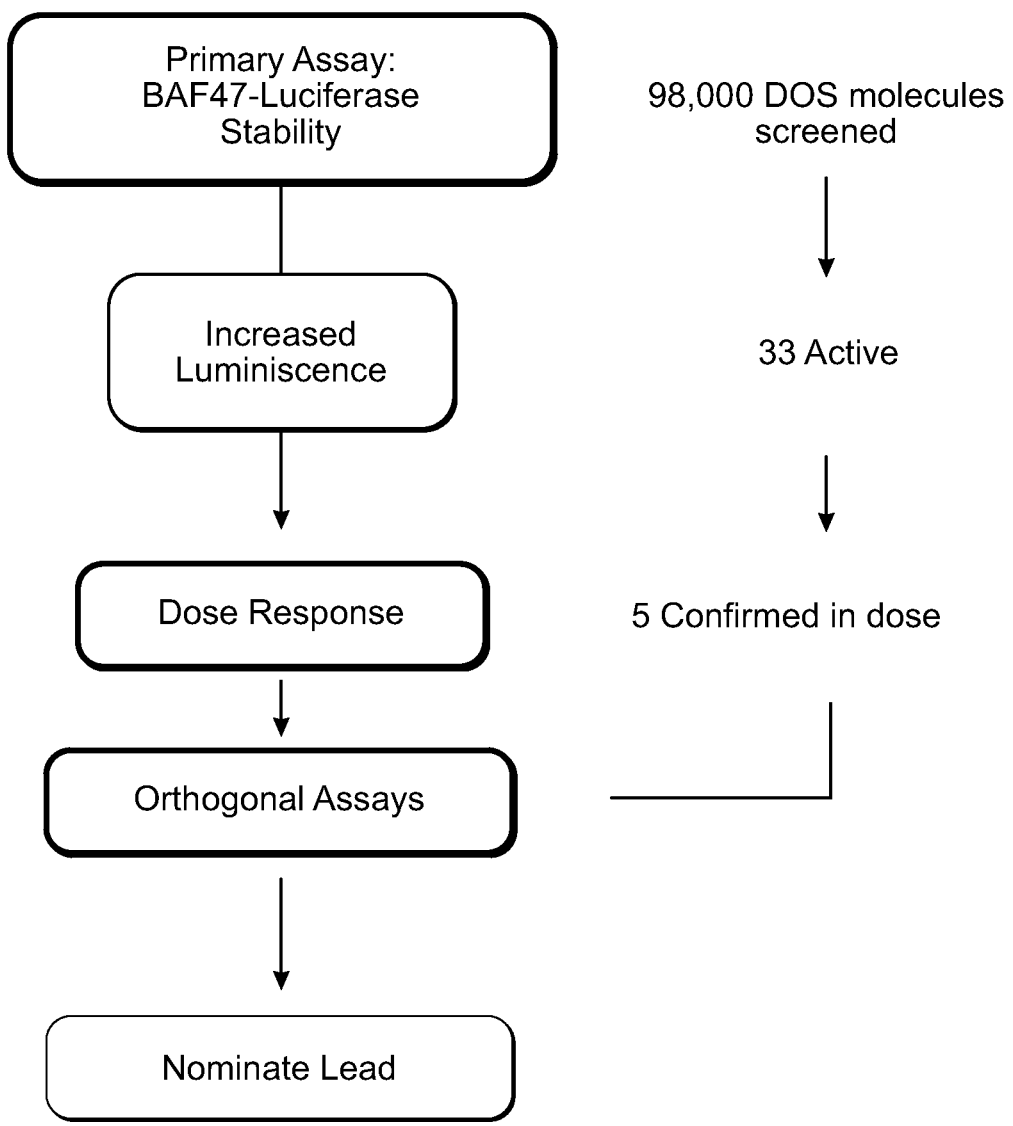
FIG. 3 comprises a fluxogram illustrating the identification of BAF47 stabilizers in Aska cells. The schematic describes the steps that were taken to identify lead compounds.

FIG. 3 illustrates the approach used to identify BAF47 stabilizers. 98,000 DOS molecules were screened. 33 compounds that increased luminescence were identified. Five of these compounds showed a dose response when retested at the 48 hr and 72 hour time points.

Figure 4:
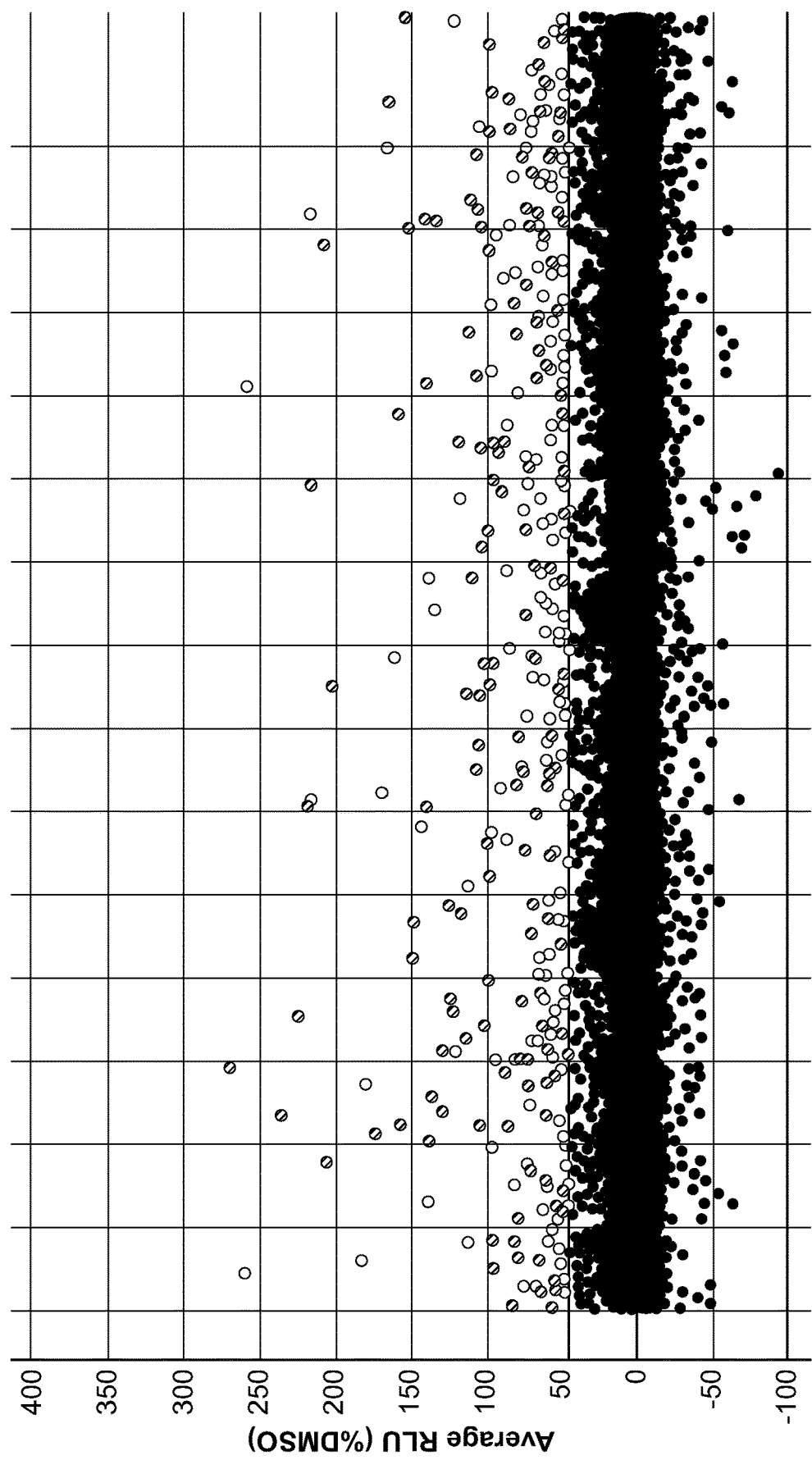
FIG. 4 comprises a graph illustrating the results from the high-throughput screening of potential BAF47 stabilizers. Compounds in dark gray are active compounds that scored as positive hits in the primary HTS screen, compounds in light gray were scored as positive but only in singlicate (not replicate), and compounds below the solid line were scored as inactive/negative. Solid line indicates >145% activity relative to the DMSO control.

The results of the high-throughput screening of potential BAF47 stabilizers is shown in FIG. 4. 33 compounds with activity were identified (activity>3.5×Standard deviation of DMSO).

Exemplary dose response curves for Compound 5 and Compound 6 are provided at FIGS. 5A and 5B.

Figure 6:
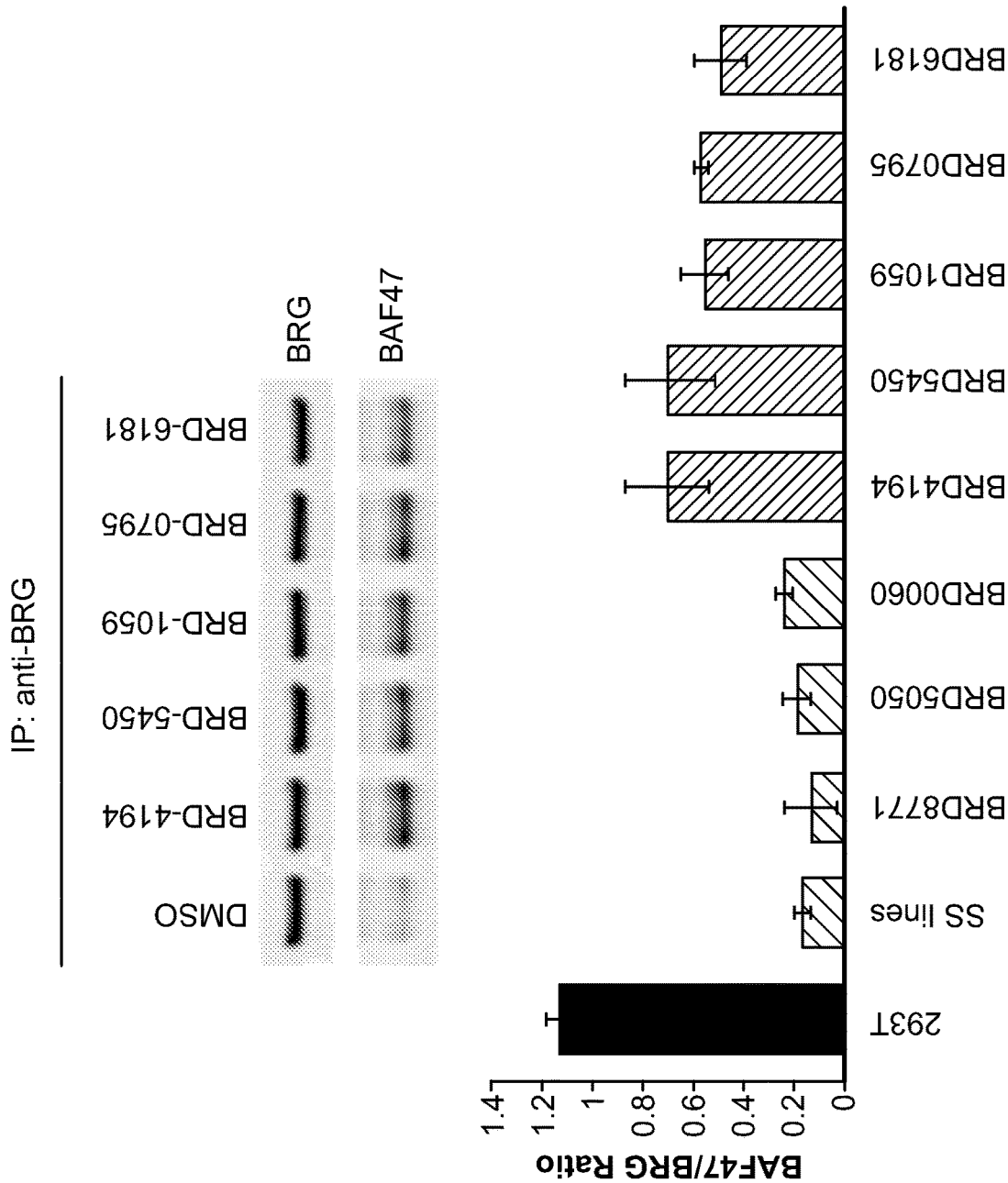
FIG. 6 comprises a set of images and bar graph illustrating the finding that compounds of the invention stabilize BAF47 within the BAF complex, as demonstrated using immunoprecipitation (IP) of BAF complexes and western blotting with anti-BAF47 antibodies. Briefly, naïve, unmodified Aska SS cells were treated for 48 hours at 16 µM concentration of all 5 positive hit compounds (as well as negative compounds for controls). The western blot reflects IPs of BAF complexes highlighting increased incorporation/stability of BAF47 relative to DMSO control. The bar graph highlights levels of BAF47 (measured via western blot quantitative densitometry) over n=3 experiments for each compound, including testing against three other negative compounds.
Figure 7:
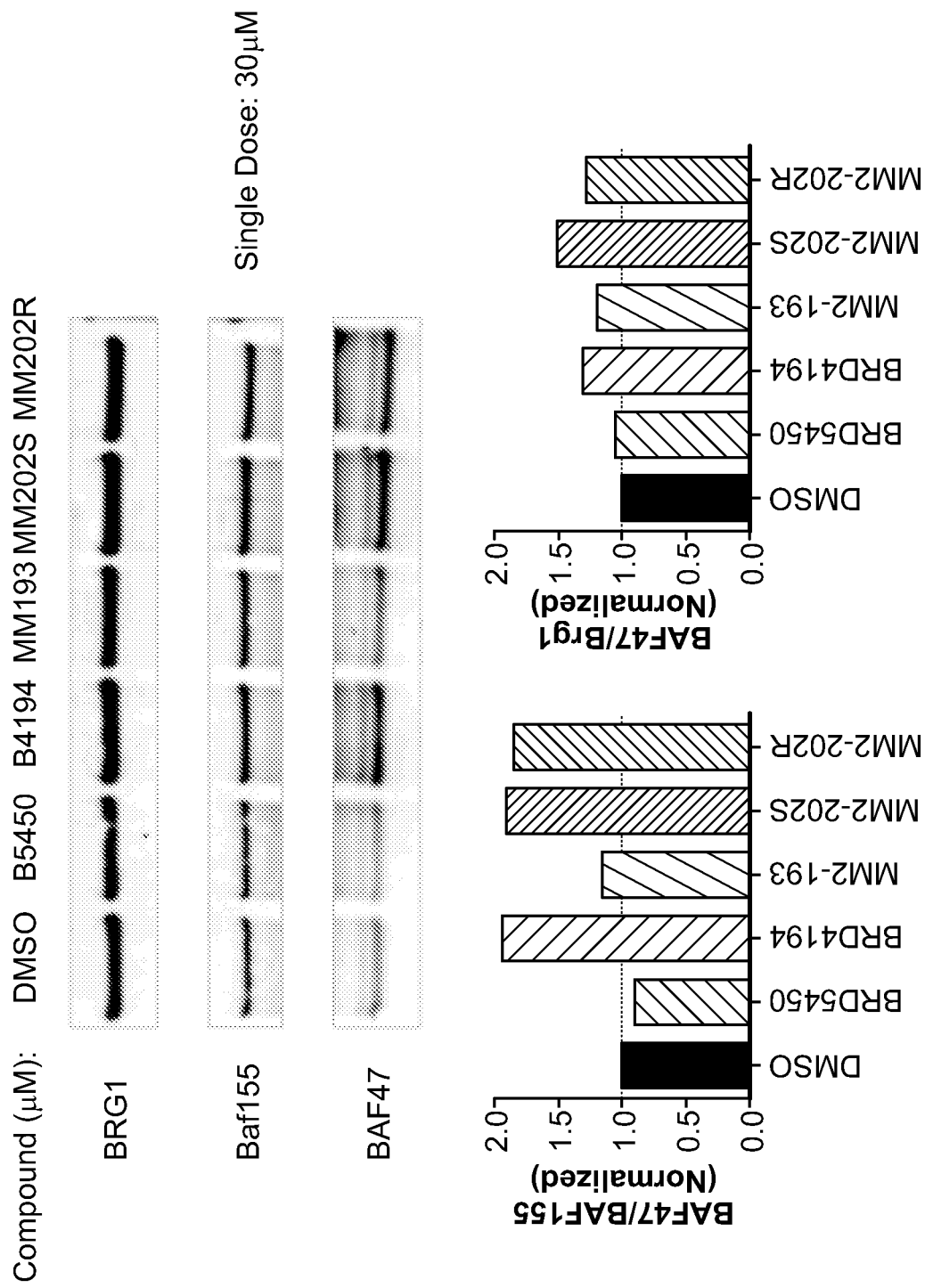
FIG. 7 comprises a set of images and bar graphs illustrating the finding that compounds of the invention stabilize BAF47 within the BAF complex, as demonstrated using immunoprecipitation of BAF complexes and western blotting for BAF complex components such as BAF47. These include resynthesized positive hits for Compounds 5-6.

Compounds of the invention (e.g., Compound 5, Compound 6, Compound 3, Compound 1, and Compound 8) stabilized BAF47 as demonstrated using anti-Brg immunoprecipitation (IP) followed by anti-BAF47 western blot analysis in synovial sarcoma cell line (Aska cells) (FIG. 6).

Compounds of the invention stabilized BAF47 within the BAF complex, as demonstrated using BAF155 immunoprecipitation after Aska cells were treated for twenty-four hours with a single 30 micromolar dose of the following compounds: Compound 6, Compound 5, Compound 11, and resynthesized Compounds 5-6.

Compound 5 activity in Yamato cells is shown in FIG. 8. Yamato cells were treated with a single dose thirty micromolar dose of Compound 5. Baf155 immunoprecipitation was carried out twenty-four hours after treatment and western blotting was performed for BAF47 protein levels on BAF complexes.

Figure 9:
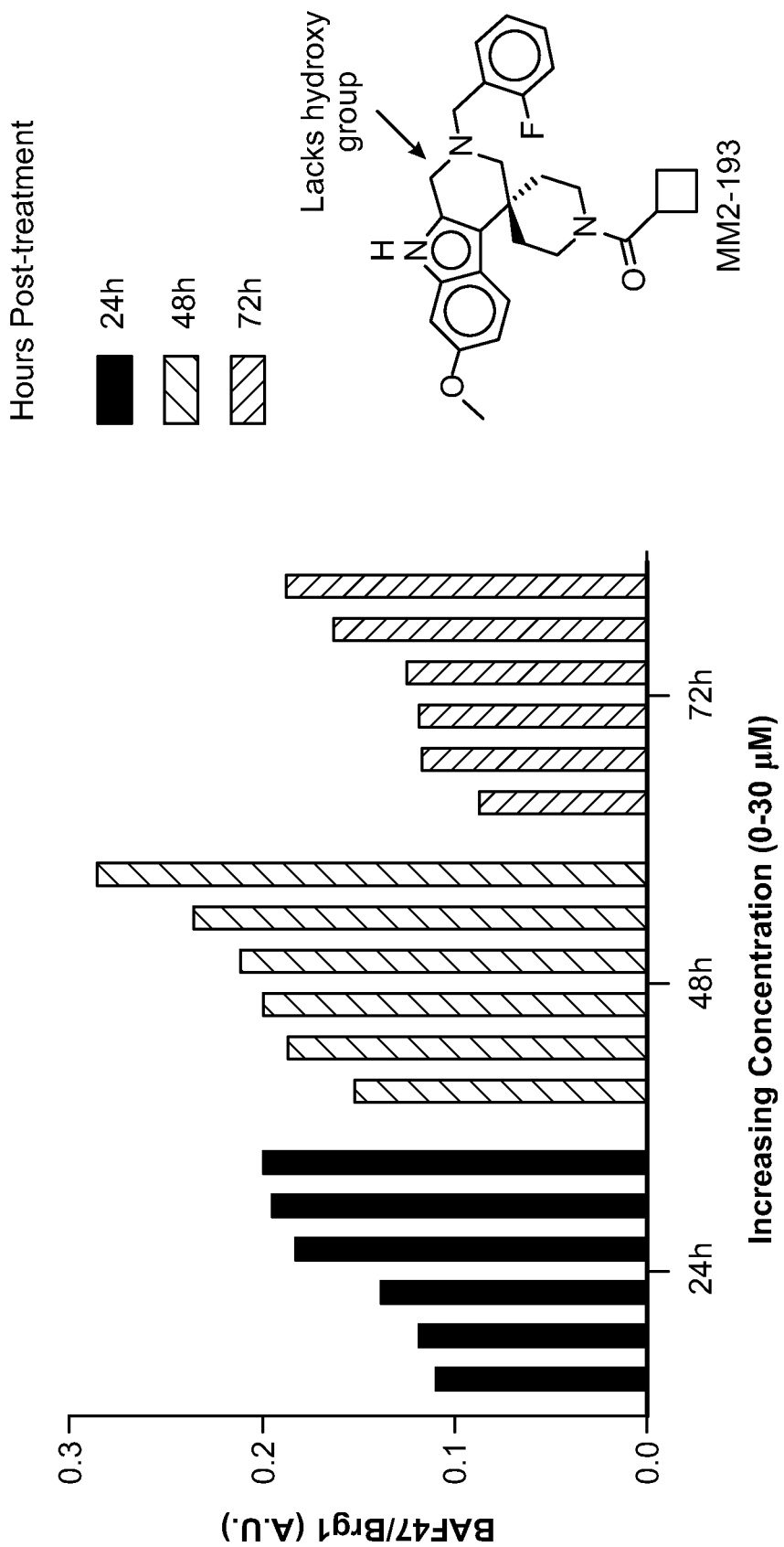
FIG. 9 comprises a set of bar graphs illustrating the effects of Compound 11 (illustrated), the lead compound lacking the hydroxyl group, as a function of time and dose in Aska cells. Compound 11 increases BAF47 stability in dose-dependent manner.

The effects of Compound 11 as a function of time and dose in Aska cells is shown in FIG. 9. Compound 11 was added at doses from 0-30 micromolar, and the results monitored at 24, 48, and 72 hours after treatment.

Figure 11:
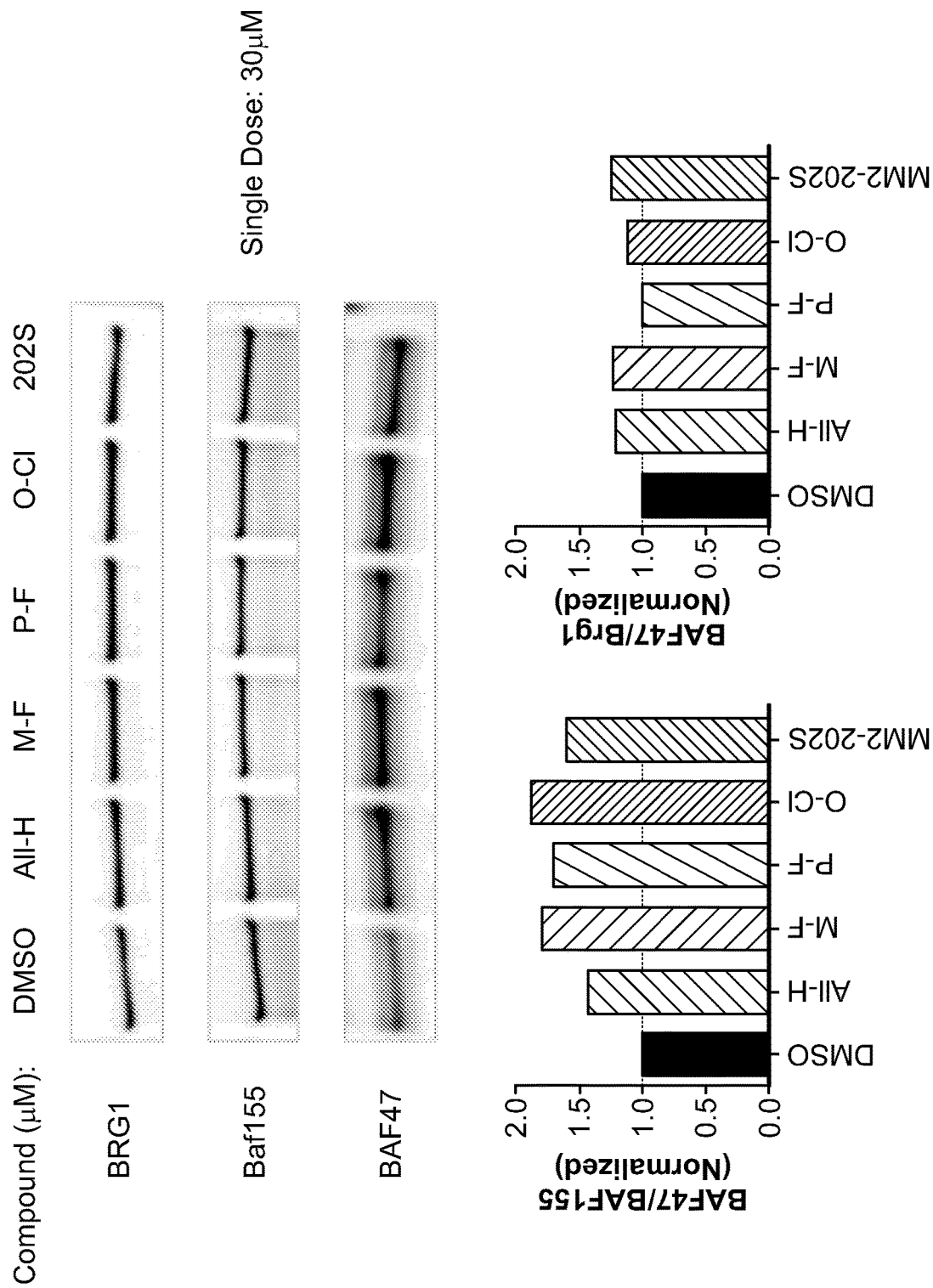
FIG. 11 comprises a set of bar graphs and images illustrating the effects of certain compounds of the invention (as illustrated in FIG. 10) in BAF immunoprecipitation after 24 h treatment in Aska cells. Briefly, additional analogs of lead compounds were synthesized: Compound 12 (hydrogen), Compound 13 (meta-fluorine), Compound 14 (para-fluorine), and Compound 15 (ortho-chlorine). Synovial sarcoma cells were treated with compounds and anti-BAF IPs were performed to reveal changes to complex composition. BAF47 levels are affected as indicated in the figure.

Synthesized analogs of Compound 5 are shown at FIG. 10. The effect of compounds Compounds 12-15 on Aska cells is shown at FIG. 11. Aska cells were treated with a single thirty micromolar dose of each compound, and the effects were assessed twenty-four hours after treatment using BAF immunoprecipitation.

Figure 12:
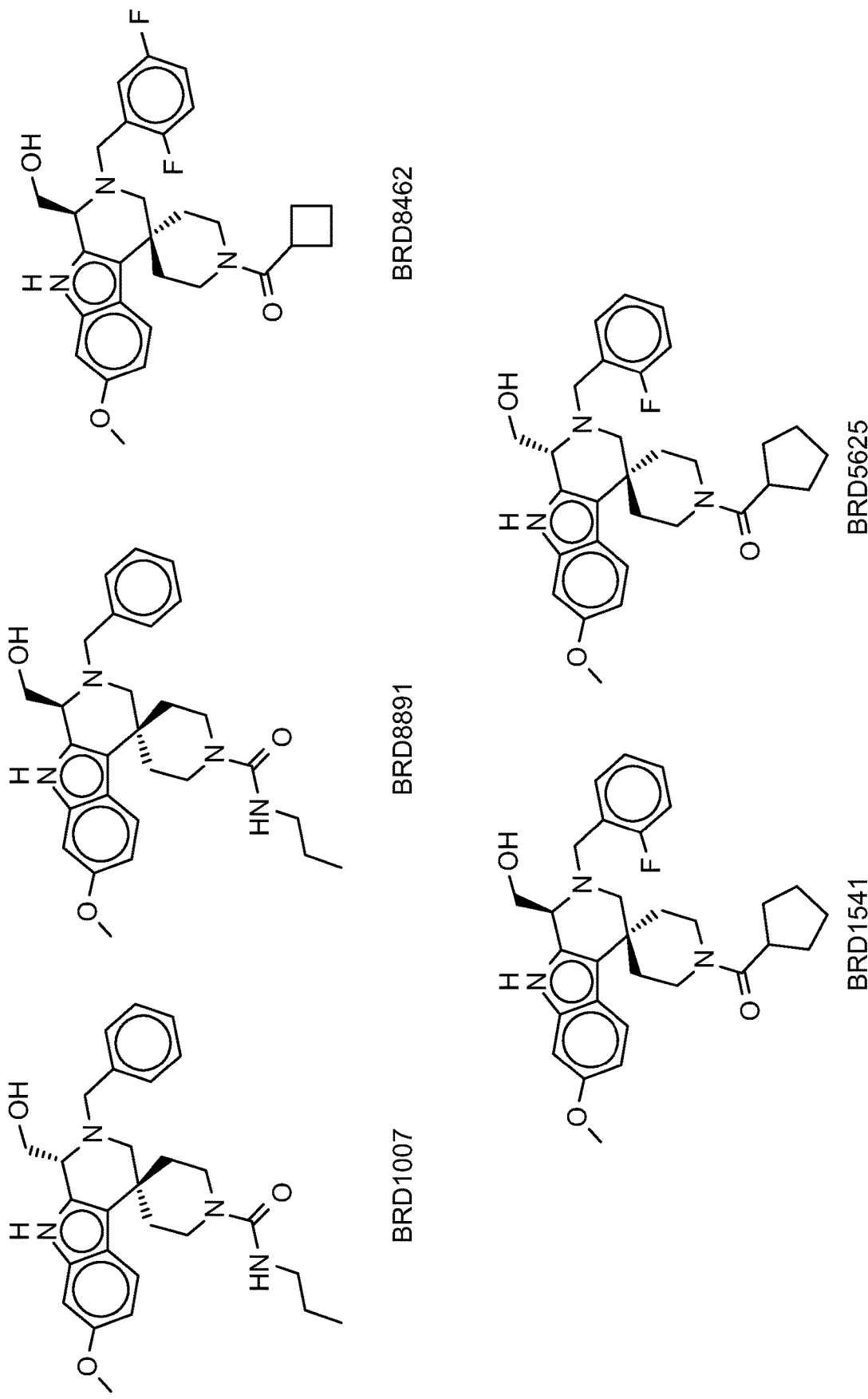
FIG. 12 illustrates certain compounds of the invention.
Figure 13:
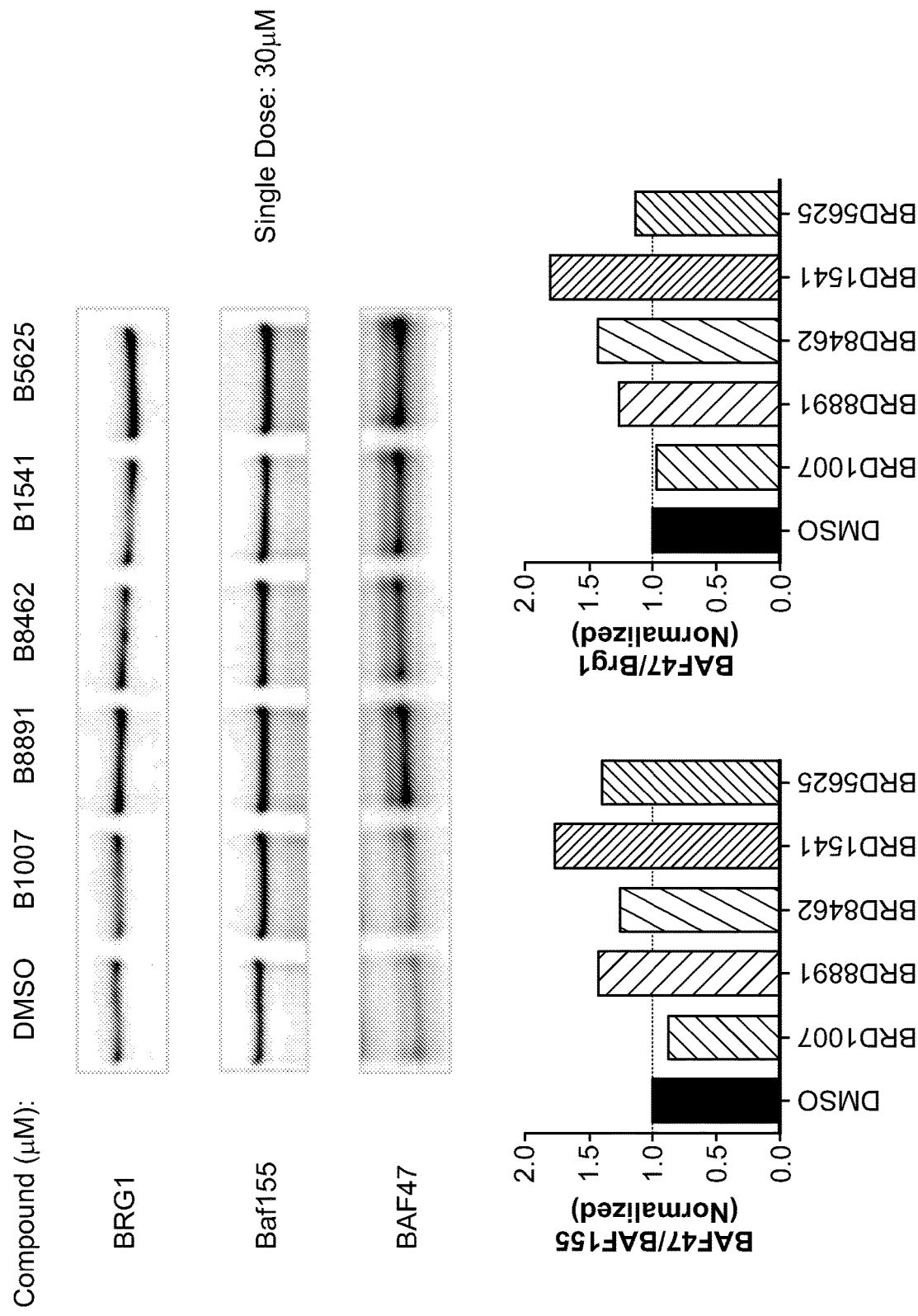
FIG. 13 comprises a set of bar graphs and images illustrating the effects of certain compounds of the invention (as illustrated in FIG. 12) in BAF155 immunoprecipitation after 24 h treatment in Aska cells. Briefly, additional analogs of lead compounds were synthesized, as shown. Synovial sarcoma cells were treated with compounds and anti-BAF IPs were performed to reveal changes to complex composition. BAF47 levels are affected as indicated in the figure.
Figure 14:
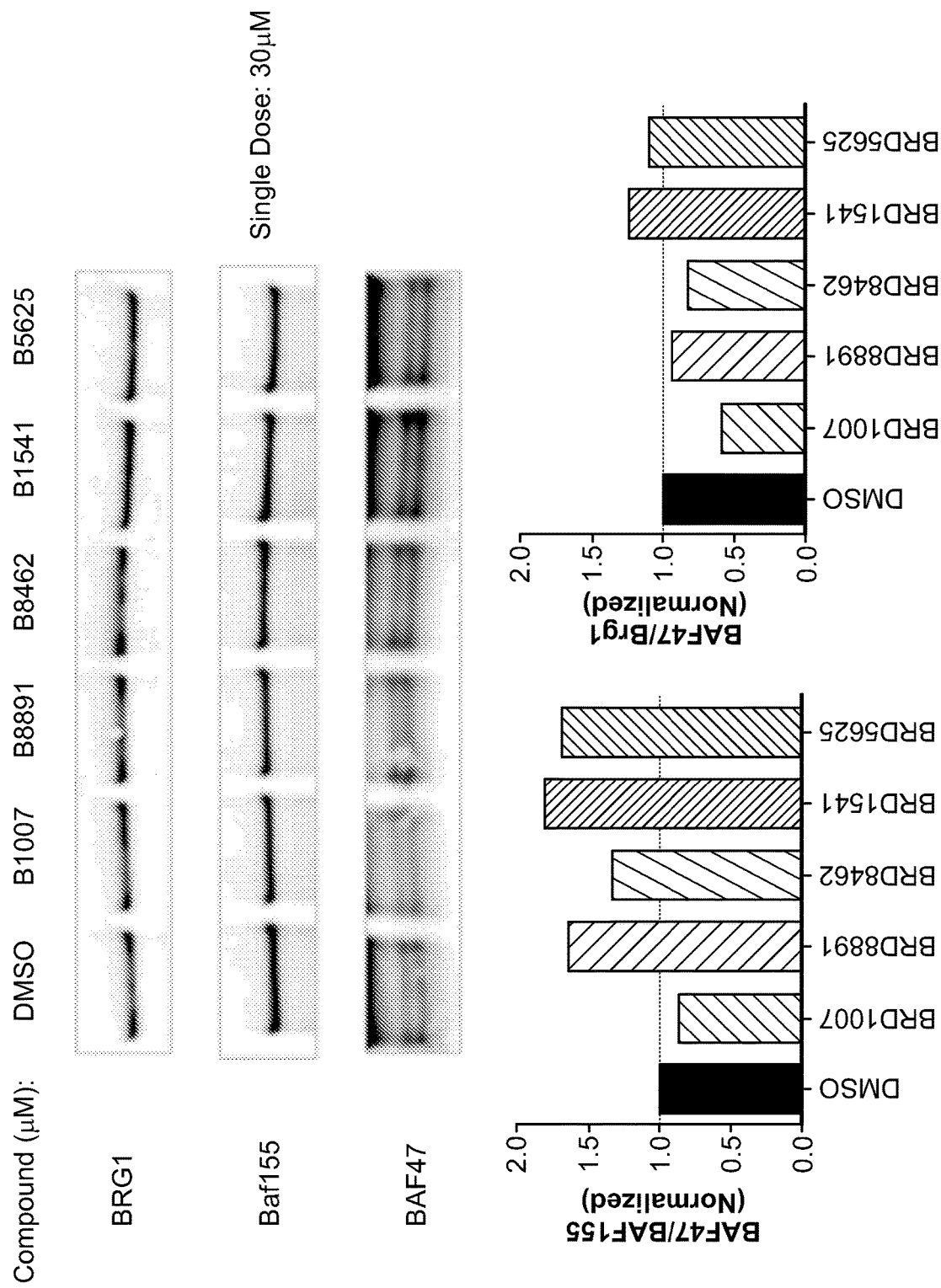
FIG. 14 comprises a set of bar graphs and images illustrating the effects of certain compounds of the invention (as illustrated in FIG. 12) in BAF155 immunoprecipitation after 24 h treatment in Yamato cells. Briefly, additional analogs of lead compounds were synthesized, as shown in FIG. 12. Synovial sarcoma cells were treated with compounds and anti-BAF IPs were performed to reveal changes to complex composition. BAF47 levels are affected as indicated in the figure.

Synthesized analogs of Compound 5 are shown at FIG. 12. The effect of compounds Compound 2, Compound 10, Compound 9, Compound 4, and Compound 7 on Aska cells is shown at FIG. 13 and on Yamato cells is shown at FIG. 14. Aska and Yamato cells were treated with a single thirty micromolar dose of each compound, and the effects were assessed twenty-four hours after treatment using BAF immunoprecipitation.

Figure 15C:
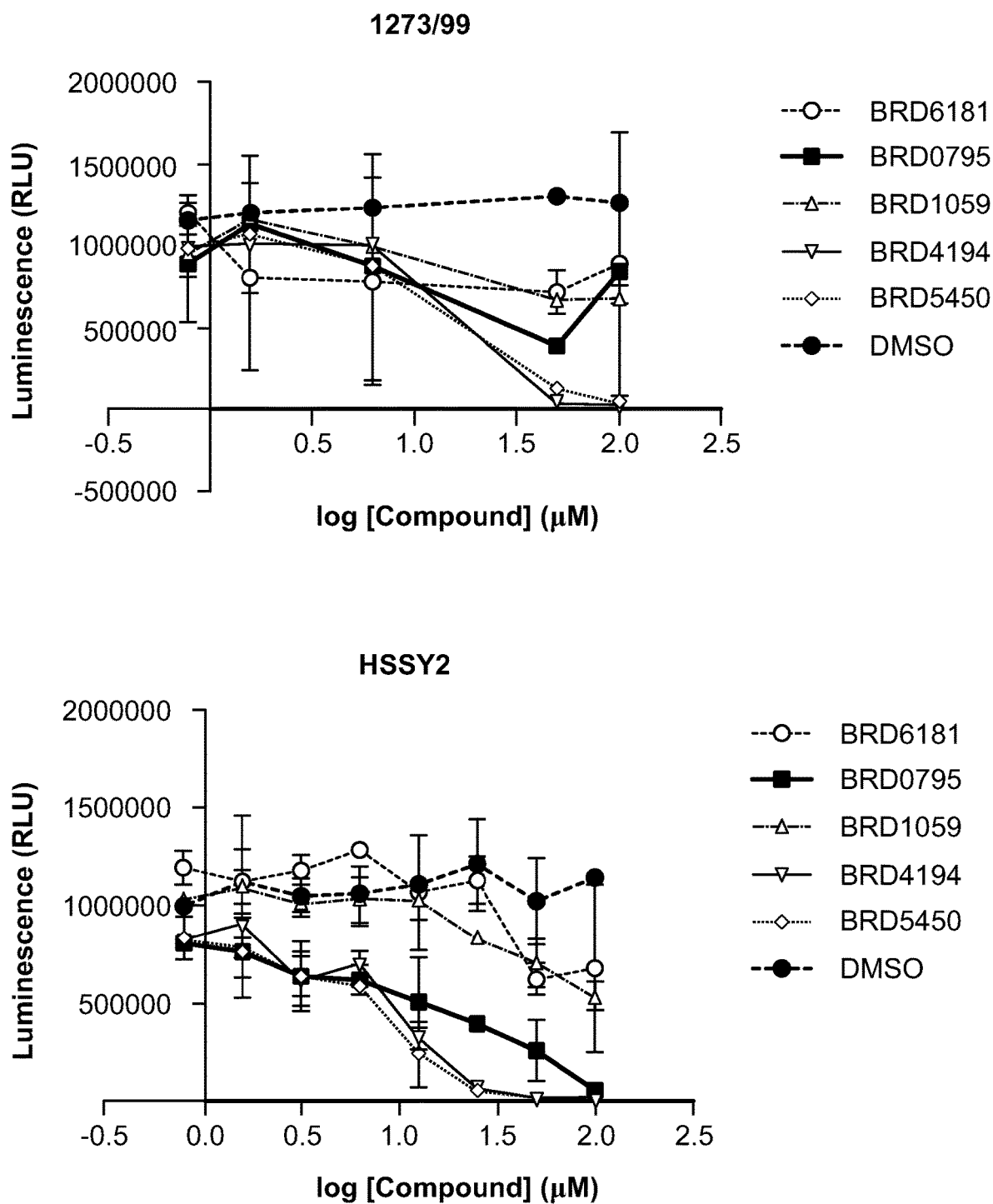

The effect of compounds of the invention on synovial sarcoma cell viability was assessed as measured by CellTiter Glo® luminescence (FIGS. 15A-15B). Briefly, cells were plated under standard conditions and allowed to grow to 75% confluence prior to treatment with compounds. Cell-TiterGlo reagent was used to measure cell viability.

The disclosures of each and every patent, patent application, and publication cited herein are hereby incorporated herein by reference in their entirety. Also incorporated by reference is the disclosure of U.S. Pat. No. 9,428,507. In particular embodiments, a compound of the invention is not a compound described in Table 1 of U.S. Pat. No. 9,428,507.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A compound having the structure of formula I:

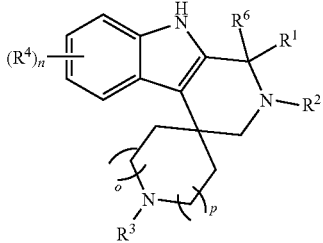

Formula I wherein n is 1, 2, 3, or 4;

o and p are independently 0, 1, or 2;

$R^1$ and $R^6$ are, independently, selected from the group consisting of H and $C_1$-$C_6$ alkyl, wherein the alkyl group is optionally substituted with at least one independently selected from the group consisting of $C_1$-$C_6$ alkyl, $C_3$-$C_8$ cycloalkyl, halo, —OH, $C_1$-$C_6$ alkoxy, $C_1$-$C_6$ haloalkoxy, —$NH_2$, —NHC(=O)($C_1$-$C_6$ alkyl), —NH($C_1$-$C_6$ alkyl) and —N($C_1$-$C_6$ alkyl)($C_1$-$C_6$ alkyl);

$R^2$ is hydrogen, $C_1$-$C_6$ alkyl, $C_1$-$C_6$ perfluoroalkyl, $C_6$-$C_{10}$ aryl $C_1$-$C_6$ alkyl, $C_1$-$C_6$ heteroaryl $C_1$-$C_6$ alkyl, $C_2$-$C_9$ heterocyclyl $C_1$-$C_6$ alkyl, or $C_3$-$C_{10}$ carbocyclyl $C_1$-$C_6$ alkyl, wherein the alkyl group is optionally substituted with at least one independently selected from the group consisting of $C_1$-$C_6$ alkyl, $C_3$-$C_8$ cycloalkyl, halo, —OH, $C_1$-$C_6$ alkoxy, $C_1$-$C_6$ haloalkoxy, —$NH_2$, —NHC(=O)($C_1$-$C_6$ alkyl), —NH($C_1$-$C_6$ alkyl) and —N($C_1$-$C_6$ alkyl)($C_1$-$C_6$ alkyl) and the aryl, heteroaryl, heterocyclyl, or carbocyclyl group is optionally substituted with at least one independently selected from the group consisting of $C_1$-$C_6$ alkyl, $C_1$-$C_6$ haloalkyl, $C_3$-$C_8$ cycloalkyl, halo, —OH, $C_1$-$C_6$ alkoxy, $C_1$-$C_6$ haloalkoxy, —$NH_2$, —NH($C_1$-$C_6$ alkyl), —N($C_1$-$C_6$ alkyl)($C_1$-$C_6$ alkyl), —$NO_2$, —C(=O)OH, —C(=O)OR, and —NHC(=O)($C_1$-$C_6$ alkyl);

$R^3$ is selected from the group consisting of —C(=O)$R^C$, and —C(=O)N($R^A$)$_2$; and each occurrence of $R^4$ is independently selected from the group consisting of $C_1$-$C_6$ alkyl, $C_1$-$C_6$ haloalkyl, $C_3$-$C_8$ cycloalkyl, halo, —OH, $C_1$-$C_6$ alkoxy, $C_1$-$C_6$ haloalkoxy, —NH$_2$, —NH(C$_1$-C$_6$ alkyl), —N(C$_1$-C$_6$ alkyl)(C$_1$-C$_6$ alkyl), —NO$_2$, —C(=O)OH, —C(=O)OR, and —NHC(=O)(C$_1$-C$_6$ alkyl); where R$^A$ is independently selected at each occurrence from hydrogen or a C$_1$-C$_6$ linear or branched alkyl;

R$^C$ is a saturated C$_3$-C$_8$ cycloalkyl; and each R is, independently, selected from the group consisting of hydrogen, C$_1$-C$_6$ alkyl, C$_1$-C$_6$ heteroaryl, C$_6$-C$_{10}$ aryl, C$_3$-C$_8$ cycloalkyl, C$_2$-C$_9$ heterocyclyl, C$_6$-C$_{10}$ aryl C$_1$-C$_6$ alkyl, C$_1$-C$_6$ heteroaryl C$_1$-C$_6$ alkyl, wherein the alkyl, cycloalkyl, aryl, heteroaryl, or heterocyclyl group is optionally substituted with at least one independently selected from the group consisting of C$_1$-C$_6$ alkyl, —OH, —(C$_1$-C$_6$ alkoxy), halo, —NH$_2$, —NHC(=O)(C$_1$-C$_6$ alkyl), —NH(C$_1$-C$_6$ alkyl) and —N(C$_1$-C$_6$ alkyl)(C$_1$-C$_6$ alkyl);

with the proviso that said compound is not:

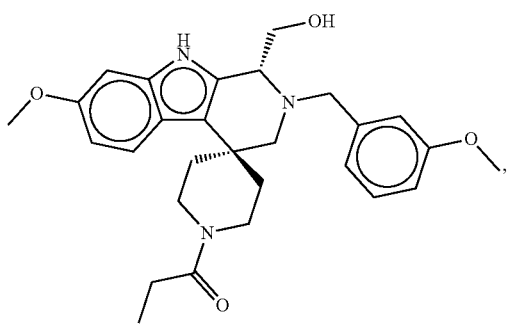

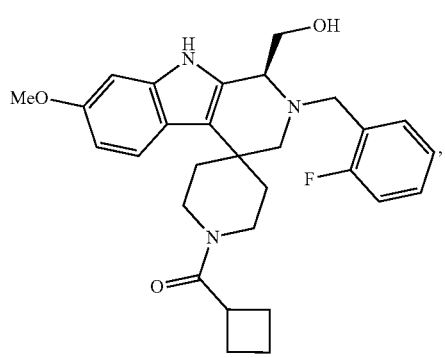

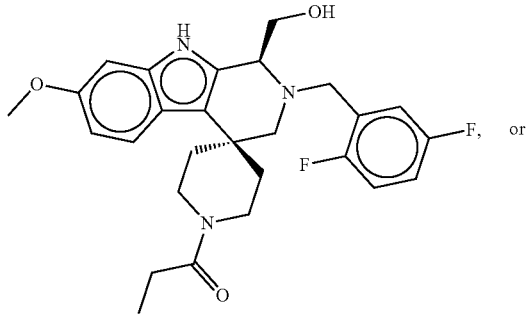

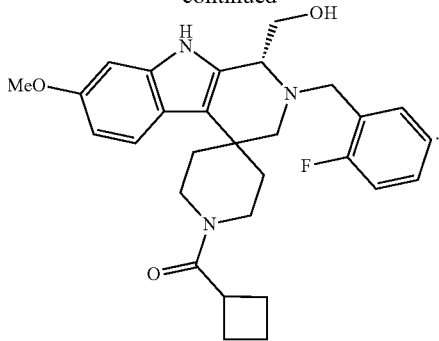

2. The compound according to claim 1, wherein

R$^1$ and R$^6$ are independently selected from hydrogen, hydroxymethyl, hydroxyethyl, or hydroxypropyl;

R$^2$ is optionally substituted benzyl;

R$^3$ is —C(=O)R$^C$ and R$^C$ is a C$_4$-C$_5$ cycloalkyl or wherein R$^3$ is —C(=O)NHR$^A$;

each occurrence of R$^4$ is independently selected from the group consisting of C$_1$-C$_6$ alkyl, C$_1$-C$_6$ haloalkyl, C$_3$-C$_8$ cycloalkyl, halo, —OH, C$_1$-C$_6$ alkoxy, C$_1$-C$_6$ haloalkoxy, —NH$_2$, —NH(C$_1$-C$_6$ alkyl), —N(C$_1$-C$_6$ alkyl)(C$_1$-C$_6$ alkyl), —NO$_2$, —C(=O)OH, —C(=O)OR, and —NHC(=O)(C$_1$-C$_6$ alkyl).

3. The compound according to claim 2, wherein R$^2$ is fluorobenzyl.

4. The compound according to claim 2, wherein R$^1$ and R$^6$ are independently selected from hydrogen or hydroxymethyl.

5. The compound according to claim 1, wherein R$^1$ is —(CH$_2$)$_q$XR$^7$, wherein q is 1, 2, 3, 4, 5, or 6, X is absent, O, or NR$^8$, R$^7$ is hydrogen or C$_1$-C$_6$ alkyl, and R$^8$ is hydrogen or C$_1$-C$_6$ alkyl.

6. The compound according to claim 1, wherein R$^1$ is selected from the group consisting of H and C$_1$-C$_6$ alkyl, wherein the alkyl group is optionally substituted with at least one independently selected from the group consisting of C$_1$-C$_6$ alkyl, C$_3$-C$_8$ cycloalkyl, halo, —OH, C$_1$-C$_6$ alkoxy, C$_1$-C$_6$ haloalkoxy, —NH$_2$, —NHC(=O)(C$_1$-C$_6$ alkyl), —NH(C$_1$-C$_6$ alkyl) and —N(C$_1$-C$_6$ alkyl)(C$_1$-C$_6$ alkyl) and R$^6$ is hydrogen.

7. The compound according to claim 1, wherein R$^2$ is (CH$_2$)$_m$R$^5$, wherein m is 1, 2 or 3, and wherein R$^5$ is selected from the group consisting of aryl and heteroaryl, wherein the aryl or heteroaryl group is optionally substituted with at least one independently selected from the group consisting of C$_1$-C$_6$ alkyl, C$_1$-C$_6$ haloalkyl, C$_3$-C$_8$ cycloalkyl, halo, —OH, C$_1$-C$_6$ alkoxy, C$_1$-C$_6$ haloalkoxy, —NH$_2$, —NH(C$_1$-C$_6$ alkyl), —N(C$_1$-C$_6$ alkyl)(C$_1$-C$_6$ alkyl), —NO$_2$, —C(=O)OH, —C(=O)OR, and —NHC(=O)(C$_1$-C$_6$ alkyl).

8. The compound according to claim 1, wherein o and p are 1.

9. The compound according to claim 1, wherein the compound has the structure of Formula IA and/or Formula IB:

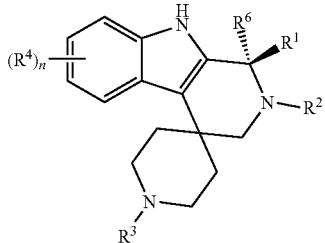

Formula IA

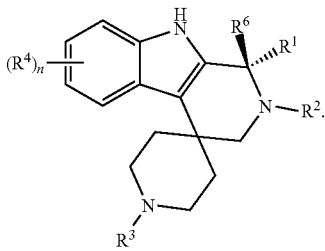

Formula IB

10. A compound of formula (II), or a salt, solvate or stereoisomer thereof:

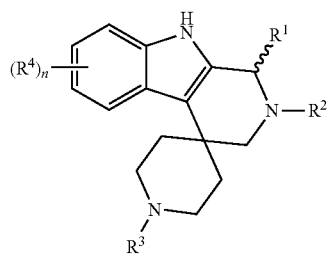

Formula II wherein $R^1$ is selected from the group consisting of H and $C_1$-$C_6$ alkyl, wherein the alkyl group is optionally substituted with at least one independently selected from the group consisting of $C_1$-$C_6$ alkyl, $C_3$-$C_8$ cycloalkyl, halo, —OH, $C_1$-$C_6$ alkoxy, $C_1$-$C_6$ haloalkoxy, —$NH_2$, —NHC(=O)($C_1$-$C_6$ alkyl), —NH($C_1$-$C_6$ alkyl) and —N($C_1$-$C_6$ alkyl)($C_1$-$C_6$ alkyl);

$R^2$ is $(CH_2)_m R^5$, wherein m is 1, 2 or 3, and wherein $R^5$ is selected from the group consisting of aryl and heteroaryl, wherein the aryl or heteroaryl group is optionally substituted with at least one independently selected from the group consisting of $C_1$-$C_6$ alkyl, $C_1$-$C_6$ haloalkyl, $C_3$-$C_8$ cycloalkyl, halo, —OH, $C_1$-$C_6$ alkoxy, $C_1$-$C_6$ haloalkoxy, —$NH_2$, —NH($C_1$-$C_6$ alkyl), —N($C_1$-$C_6$ alkyl)($C_1$-$C_6$ alkyl), —$NO_2$, —C(=O)OH, —C(=O)OR, and —NHC(=O)($C_1$-$C_6$ alkyl);

$R^3$ is selected from the group consisting of H, —S(=O)$_2$R, —C(=O)R, —S(=O)$_2$NHR and —C(=O)NHR, wherein R is selected from the group consisting of $C_1$-$C_6$ alkyl and saturated $C_3$-$C_8$ cycloalkyl, wherein the alkyl or cycloalkyl group is optionally substituted with at least one moiety independently selected from the group consisting of $C_1$-$C_6$ alkyl, —OH, —($C_1$-$C_6$ alkoxy), halo, —$NH_2$, —NHC(=O)($C_1$-$C_6$ alkyl), —NH($C_1$-$C_6$ alkyl) and —N($C_1$-$C_6$ alkyl)($C_1$-$C_6$ alkyl);

each occurrence of $R^4$ is independently selected from the group consisting of $C_1$-$C_6$ alkyl, $C_1$-$C_6$ haloalkyl, $C_3$-$C_8$ cycloalkyl, halo, —OH, $C_1$-$C_6$ alkoxy, $C_1$-$C_6$ haloalkoxy, —$NH_2$, —NH($C_1$-$C_6$ alkyl), —N($C_1$-$C_6$ alkyl)($C_1$-$C_6$ alkyl), —$NO_2$, —C(=O)OH, —C(=O)OR, and —NHC(=O)($C_1$-$C_6$ alkyl); and n is 0, 1, 2, 3 or 4;

with the proviso that said compound is not:

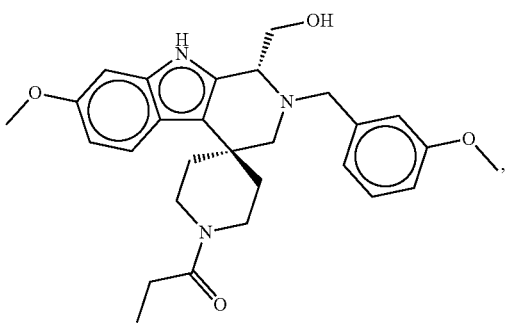

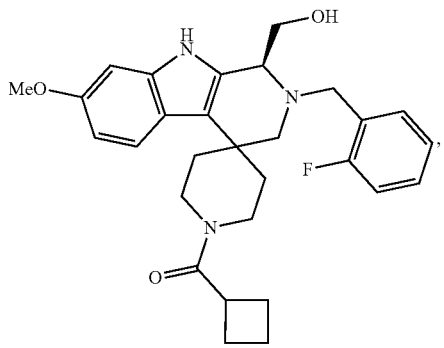

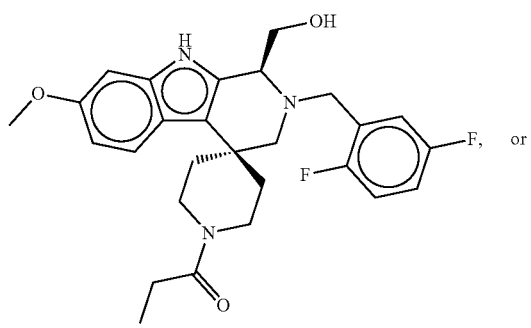, or

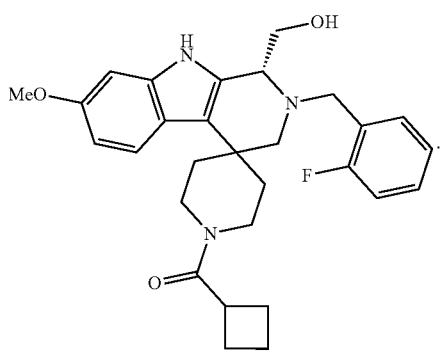

11. The compound of claim 10, which is a compound of formula (IIA), or a salt or solvate thereof:

Formula IIA

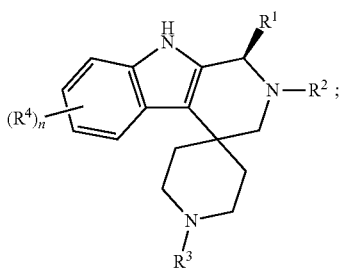

or a compound of formula (IIB), or a salt or solvate thereof:

Formula IIB

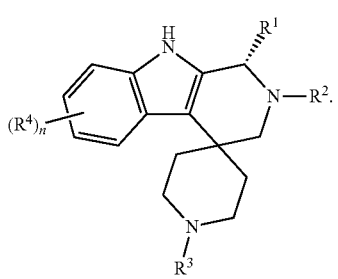

12. The compound of claim 10, wherein $R^1$ is selected from the group consisting of H and $C_1$-$C_6$ alkyl, wherein the alkyl group is optionally substituted with at least one independently selected from the group consisting of $C_1$-$C_6$ alkyl, halo, —OH, $C_1$-$C_6$ alkoxy, and $C_1$-$C_6$ haloalkoxy;

wherein $R^2$ is $CH_2R^5$;

$R^3$ is selected from the group consisting of H, —S(=O)$_2$R, —C(=O)R, —S(=O)$_2$NHR and —C(=O)NHR, wherein R is selected from linear or branched $C_1$-$C_6$ alkyl or $C_3$-$C_8$ alicyclic cycloalkyl;

$R^4$ is independently selected from the group consisting of $C_1$-$C_6$ alkyl, $C_1$-$C_6$ haloalkyl, $C_3$-$C_8$ cycloalkyl, halo, —OH, $C_1$-$C_6$ alkoxy and $C_1$-$C_6$ haloalkoxy wherein $R^5$ is aryl optionally substituted with at least one independently selected from the group consisting of $C_1$-$C_6$ alkyl, $C_1$-$C_6$ haloalkyl, $C_3$-$C_8$ cycloalkyl, halo, —OH, $C_1$-$C_6$ alkoxy, $C_1$-$C_6$ haloalkoxy, —NH$_2$, —NH($C_1$-$C_6$ alkyl), —N($C_1$-$C_6$ alkyl)($C_1$-$C_6$ alkyl), —NO$_2$, —C(=O)OH, —C(=O)OR, and —NHC(=O)($C_1$-$C_6$ alkyl).

13. The compound of claim 10, wherein n is 1, and $R^4$ is at the 7' position of (II).

14. The compound of claim 10, which is at least one selected from the group consisting of:

cyclobutyl(2'-(2-fluorobenzyl)-7'-methoxy-1',2',3',9'-tetrahydrospiro[piperidine-4,4'-pyrido[3,4-b]indol]-1-yl)methanone:

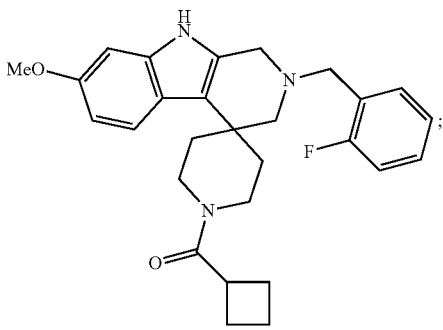 [SMILES: COc1ccc2c3c([nH]c2c1)CN(Cc1ccccc1F)CC31CCN(C(=O)C2CCC2)CC1]

(S)-(2'-benzyl-1'-(hydroxymethyl)-7'-methoxy-1',2',3',9'-tetrahydrospiro[piperidine-4,4'-pyrido[3,4-b]indol]-1-yl)(cyclobutyl):

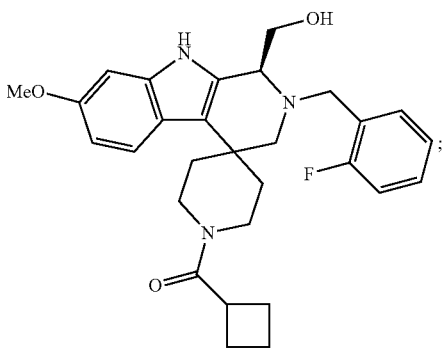 [SMILES: COc1ccc2c3c([nH]c2c1)[C@@H](CO)N(Cc1ccccc1F)CC31CCN(C(=O)C2CCC2)CC1]

(S)-cyclobutyl(2'-(3-fluorobenzyl)-1'-(hydroxymethyl)-7'-methoxy-1',2',3,9'-tetrahydrospiro[piperidine-4,4'-pyrido[3,4-b]indol]-1-yl)methanone:

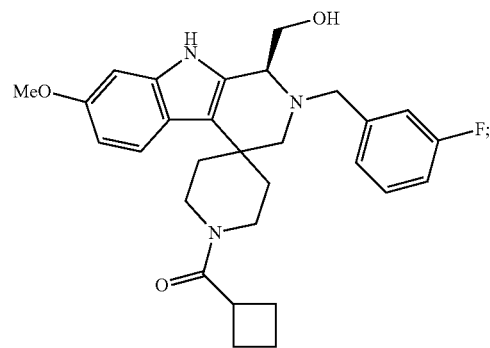 [SMILES: COc1ccc2c3c([nH]c2c1)[C@@H](CO)N(Cc1cccc(F)c1)CC31CCN(C(=O)C2CCC2)CC1]

(S)-cyclobutyl(2'-(4-fluorobenzyl)-1'-(hydroxymethyl)-7'-methoxy-1',2',3',9'-tetrahydrospiro[piperidine-4,4'-pyrido[3,4-b]indol]-1-yl)methanone:

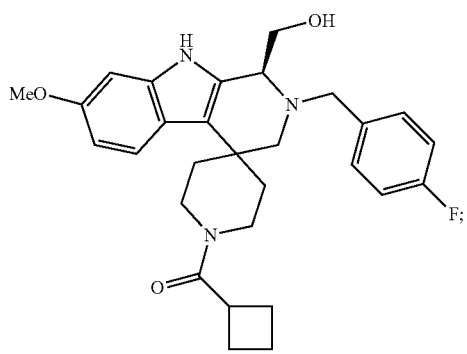 [SMILES: COc1ccc2c3c([nH]c2c1)[C@@H](CO)N(Cc1ccc(F)cc1)CC31CCN(C(=O)C2CCC2)CC1]

(S)-(2'-(2-chlorobenzyl)-1'-(hydroxymethyl)-7'-methoxy-1',2',3',9'-tetrahydrospiro[piperidine-4,4'-pyrido[3,4-b]indol]-1-yl)(cyclobutyl)methanone:

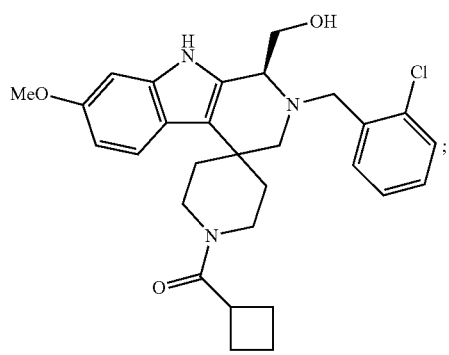 [SMILES: COc1ccc2c3c([nH]c2c1)[C@@H](CO)N(Cc1ccccc1Cl)CC31CCN(C(=O)C2CCC2)CC1]

(R)-2'-benzyl-1'-(hydroxymethyl)-7'-methoxy-N-propyl-1',2',3',9'-tetrahydrospiro[piperidine-4,4'-pyrido[3,4-b]indole]-1-carboxamide:

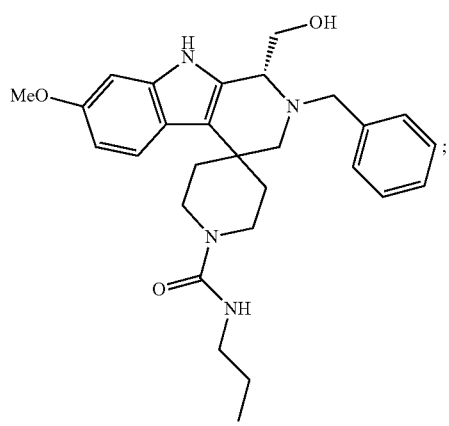 [SMILES: CCCNC(=O)N1CCC2(CC1)CN(Cc1ccccc1)[C@@H](CO)c1[nH]c3cc(OC)ccc3c12]

(S)-2'-benzyl-1'-(hydroxymethyl)-7'-methoxy-N-propyl-1',2',3',9'-tetrahydrospiro[piperidine-4,4'-pyrido[3,4-b]indole]-1-carboxamide:

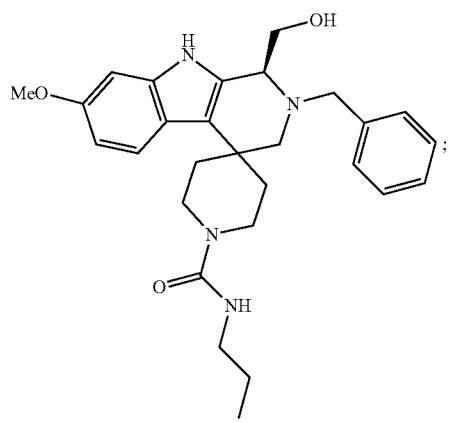 [SMILES: CCCNC(=O)N1CCC2(CC1)CN(Cc1ccccc1)[C@H](CO)c1[nH]c3cc(OC)ccc3c12]

(S)-cyclopentyl(2'-(2-fluorobenzyl)-1'-(hydroxymethyl)-7'-methoxy-1',2',3',9'-tetrahydrospiro[piperidine-4,4'-pyrido[3,4-b]indol]-1-yl)methanone:

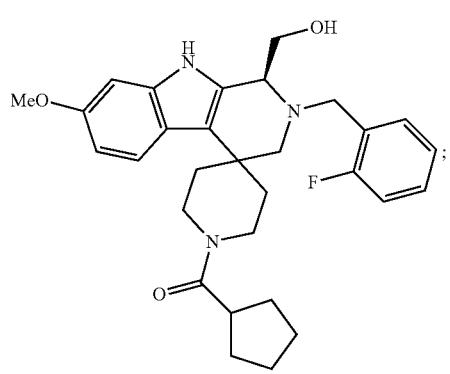 [SMILES: COc1ccc2c3c([nH]c2c1)[C@@H](CO)N(Cc1ccccc1F)CC31CCN(C(=O)C2CCCC2)CC1]

(R)-cyclopentyl(2'-(2-fluorobenzyl)-1'-(hydroxymethyl)-7'-methoxy-1',2',3',9'-tetrahydrospiro[piperidine-4,4'-pyrido[3,4-b]indol]-1-yl)methanone:

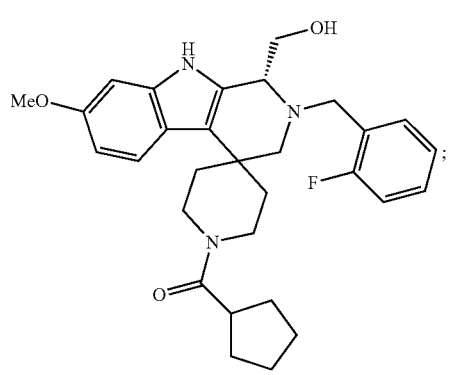 [SMILES: COc1ccc2c3c([nH]c2c1)[C@H](CO)N(Cc1ccccc1F)CC31CCN(C(=O)C2CCCC2)CC1]

or a salt, solvate, and/or stereoisomer thereof.

15. A pharmaceutical composition comprising at least one compound of claim 1 and a pharmaceutically acceptable carrier.

16. The pharmaceutical composition of claim 15, further comprising at least one additional anticancer agent selected from the group consisting of doxorubicin and ifosfamide.

17. A method of treating or preventing a synovial sarcoma in a subject in need thereof comprising administering to the subject in need thereof a therapeutically effective amount of at least one compound of claim 1.

18. The method of claim 17, wherein the subject further receives radiotherapy to treat or prevent the synovial sarcoma.

19. The method of claim 17, wherein the at least one compound is administered to the subject by at least one route selected from the group consisting of nasal, inhalational, topical, oral, buccal, rectal, pleural, peritoneal, vaginal, intramuscular, subcutaneous, transdermal, epidural, intrathecal and intravenous routes.

20. The method of claim 17, wherein the subject is human.

* * * * *

SEQUENCE LISTING

```
<160> NUMBER OF SEQ ID NOS: 1

<210> SEQ ID NO 1
<211> LENGTH: 385
<212> TYPE: PRT
<213> ORGANISM: Homo sapiens

<400> SEQUENCE: 1

Met Met Met Met Ala Leu Ser Lys Thr Phe Gly Gln Lys Pro Val Lys
1               5                   10                  15

Phe Gln Leu Glu Asp Asp Gly Glu Phe Tyr Met Ile Gly Ser Glu Val
                20                  25                  30

Gly Asn Tyr Leu Arg Met Phe Arg Gly Ser Leu Tyr Lys Arg Tyr Pro
            35                  40                  45

Ser Leu Trp Arg Arg Leu Ala Thr Val Glu Glu Arg Lys Lys Ile Val
        50                  55                  60

Ala Ser Ser His Gly Lys Lys Thr Lys Pro Asn Thr Lys Asp His Gly
65                  70                  75                  80

Tyr Thr Thr Leu Ala Thr Ser Val Thr Leu Leu Lys Ala Ser Glu Val
                85                  90                  95

Glu Glu Ile Leu Asp Gly Asn Asp Glu Lys Tyr Lys Ala Val Ser Ile
                100                 105                 110

Ser Thr Glu Pro Pro Thr Tyr Leu Arg Glu Gln Lys Ala Lys Arg Asn
            115                 120                 125

Ser Gln Trp Val Pro Thr Leu Pro Asn Ser Ser His His Leu Asp Ala
        130                 135                 140
```

| | | | | | | | | | | | | |
|---|---|---|---|---|---|---|---|---|---|---|---|---|
| Val 145 | Pro | Cys | Ser | Thr 150 | Thr | Ile | Asn | Arg | Asn 155 | Met | Gly | Arg | Asp | Lys 160 |
| Lys | Arg | Thr | Phe | Pro 165 | Leu | Cys | Phe | Asp | Asp 170 | His | Asp | Pro | Ala | Val 175 | Ile |
| His | Glu | Asn | Ala 180 | Ser | Gln | Pro | Glu | Val 185 | Leu | Val | Pro | Ile | Arg 190 | Leu | Asp |
| Met | Glu | Ile 195 | Asp | Gly | Gln | Lys 200 | Leu | Arg | Asp | Ala | Phe 205 | Thr | Trp | Asn | Met |
| Asn | Glu 210 | Lys | Leu | Met | Thr 215 | Pro | Glu | Met | Phe | Ser 220 | Glu | Ile | Leu | Cys | Asp |
| Asp 225 | Leu | Asp | Leu | Asn | Pro 230 | Leu | Thr | Phe | Val | Pro 235 | Ala | Ile | Ala | Ser | Ala 240 |
| Ile | Arg | Gln | Gln | Ile 245 | Glu | Ser | Tyr | Pro | Thr 250 | Asp | Ser | Ile | Leu | Glu 255 | Asp |
| Gln | Ser | Asp | Gln 260 | Arg | Val | Ile | Ile | Lys 265 | Leu | Asn | Ile | His | Val 270 | Gly | Asn |
| Ile | Ser | Leu 275 | Val | Asp | Gln | Phe | Glu 280 | Trp | Asp | Met | Ser | Glu 285 | Lys | Glu | Asn |
| Ser | Pro 290 | Glu | Lys | Phe | Ala | Leu 295 | Lys | Leu | Cys | Ser | Glu 300 | Leu | Gly | Leu | Gly |
| Gly 305 | Glu | Phe | Val | Thr | Thr 310 | Ile | Ala | Tyr | Ser | Ile 315 | Arg | Gly | Gln | Leu | Ser 320 |
| Trp | His | Gln | Lys | Thr 325 | Tyr | Ala | Phe | Ser | Glu 330 | Asn | Pro | Leu | Pro 335 | Thr | Val |
| Glu | Ile | Ala | Ile 340 | Arg | Asn | Thr | Gly | Asp 345 | Ala | Asp | Gln | Trp | Cys 350 | Pro | Leu |
| Leu | Glu | Thr 355 | Leu | Thr | Asp | Ala | Glu 360 | Met | Glu | Lys | Lys | Ile 365 | Arg | Asp | Gln |
| Asp | Arg 370 | Asn | Thr | Arg | Arg 375 | Met | Arg | Arg | Leu | Ala 380 | Asn | Thr | Ala | Pro | Ala |
| Trp 385 |